US009186371B2

(12) United States Patent
Taniguchi et al.

(10) Patent No.: US 9,186,371 B2
(45) Date of Patent: Nov. 17, 2015

(54) INHIBITOR OF HMGB PROTEIN-MEDIATED IMMUNE RESPONSE ACTIVATION, AND SCREENING METHOD

(75) Inventors: Tadatsugu Taniguchi, Tokyo (JP); Hideyuki Yanai, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 108 days.

(21) Appl. No.: 13/823,913

(22) PCT Filed: Sep. 14, 2011

(86) PCT No.: PCT/JP2011/071023
§ 371 (c)(1),
(2), (4) Date: Apr. 2, 2013

(87) PCT Pub. No.: WO2012/036215
PCT Pub. Date: Mar. 22, 2012

(65) Prior Publication Data
US 2013/0183348 A1    Jul. 18, 2013

(30) Foreign Application Priority Data

Sep. 17, 2010 (JP) ............... P2010-209587
Jun. 22, 2011 (JP) ............... P2011-138825

(51) Int. Cl.
| | |
|---|---|
| *C12N 15/11* | (2006.01) |
| *A61K 31/7088* | (2006.01) |
| *A61K 31/7125* | (2006.01) |
| *G01N 33/68* | (2006.01) |
| *C12N 15/117* | (2010.01) |
| *C12N 15/113* | (2010.01) |

(52) U.S. Cl.
CPC ......... *A61K 31/7088* (2013.01); *A61K 31/7125* (2013.01); *C12N 15/117* (2013.01); *G01N 33/6875* (2013.01); *C12N 15/113* (2013.01); *C12N 2310/14* (2013.01); *C12N 2310/17* (2013.01); *C12N 2310/315* (2013.01); *G01N 2333/4703* (2013.01); *G01N 2500/02* (2013.01)

(58) Field of Classification Search
CPC .................................................. C12N 15/113
See application file for complete search history.

(56) References Cited

U.S. PATENT DOCUMENTS

| 7,871,984 B2 * | 1/2011 | Sato et al. ................... 514/44 R |
| 2005/0191342 A1 * | 9/2005 | Tam et al. ................... 424/450 |
| 2006/0099207 A1 | 5/2006 | Wu et al. |
| 2008/0305073 A1 | 12/2008 | Barone et al. |
| 2009/0270481 A1 * | 10/2009 | MacLachlan et al. ....... 514/44 A |

FOREIGN PATENT DOCUMENTS

| EP | 1702620 A1 | 9/2006 |
| JP | 2008-504335 A | 2/2008 |
| JP | 2009-517404 A | 4/2009 |
| WO | 02/22809 A2 | 3/2002 |
| WO | 2006/002971 A2 | 1/2006 |
| WO | 2006/052900 A2 | 5/2006 |
| WO | 2007/076200 A2 | 7/2007 |
| WO | 2007/084253 A2 | 7/2007 |
| WO | 2009/023819 A2 | 2/2009 |

OTHER PUBLICATIONS

Ivanov et al., "A novel role for HMGB1 in TLR9-mediated inflammatory responses to CpG-DNA," Blood, 110: 1970-1981 (2007).
Yasuda et al., "CpG motif-independent activation of TLR9 upon endosomal translocation of "natural" phosphodiester DNA," European Journal of Immunology, 36: 431-436 (2006).
Kawai et al., "Innate immune recognition of viral infection," Nature Reviews Immunology, 7: 131-137 (2006).
Yoneyama et al., "Function of RIG-I-like Receptors in Antiviral Innate Immunity," The Journal of Biological Chemistry, 282: 15315-15318 (2007).
Burckstummer et al., "An orthogonal proteomic-genomic screen identifies AIM2 as a cytoplasmic DNA sensor for the inflammasome," Nature Immunology, 10: 266-272 (2009).
Haas et al., "The DNA Sugar Backbone 2' Deoxyribose Determines Toll-like Receptor 9 Activation," Immunity, 28: 315-323 (2008).
Cowdery et al., "Bacterial DNA Induces NK Cells to Produce IFN-y In Vivo and Increases the Toxicity of Lipopolysaccharides," The Journal of Immunology, 156: 4570-4575 (1996).
International Search Report issued in corresponding International Application No. PCT/JP2011/071023 dated Oct. 18, 2011.
Yanai et al., "HMGB proteins function as universal sentinels for nucleic-acid-mediated innate immune responses," Nature, 45215: 99-104 (2009).
Klinman, "Immunotherapeutic Uses of CpG Oligodeoxynucleotides," Nature Reviews Immunology, 4: 249-258 (2004).
Extended European Search Report issued in counterpart European Patent Application No. 11825215.4 dated Apr. 1, 2014.
Peter et al., "Characterization of suppressive oligodeoxynucleotides that inhibit Toll-like receptor-9-mediated activation of innate immunity," Immunology, 123: 118-128 (2008).
Tian et al., "Toll-like receptor 9-dependent activation by DNA-containing immune complexes is mediated by HMGB1 and RAGE," Nature Immunology, 8: 487-496 (2007).
Yanai et al., "Essential role of high-mobility group box proteins in nucleic acid-mediated innate responses," Journal of Internal Medicine, 270: 301-308 (2011).
Yanai et al., "Suppression of immune responses by nonimmunogenic oligodeoxynucleotides with high affinity for high-mobility group box proteins (HMGBs)," Proceedings of the National Academy of Sciences, 108: 11542-11547 (2011).

\* cited by examiner

*Primary Examiner* — Brian Whiteman
(74) *Attorney, Agent, or Firm* — Morgan, Lewis & Bockius LLP

(57) ABSTRACT

Provided are an inhibitor of activation of an immune response mediated by an HMGB protein, the inhibitor containing at least one compound selected from the group consisting of a phosphorothioate oligonucleotide and a derivative thereof, and a method of screening for an inhibitor or enhancer of activation of an immune response mediated by an HMGB protein.

21 Claims, 62 Drawing Sheets

*Fig.7*
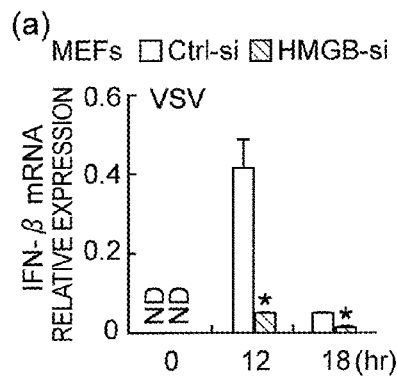
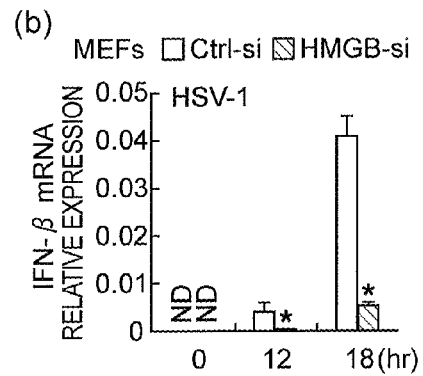
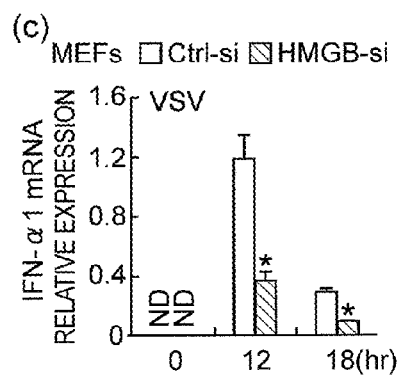
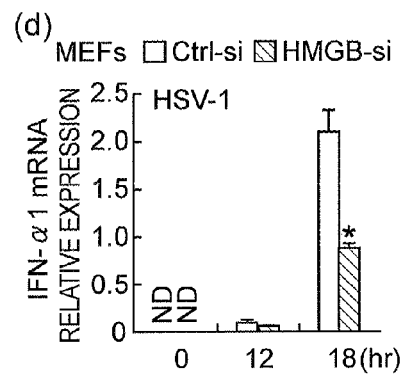
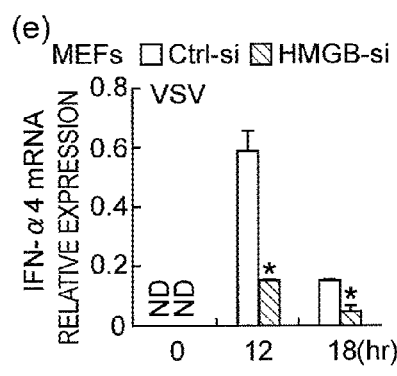
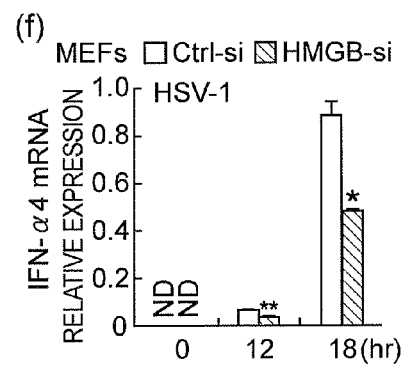

Fig.45
(a)
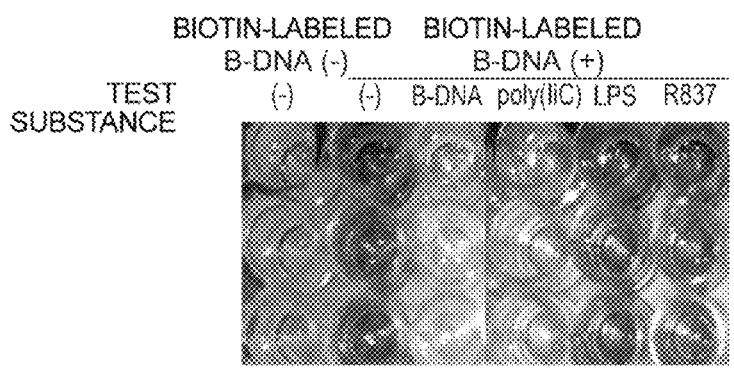
(b)
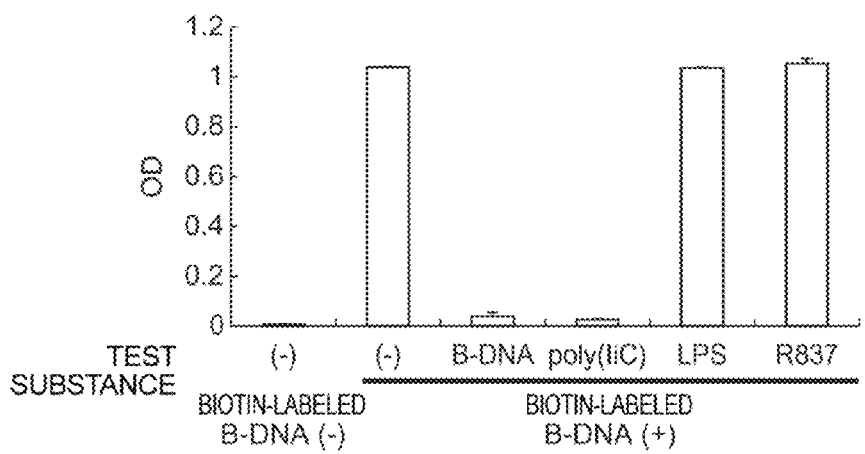

Fig.46

| | |
|---|---|
| CpG-B(S) | TCCATGA<u>CG</u>TTCCTGATGCT |
| CpG-Rev(S) | TCCATGA<u>GC</u>TTCCTGATGCT |
| CpG-M(S) | TCCATGA<u>GG</u>TTCCTGATGCT |
| PS | BASE-FREE (CONTAINING ONLY BACKBONE) |

INHIBITOR OF HMGB PROTEIN-MEDIATED IMMUNE RESPONSE ACTIVATION, AND SCREENING METHOD

A computer readable text file, entitled "SequenceListing.txt," created on or about Mar. 14, 2013 with a file size about 17 kb contains the sequence listing for this application and is hereby incorporated by reference in its entirety.

TECHNICAL FIELD

The present invention relates to an inhibitor of activation of an immune response mediated by an HMGB protein and a method of screening for an inhibitor or enhancer of activation of an immune response mediated by an HMGB protein.

BACKGROUND ART

In immune response and its control, discrimination between self and nonself is the basis. The innate immune system and the adaptive immune system carry out this discrimination by the respective specific mechanisms and establish and maintain each mechanism not to response to self, so-called immune tolerance. Since activation of the innate immune response is known to be also involved in induction of the adaptive immune response, inhibition of the innate immune response is known to be also effective for inhibition of the adaptive immune response.

It has been revealed that in the adaptive immune system, after construction of a lymphocyte repertoire expressing random antigen receptors, the majority of autoreactive lymphocytes are eliminated by a central tolerance mechanism and the autoreactive lymphocytes still remaining at periphery are inhibited by a peripheral tolerance mechanism.

Though the recognition of an antigen by the adaptive immune system is characterized by the recognition of a specific molecular structure by a lymphocyte antigen receptor, the innate immune system is regarded to recognize the molecular pattern possessed by, for example, a pathogen, and many innate immune activating receptors including a Toll-like receptor (TLR) are known. In particular, the innate immune activation by nucleic acid is important for elimination of pathogens such as viruses and is simultaneously regarded to be involved in onset and exacerbation of various immune pathological conditions and is therefore drawing much interest. However, there are many unknown aspects in the discrimination mechanism by nucleic acid in the innate immune system, though receptor molecular groups, such as Toll-like receptor (TLR) 3, TLR7, TLR9, RIG-1-like receptor, DAI, and AIM2, have been identified as molecular groups carrying out immune responses activated by nucleic acid, the whole picture is still unclear (see, e.g., Non Patent Literatures 1 to 3).

In HMGB (high-mobility group box) proteins, it is known that HMGB1, HMGB2 and HMGB3 are present. These HMGB proteins are abundantly present in nuclei and are believed to be involved in chromatin structure and in control of transcription. In addition, they are known to be also present in cytoplasms and outside cells.

Patent Literature 1 describes a synthetic double-stranded nucleic acid or a nucleic acid analog molecule that inhibits binding between an extracellularly secreted HMGB1 protein and an advanced glycation end product receptor (RAGE) on a cell surface.

Patent Literature 2 describes a HMGB1 antagonist that inhibits interaction between the extracellularly secreted HMGB1 protein and the RAGE.

Non Patent Literature 4 describes that a base-free phosphorothioate deoxyribose homopolymer has a high affinity to TLR9 and TLR7 and acts as an antagonist of these TLRs.

Non Patent Literature 5 describes that though administration of a phosphorothioate oligonucleotide including a nucleotide sequence of 5'-TCCATGACGTTCCTGATGCT-3' (SEQ ID NO: 37) to a mouse induces an IFN (interferon)-γ response, a phosphorothioate oligonucleotide including a nucleotide sequence of 5'-TCCATGAGCTTCCTGATGCT-3' (SEQ ID NO: 38) does not cause such a response.

CITATION LIST

Patent Literature

Patent Literature 1: National Publication of International Patent Application No. 2008-504335
Patent Literature 2: National Publication of International Patent Application No. 2009-517404

Non Patent Literature

Non Patent Literature 1: Kawai T. et al., Nat. Rev. Immunol 7: 131-137, 2006
Non Patent Literature 2: Yoneyama et al., J. Biol. Chem. 282: 15315-15318, 2007
Non Patent Literature 3: Burckstummer T. et al., Nat. Immunol. 10: 266-272, 2009
Non Patent Literature 4: Haas T. et al., Immunity, 28: 315-323, 2008
Non Patent Literature 5: Cowdery J S. et al., J. Immunol. 156: 4570-4575, 1996

SUMMARY OF INVENTION

Technical Problem

It is an object of the present invention to provide an inhibitor of activation of an immune response mediated by an HMGB protein and a method of screening for an inhibitor or enhancer of activation of an immune response mediated by an HMGB protein.

Solution to Problem

The present invention provides an inhibitor of activation of an immune response mediated by an HMGB protein, the inhibitor consisting of at least one compound selected from the group consisting of a phosphorothioate oligonucleotide and a derivative thereof and inhibiting activation of the immune response mediated by the HMGB protein through binding to the HMGB protein.

The present invention also provides a method of inhibiting activation of an immune response mediated by an HMGB protein, the method including a step of administering at least one compound selected from the group consisting of a phosphorothioate oligonucleotide and a derivative thereof to a living body.

The present invention also provides at least one compound selected from the group consisting of a phosphorothioate oligonucleotide and a derivative thereof to be used as an inhibitor of activation of an immune response mediated by an HMGB protein.

The present invention also provides an application of at least one compound selected from the group consisting of a phosphorothioate oligonucleotide and a derivative thereof to an inhibitor of activation of an immune response mediated by an HMGB protein.

The present inventors have revealed that an HMGB protein is indispensable for activation of an immune response mediated by nucleic acid. That is, the present inventors have revealed that the activation of an immune response mediated by nucleic acid is mediated by an HMGB protein. The present inventors have further revealed that the above-mentioned compound strongly binds to an HMGB protein and thereby strongly inhibits the activation of an immune response mediated by the HMGB protein. Accordingly, the above-mentioned compound can be utilized as an inhibitor of activation of an immune response mediated by the HMGB protein. The above-mentioned inhibitor inhibits not only the immune response mediated by nucleic acid but also the activation of an immune response mediated by the HMGB protein.

The above-mentioned compound is preferably a phosphorothioate oligonucleotide not including any unmethylated CG sequence and having a length of 5 to 40 nucleotides and is more preferably a phosphorothioate oligonucleotide including (1) a nucleotide sequence as set forth in SEQ ID NO: 40 or (2) a nucleotide sequence having deletion, substitution, or addition of one to several nucleotides in the nucleotide sequence as set forth in SEQ ID NO: 40 and having a binding ability to an HMGB protein.

These phosphorothioate oligonucleotides can be utilized as inhibitors of the activation of an immune response mediated by an HMGB protein.

The above-mentioned compound is a derivative of the phosphorothioate oligonucleotide, and the derivative may be a base-free phosphorothioate deoxyribose homopolymer (hereinafter, sometimes referred to as "PS"). The PS is a compound having a structure in which the base moieties are removed from a phosphorothioate oligonucleotide.

As shown in Examples, PS can be utilized as an inhibitor of activation of an immune response mediated by an HMGB protein.

The inhibitor of the present invention strongly inhibits the activation of an immune response mediated by an HMGB protein by inhibiting a binding between a nucleic acid activating an immune response and an HMGB protein in a cell. That is, the inhibitor of the present invention inhibits the activation of an immune response mediated by an HMGB protein in a cell on the basis of the mechanism revealed by the present inventors for the first time.

Examples of the activation of an immune response mediated by an HMGB protein include antigen-specific adaptive immune system, multiple sclerosis, excessive immune response to a dead cell, organ transplant rejection, autoimmune disease, inflammatory bowel disease, allergy, septicemia, tumor growth by inflammation and inflammatory diseases caused by a nucleic acid-containing pathogen. It is possible to prevent or treat (remedy) these symptoms by administering the inhibitor of the present invention to a human or animal living body.

The present invention also provides a composition for inhibiting activation of an immune response mediated by an HMGB protein, the composition containing the above-mentioned inhibitor and a pharmaceutically acceptable carrier.

The present invention also provides a method of screening for an inhibitor or enhancer of activation of an immune response mediated by an HMGB protein, the method including a mixing step of mixing an HMGB protein and a labeled nucleic acid in the presence and absence of a test substance; a quantifying step of quantifying the HMGB protein bound to the labeled nucleic acid; and a determination step of determining that the test substance is an inhibitor of activation of an immune response mediated by the HMGB protein when the amount of the HMGB protein bound to the labeled nucleic acid in the presence of the test substance is less than the amount of the HMGB protein bound to the labeled nucleic acid in the absence of the test substance and determining that the test substance is an enhancer of activation of an immune response mediated by the HMGB protein when the amount of the HMGB protein bound to the labeled nucleic acid in the presence of the test substance is higher than the amount of the HMGB protein bound to the labeled nucleic acid in the absence of the test substance.

The present invention also provides a method of screening for an inhibitor or enhancer of activation of an immune response mediated by an HMGB protein, the method including an incubation step of incubating an immobilized HMGB protein in the presence and absence of a test substance; a labeled-nucleic-acid-contacting-step of contacting a labeled nucleic acid with the immobilized HMGB protein after the incubation step; a quantifying step of quantifying the labeled nucleic acid bound to the immobilized HMGB protein; and a determination step of determining that the test substance is an inhibitor of activation of an immune response mediated by the HMGB protein when the amount of the labeled nucleic acid bound to the immobilized HMGB protein on which the incubation step is performed in the presence of the test substance is less than the amount of the labeled nucleic acid bound to the immobilized HMGB protein on which the incubation step is performed in the absence of the test substance and determining that the test substance is an enhancer of activation of an immune response mediated by the HMGB protein when the amount of the labeled nucleic acid bound to the immobilized HMGB protein on which the incubation step is performed in the presence of the test substance is higher than the amount of the labeled nucleic acid bound to the immobilized HMGB protein on which the incubation step is performed in the absence of the test substance.

The present invention also provides a method of screening for an inhibitor or enhancer of activation of an immune response mediated by an HMGB protein, the method including a contacting step of contacting an HMGB protein with an immobilized nucleic acid in the presence and absence of a test substance; a quantifying step of quantifying the HMGB protein bound to the immobilized nucleic acid; and a determination step of determining that the test substance is an inhibitor of activation of an immune response mediated by the HMGB protein when the amount of the HMGB protein bound to the immobilized nucleic acid in the presence of the test substance is less than the amount of the HMGB protein bound to the immobilized nucleic acid in the absence of the test substance and determining that the test substance is an enhancer of activation of an immune response mediated by the HMGB protein when the amount of the HMGB protein bound to the immobilized nucleic acid in the presence of the test substance is higher than the amount of the HMGB protein bound to the immobilized nucleic acid in the absence of the test substance.

According to the methods of screening of the present invention, it is possible to screen for an inhibitor or enhancer of activation of an immune response mediated by an HMGB protein. These screening methods are based on a novel mechanism in which the activation of an immune response is mediated by an HMGB protein, which has been revealed by the present inventors for the first time. It is possible to perform screening simply and efficiently by these screening methods.

Advantageous Effects of Invention

According to the present invention, an inhibitor based on a novel principle of the activation of an immune response mediated by an HMGB protein, i.e., an excessive immune response to dead cells, an organ transplant rejection, an autoimmune disease, an inflammatory bowel disease, an allergy, septicemia, tumor growth by inflammation, an inflammatory disease caused by a nucleic acid-containing pathogen, etc., is provided. In addition, a method of screening for an inhibitor or enhancer of activation of an immune response mediated by an HMGB protein is provided.

BRIEF DESCRIPTION OF DRAWINGS

FIG. 7 is a set of graphs showing the results of Example 7.
FIG. 45 provides photographs (a) and a graph (b) showing the results of Example 43.
FIG. 46 is a diagram showing the structures of CpG-B(S), CpG-Rev(S), CpG-M(S) and PS.

DESCRIPTION OF EMBODIMENTS

Figure 1:
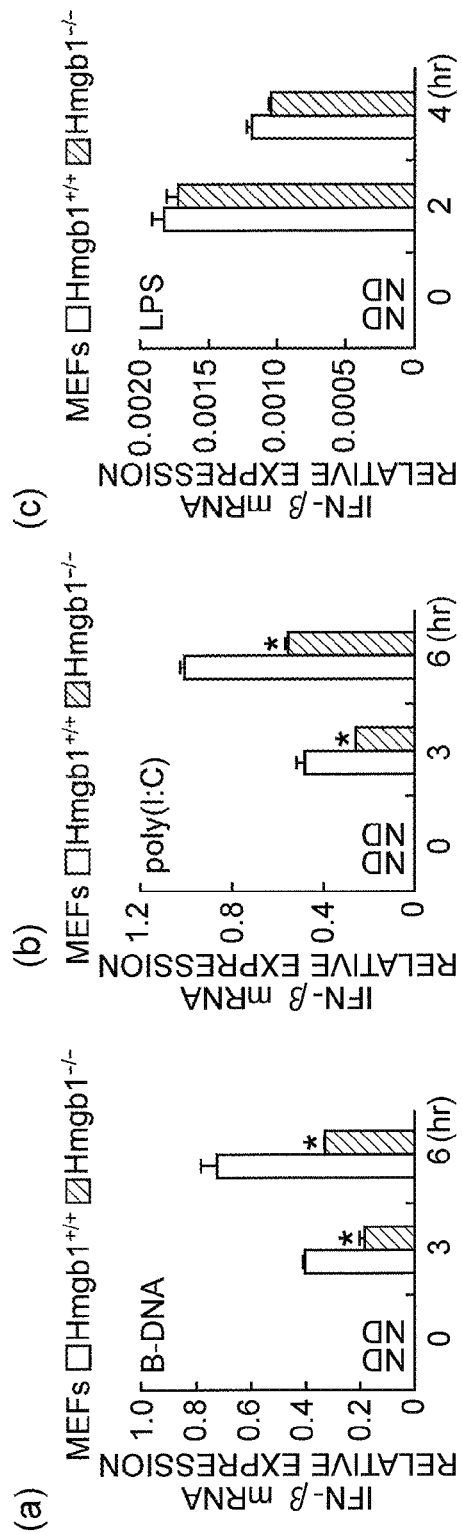
FIG. 1 is a set of graphs showing the results of Example 1.

An inhibitor of activation of an immune response mediated by an HMGB protein, on the basis of the mechanism newly elucidated by the present inventors, is provided. This inhibitor consists of at least one compound selected from the group consisting of a phosphorothioate oligonucleotide and a derivative thereof.

The phosphorothioate oligonucleotide is an oligonucleotide derivative obtained by conversion of the phosphodiester linkage in an oligodeoxyribonucleotide into phosphorothioate linkage.

It is preferable that the inhibitor consists of a phosphorothioate oligonucleotide not including any unmethylated CG sequence and having a length of 5 to 100 nucleotides. The length of the phosphorothioate oligonucleotide is more preferably 10 to 40 nucleotides, still more preferably 15 to 30 nucleotides, and most preferably 15 to 20 nucleotides. Such a phosphorothioate oligonucleotide can inhibit the activation of an immune response mediated by an HMGB protein by binding to the HMGB protein and thereby masking the HMGB protein. The unmethylated cytosine.guanine (CG) sequence is an unmethylated 5'-CG-3' nucleotide sequence. An oligonucleotide of 5 to 100 nucleotides not including the unmethylated CG sequence does not activate any immune response mediated by an HMGB protein. In contrast, an oligonucleotide having a length exceeding 100 nucleotides may activate an immune response.

The phosphorothioate oligonucleotide is more preferably a phosphorothioate oligonucleotide consisting of the nucleotide sequence as set forth in SEQ ID NO: 40 or a nucleotide sequence having deletion, substitution, or addition of one to several nucleotides in the nucleotide sequence as set forth in SEQ ID NO: 40 and having a binding ability to an HMGB protein. The nucleotide sequence as set forth in SEQ ID NO: 40 is 5'-TCCATGAGSTTCCTGATGCT-3' wherein S represents G or C. The phosphorothioate oligonucleotide consisting of the nucleotide sequence in which S is C corresponds to CpG-Rev(S) (SEQ ID NO: 38) described below, and the phosphorothioate oligonucleotide consisting of the nucleotide sequence in which S is G corresponds to CpG-M(S) (SEQ ID NO: 39) described below. In addition, the term, one to several, means one to ten, more preferably one to five, still more preferably one to three, and most preferably one or two.

It is further preferable that the phosphorothioate oligonucleotide consists of the nucleotide sequence as set forth in SEQ ID NO: 40. The phosphorothioate oligonucleotide consisting of this nucleotide sequence can strongly inhibit the activation of an immune response mediated by an HMGB protein.

The derivative of the phosphorothioate oligonucleotide is not particularly limited as long as it has a binding ability to an HMGB protein, and examples thereof include those where the backbone of the phosphorothioate oligonucleotide is at least partially converted into phosphodiester linkage, those where the deoxyriboses are at least partially converted into riboses, and those where bases are at least partially removed, at least partially converted into PNAs (peptide nucleic acids), at least partially converted into LNAs (locked nucleic acids), or at least partially converted into base analogues. Among these derivatives, base-free phosphorothioate deoxyribose homopolymer (PS) is preferred.

The PS is a compound represented by a chemical formula $(C_5H_8O_4PS)_n$ and has a structure obtained by removing all base moieties from a phosphorothioate oligonucleotide. It is preferable that n is 10 to 100, and it is more preferable that n is 15 to 25.

The phosphorothioate oligonucleotide, PS and a derivative thereof may be those synthesized using, for example, a nucleic acid synthesizer or those purchased from manufacturers such as Hokkaido System Science Co., Ltd. or Fasmac Co., Ltd.

As shown in Examples, the PS can inhibit the activation of an immune response mediated by an HMGB protein in vitro by being administered at a concentration of 0.1 to 50 µM, more preferably 1 to 10 µM, and most preferably 5 µM. The results can directly apply to in vivo.

The CpG-B ODN, as shown in Examples, can inhibit the activation of an immune response mediated by an HMGB protein in in vitro experiments using cells such as TLR9 (Toll-like receptor 9) deficient cells or MEFs of which expression level of TLR9 is low when it is administered at a concentration of 0.1 to 10 µM, more preferably 0.3 to 3 µM, and most preferably 1 µM. The results can directly apply to in vivo.

In the case of clinically using the inhibitor of activation of an immune response mediated by an HMGB protein, the inhibitor may be in a form of a composition of the inhibitor appropriately mixed with additives such as an excipient, a stabilizer, a preservative, a buffer, a solubilizer, an emulsifier, a diluent and an isotonic agent. The composition for inhibiting activation of an immune response mediated by an HMGB protein contains a pharmaceutically acceptable carrier, in addition to the inhibitor as an essential component. Examples of the pharmaceutically acceptable carrier include various components that are usually used in, for example, medicines, i.e., water, lower alcohols, polyhydric alcohols, oils, surfactants, humectants, water-soluble high molecular compounds, thickeners, film forming agents, powders, chelating agents, pH adjusters, extracts from animals and plants and microorganisms, saccharides, amino acids, organic amines, synthetic resin emulsions, skin nutrients, vitamins, antioxidants, antioxidant assistants, flavors, various medicinal agents, etc., and they can be added within a range that does not impair the effects of the inhibitor. Examples of the dosage form include oral preparations such as tablets, capsules, granules, powders, and syrups; parenteral preparations such as injections, suppositories, and liquids; and local administration such as ointments, creams and patches. The dosage of the inhibitor is appropriately selected depending on the symptoms, age, body weight, administration method, etc.

In an embodiment, the activation of an immune response mediated by an HMGB protein being inhibited by the inhibitor is the activation of an immune response mediated by nucleic acid. The nucleic acid that activates an immune response refers to, for example, a double-stranded RNA (dsRNA), a single-stranded RNA (ssRNA), a 5'-triphosphorylated RNA, a micro RNA, a viral RNA, a viral DNA, a microbial DNA (DNA derived from a microorganism), a eukaryotic DNA, a B-DNA (synthetic DNA having a steric structure of a normal DNA, B-type DNA), an ISD (IFN-stimulatory DNA), or an unmethylated oligonucleotide. The ISD is a synthetic DNA (SEQ ID NO: 36) of 45 nucleotides, and the induction of type I IFN by introducing the ISD into cells is known to be mediated by TLR-independent activation of IRF-3. Throughout the specification, these nucleic acids that activate immune responses may be collectively referred to as "all immunogenic nucleic acids". In addition, throughout the specification, the term "immune response" includes both "innate immune response" and "adaptive immune response".

In an embodiment, the activation of an immune response mediated by an HMGB protein being inhibited by the inhibitor is not the activation of an immune response mediated by nucleic acid, but is the activation of an immune response based on the function of the HMGB protein as a cytokine. The activation of an immune response based on the function of the HMGB protein as a cytokine is inhibited by binding of the inhibitor to the HMGB protein.

Examples of the activation of an immune response mediated by an HMGB protein include antigen-specific adaptive immune system, multiple sclerosis, excessive immune response to a dead cell, organ transplant rejection, autoimmune disease such as rheumatoid arthritis, inflammatory bowel disease, allergy, septicemia, tumor growth by inflammation and inflammatory disease caused by nucleic acid-containing pathogen. These immune responses are examples that cause disadvantages. Here, the excessive immune response means a negative chain reaction in that, for example, as in necrotic inflammation of the liver, cells necrotized by an exogenous factor, such as viral infection, a circulatory disorder, a metabolic disorder, or a simple inflammatory reaction, induce inflammation, and this inflammation further causes necrosis of other cells. In addition, it is preferable that the dead cells are necrotic cells. Incidentally, the nucleic acid-containing pathogen refers to a virus, a microorganism, a parasite, etc.

It is known that administration of the nucleic acid that activates an immune response into cytoplasm of an animal cell, including a human cell, by using a cationic lipid such as Lipofectamine (trade name, Invitrogen Corporation) or DOTAP (trade name, F. Hoffmann-La Roche Ltd.) induces gene expression of a type I IFN (interferon), such as IFN-$\beta$, IFN-$\alpha$1, or IFN-$\alpha$4, a chemokine, or an inflammatory cytokine and initiates an immune response.

CpG oligodeoxyribonucleotide (hereinafter, sometimes referred to as CpG ODN), poly(I:C), poly(U), and poly(dA:dT)•(dT:dA) may be respectively used as the unmethylated oligonucleotide, the dsRNA, the ssRNA and the B-DNA.

The CpG ODN is a synthetic oligonucleotide including an unmethylated CG sequence (5'-CG-3'), which frequently appears in bacterial DNAs. The CpG ODN includes, for example, CpG-A ODN (also referred to as type D) having a poly G tail and CpG-B ODN (also referred to as type K) that strongly activates B-cells and induces Th1-type cytokine production. As the CpG-B ODN, for example, those including a sequence such as 5'-TCCATGACGTTCCTGATGCT-3' (SEQ ID NO: 1) can be used. In addition, as the CpG-A ODN, for example, those including a sequence such as 5'-GGTG-CATCGATGCAGGGGG-3' (SEQ ID NO: 2) can be used. These CpG ODNs may have a structure in which the phosphodiester linkage is partially converted into, for example, phosphorothioate linkage.

The CpG ODN is preferably a 10- to 30-mer, the poly(I:C) is preferably a 10- to 10000-mer, the poly(U) is preferably a 10- to 10000-mer, and the poly(dA:dT)•(dT:dA) is preferably a 10- to 10000-mer.

The present invention provides a method of screening for an inhibitor or enhancer of activation of an immune response mediated by an HMGB protein. A first embodiment of this screening method includes a mixing step of mixing an HMGB protein and a labeled nucleic acid in the presence and absence of a test substance; a quantifying step of quantifying the HMGB protein bound to the labeled nucleic acid; and a determination step of comparing the amount of the HMGB protein bound to the labeled nucleic acid in the presence of the test substance to the amount of the HMGB protein bound to the labeled nucleic acid in the absence of the test substance and determining that the test substance is an inhibitor of activation of an immune response mediated by the HMGB protein when the amount of the HMGB protein bound to the labeled nucleic acid in the presence of the test substance is less than the amount of the HMGB protein bound to the labeled nucleic acid in the absence of the test substance and determining that the test substance is an enhancer of activation of an immune response mediated by the HMGB protein when the amount of the HMGB protein bound to the labeled nucleic acid in the presence of the test substance is higher than the amount of the HMGB protein bound to the labeled nucleic acid in the absence of the test substance.

In the mixing step, as the HMGB protein, any of the recombinants of HMGB1, 2 and 3 can be suitably used. The present inventors have revealed for the first time that the HMGB proteins bind to all immunogenic nucleic acids.

The labeled nucleic acid is not particularly limited, and examples thereof include synthetic nucleic acids such as CpG ODNs, poly(I:C), poly(U), B-DNAs, 5'-triphosphorylated RNAs, and micro RNAs; viral DNAs such as HSV-1 and vaccinia virus DNAs; microbial DNAs; and bovine thymus DNAs. However, the synthetic nucleic acids are more preferable because of their higher homogeneity. The synthetic nucleic acid is preferably a 10- to 100-mer and more preferably a 15- to 25-mer. The labeling is not particularly limited and may be performed with, for example, biotin, a fluorescent dye such as FITC, digoxigenin, or a radioisotope.

The test substance is not particularly limited as long as it does not activate any immune response when animal cells, including human cells, are stimulated with the test substance only, and a nucleic acid, a nucleic acid analogue, a protein, a low molecular compound, etc. can be used as the test substance.

Whether or not an immune response is activated by stimulating animal cells with a test substance can be investigated by measuring whether or not the expression of, for example, a type I IFN (interferon), such as IFN-$\beta$, IFN-$\alpha$1, or IFN-$\alpha$4, a chemokine, or an inflammatory cytokine is increased by the stimulation with the test substance. When the expression of such a gene or protein is increased, it can be determined that the immune response is activated.

In the mixing step, it is preferable that the concentration of the test substance is 0.1 to 100 μM. In addition, it is preferable that the concentration of the HMGB protein is 1 to 200 μg/mL. In addition, it is preferable that the concentration of the labeled nucleic acid is 0.1 to 100 μM. It is preferable to mix these materials in a solvent, such as a buffer containing an appropriate protease inhibitor, to perform a reaction for 0.5 to 24 hours.

The quantifying step may be performed by a pull-down assay using streptavidin-bound magnetic beads, anti-FITC antibody-bound magnetic beads, or the like or may be performed by an electrophoretic mobility shift assay (EMSA) or the like.

For example, in a case of a pull-down assay using a biotin-labeled nucleic acid as the labeled nucleic acid and using streptavidin-bound magnetic beads, the streptavidin-bound magnetic beads are added to a sample obtained in the mixing step to allow the biotin-labeled nucleic acid in the sample to bind to the streptavidin-bound magnetic beads. Subsequently, the HMGB protein bound to the labeled nucleic acid is collected utilizing the magnetism of the magnetic beads. The collected sample is subjected to, for example, SDS-polyacrylamide gel electrophoresis (SDS-PAGE), and then the HMBG protein on the gel is transferred to, for example, a PVDF membrane, is stained using an anti-HMGB antibody, and then can be quantified by densitometric analysis or the like.

In the determination step, the amounts of the HMGB protein bound to the labeled nucleic acid in the presence and absence of a test substance are compared to each other, and the test substance is determined as an inhibitor of activation of an immune response mediated by the HMGB protein when the amount of the HMGB protein bound to the labeled nucleic acid in the presence of the test substance is less than the amount of the HMGB protein bound to the labeled nucleic acid in the absence of the test substance. Alternatively, the test substance is determined as an enhancer of activation of an immune response mediated by the HMGB protein when the amount of the HMGB protein bound to the labeled nucleic acid in the presence of the test substance is higher than the amount of the HMGB protein bound to the labeled nucleic acid in the absence of the test substance.

In the screening method of the first embodiment, the following modification is possible. As the labeled nucleic acid, a compound selected from the group consisting of phosphorothioate oligonucleotides and derivatives thereof, for example, a phosphorothioate oligonucleotide consisting of the nucleotide sequence as set forth in SEQ ID NO: 40, is used.

Here, the labeled nucleic acid and the HMGB protein are each labeled with fluorescent materials being related to each other to cause FRET (fluorescence resonance energy transfer). Examples of the fluorescent material pair being in such a relationship include N,N,N',N''-tetramethyl-6-carboxy rhodamine (TAMRA) and 5-carboxyfluorescein (FAM), 6-carboxy-X-rhodamine (ROX) and FAM, and BHQ-1 and 2',7'-dimethoxy-4',5'-dichloro-6-carboxyfluorescein (JOE). By using such a pair, FRET is caused by binding between the compound and the HMGB protein to cause a shift in fluorescence wavelength generated by the excitation wavelength. Accordingly, it is possible to easily detect whether or not the compound and the HMGB protein are bound to each other by observing the fluorescence of the sample.

In the mixing step, the labeled nucleic acid and the HMGB protein labeled with a pair of fluorescent materials are mixed in the presence and absence of a test substance. Subsequently, in the quantifying step, the HMGB protein bound to the labeled nucleic acid is quantified through quantitative evaluation of the degree of the binding between the labeled nucleic acid and the HMGB protein by measuring whether or not the FRET occurs through fluorescence observation.

Subsequently, in the determination step, the amounts of the HMGB protein bound to the labeled nucleic acid in the presence and absence of the test substance are compared to each other, and the test substance is determined as an inhibitor of activation of an immune response mediated by the HMGB protein when the amount of the HMGB protein bound to the labeled nucleic acid in the presence of the test substance is less than the amount of the HMGB protein bound to the labeled nucleic acid in the absence of the test substance. Alternatively, the test substance is determined as an enhancer of activation of an immune response mediated by the HMGB protein when the amount of the HMGB protein bound to the labeled nucleic acid in the presence of the test substance is higher than the amount of the HMGB protein bound to the labeled nucleic acid in the absence of the test substance.

It is possible by such a modification to perform more simply and efficiently screening for an inhibitor or enhancer of activation of an immune response mediated by an HMGB protein.

A second embodiment of the method of screening for an inhibitor or enhancer of activation of an immune response mediated by an HMGB protein includes an incubation step of incubating an immobilized HMGB protein in the presence and absence of a test substance; a labeled nucleic acid contacting step of contacting a labeled nucleic acid with the immobilized HMGB protein after the incubation step; a quantifying step of quantifying the labeled nucleic acid bound to the immobilized HMGB protein; and a determination step of determining that the test substance is an inhibitor of activation of an immune response mediated by the HMGB protein when the amount of the labeled nucleic acid bound to the immobilized HMGB protein on which the incubation step is performed in the presence of the test substance is less than the amount of the labeled nucleic acid bound to the immobilized HMGB protein on which the incubation step is performed in the absence of the test substance and determining that the test substance is an enhancer of activation of an immune response mediated by the HMGB protein when the amount of the labeled nucleic acid bound to the immobilized HMGB protein on which the incubation step is performed in the presence of the test substance is higher than the amount of the labeled nucleic acid bound to the immobilized HMGB protein on which the incubation step is performed in the absence of the test substance.

It is possible by this screening method to perform more simply and efficiently screening for an inhibitor or enhancer of activation of an immune response mediated by an HMGB protein.

In the incubation step, the immobilized HMGB protein is left in the presence and absence of a test substance. As the HMGB protein, any of the recombinants of HMGB1, 2 and 3 can be suitably used.

The HMGB protein is used by being immobilized to a solid support in advance. The solid support is not particularly limited, and, for example, those in a form of a microplate, a microchip, a bead, a film, a sheet, etc. made of an inorganic material such as glass, a ceramic, or a metal oxide, a natural polymer, a synthetic polymer, etc. can be utilized. The solid support may be modified with a functional group such as an amino group ($-NH_2$) or a carboxyl group ($-COOH$) on the surface.

For example, in a case of using a 96-well plate as the solid support, an HMGB protein can be immobilized by dispensing a solution of the HMGB protein dissolved in a buffer such as phosphate buffered saline (PBS) at a concentration of 1 to 100 μg/mL to each well of the microplate and incubated at 4 to 37° C. for 0.5 to 24 hours. It is preferable to wash this microplate with a buffer such as PBS before the use to remove the unbound HMGB protein. In addition, in order to prevent non-specific adsorption, it is preferable to block the non-specific adsorption by adding a buffer such as 2% bovine serum albumin (BSA)-containing PBS (2% BSA-PBS) to each well.

The test substance is not particularly limited as long as it does not activate any immune response when animal cells, including human cells, are stimulated with the test substance only, and a nucleic acid, a nucleic acid analogue, a protein, a low molecular compound, etc. can be used. As the solvent for the test substance, a buffer such as PBS can be used. In the case of performing the incubation step in the absence of the test substance, only a buffer not containing the test substance may be used. It is preferable that the concentration of the test substance in the incubation step is 0.1 to 100 μM. In addition, in the incubation step, a test group in which the incubation step is performed in the presence of a control material" may be provided. As the control material, for example, a nucleic acid that is known to bind to the HMGB protein or a compound that is known not to bind to the HMGB protein can be used, e.g., B-DNA can be used as a material that is known to bind to the HMGB protein. It is preferable to perform the incubation step at 4 to 37° C. for 0.5 to 24 hours. It is preferable to remove unreacted test substance and control material by washing with a buffer such as PBS after the incubation step.

In the labeled nucleic acid contacting step, a labeled nucleic acid is brought into contact with the immobilized HMGB protein after the incubation step. The labeled nucleic acid is not particularly limited, and examples thereof include synthetic nucleic acids such as CpG ODN, poly(I:C), poly (U), B-DNA, 5'-triphosphorylated RNA and micro RNA; viral DNA such as HSV-1 and vaccinia virus DNA; microbial DNA; and bovine thymus DNA. However, a synthetic nucleic acid is more preferable because of its higher homogeneity. The synthetic nucleic acid is preferably a 10- to 100-mer and more preferably a 15- to 25-mer. In the case where the HMGB protein is HMGB1, the labeled nucleic acid may be an RNA. The labeling is not particularly limited and may be performed with, for example, biotin, a fluorescent dye such as FITC, digoxigenin, or a radioisotope. It is preferable to remove unreacted labeled nucleic acid by washing with a buffer such as PBS after the labeled nucleic acid contacting step. Here, the test substance added in the incubation step may inhibit the labeled nucleic acid from binding to the HMGB protein, and the test substance that performs such inhibition is an inhibitor of activation of an immune response mediated by the HMGB protein.

In the quantifying step, the labeled nucleic acid bound to the immobilized HMGB protein is quantified. The method for the quantification of the labeled nucleic acid is not particularly limited. For example, in the case where the labeled nucleic acid is labeled with biotin, an anti-biotin antibody labeled with, for example, horse radish peroxidase (HRP) or alkaline phosphatase (AP) is reacted with the biotin, the unreacted antibody is washed out, and then a substrate corresponding to the enzyme such as the HRP or the AP bound to the antibody is reacted to give light emission or color development. The resulting light emission or color development is quantified using a plate reader or the like.

Alternatively, in the case where the labeled nucleic acid is labeled with biotin, streptavidin labeled with HRP or AP may be used in place of the anti-biotin antibody.

For example, in the case where the labeled nucleic acid is labeled with FITC, the labeled nucleic acid may be quantified by reacting an anti-FITC antibody or may be quantified by irradiating the FITC of the labeled nucleic acid with exciting light and measuring the generated fluorescence with a fluorescence plate reader or the like.

For example, in the case where the labeled nucleic acid is labeled with a radioisotope, the labeled nucleic acid may be quantified using a microplate scintillation counter or the like.

In the determination step, the amount of the labeled nucleic acid bound to the immobilized HMGB protein on which the incubation step is performed in the presence of the test substance and the amount of the labeled nucleic acid bound to the immobilized HMGB protein on which the incubation step is performed in the absence of the test substance are compared to each other, and the test substance is determined as an inhibitor of activation of an immune response mediated by the HMGB protein when the amount of the labeled nucleic acid bound to the immobilized HMGB protein on which the incubation step is performed in the presence of the test substance is less than the amount of the labeled nucleic acid bound to the immobilized HMGB protein on which the incubation step is performed in the absence of the test substance. Alternatively, the test substance is determined as an enhancer of activation of an immune response mediated by the HMGB protein when the amount of the labeled nucleic acid bound to the immobilized HMGB protein on which the incubation step is performed in the presence of the test substance is higher than the amount of the labeled nucleic acid bound to the immobilized HMGB protein on which the incubation step is performed in the absence of the test substance.

Figure 44:
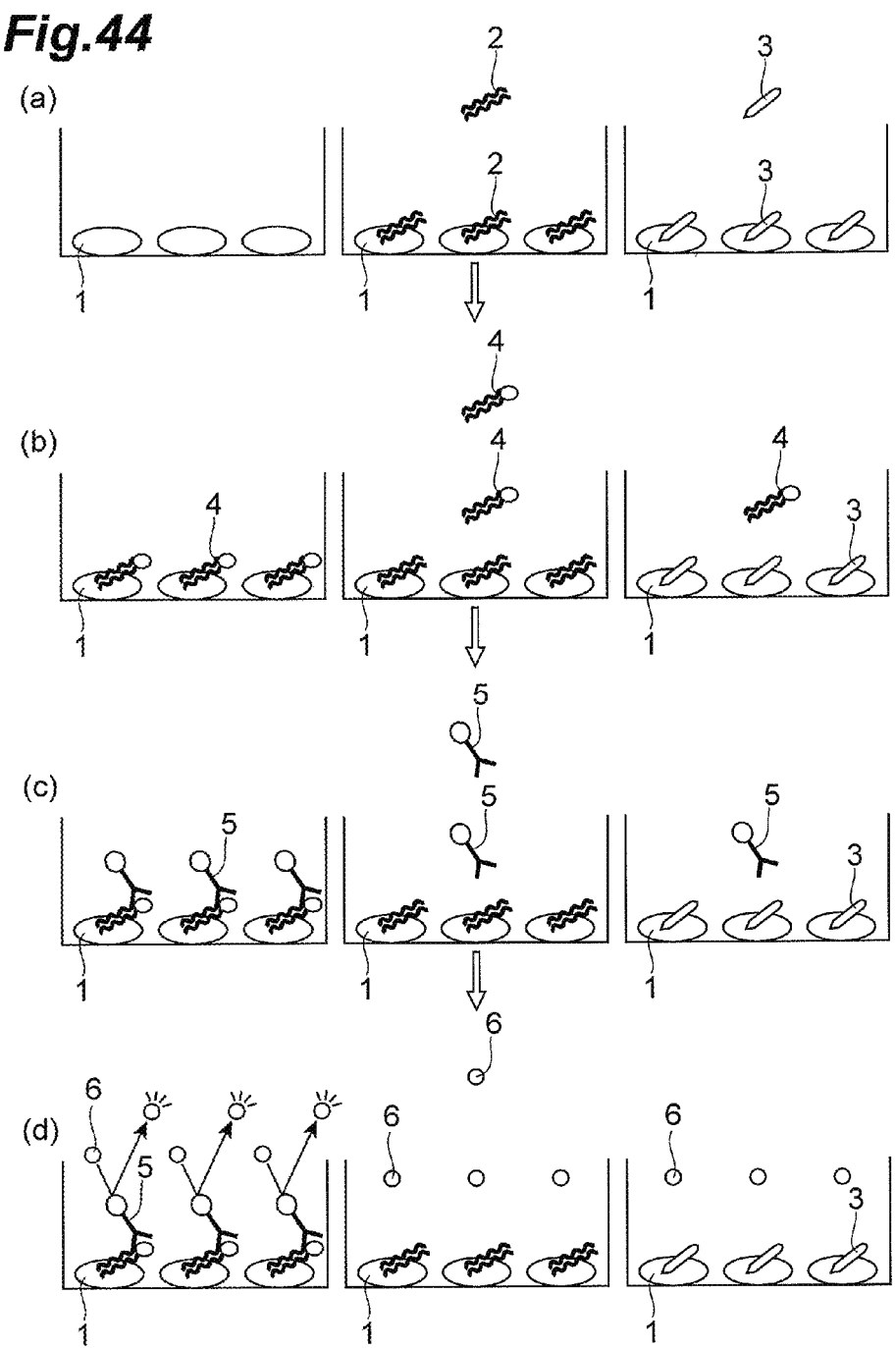
FIG. 44 shows diagrams illustrating an aspect of a method of screening for an inhibitor of activation of an immune response mediated by an HMGB protein.

FIG. 44 shows an aspect of a method of screening for an inhibitor or enhancer of activation of an immune response mediated by an HMGB protein. In the incubation step (FIG. 44a), an immobilized HMGB protein 1 is left in the presence or absence of a test substance 3 or in the presence of a positive control material 2. Subsequently, in the labeled nucleic acid contacting step (FIG. 44b), a biotin-labeled B-DNA 4 is brought into contact. Subsequently, in the quantifying step (FIGS. 44c and 44d), the biotin-labeled B-DNA 4 bound to the immobilized HMGB protein 1 is quantified. In FIG. 44c, an enzyme-labeled anti-biotin antibody 5 is reacted. Subsequently, a substrate 6 of the enzyme is added (FIG. 44d), and the light emission or color development is quantified using a plate reader or the like. In the sample on which the incubation step is performed in the absence of the test substance 3 (negative control), the labeled nucleic acid binds to the immobilized HMGB protein 1. In contrast, in the sample on which the incubation step is performed in the presence of the positive control material 2, the binding of the labeled nucleic acid to the immobilized HMGB protein 1 is inhibited. In the case of the test substance 3 in FIG. 44, in the sample on which the incubation step is performed in the presence of the test substance 3, the binding of the biotin-labeled B-DNA 4 (labeled nucleic acid) to the immobilized HMGB protein 1 is inhibited. In addition, since the amount of the biotin-labeled B-DNA 4 bound to the immobilized HMGB protein 1 on which the incubation step is performed in the presence of the test substance 3 is less than the amount of the biotin-labeled B-DNA 4 bound to the immobilized HMGB protein 1 on which the incubation step is performed in the absence of the test substance 3, the test substance 3 is determined as an inhibitor of activation of an immune response mediated by the HMGB protein.

A third embodiment of the method of screening for an inhibitor or enhancer of activation of an immune response mediated by an HMGB protein includes a contacting step of contacting an HMGB protein with an immobilized nucleic acid in the presence and absence of a test substance; a quantifying step of quantifying the HMGB protein bound to the immobilized nucleic acid; and a determination step of determining the test substance as an inhibitor of activation of an immune response mediated by the HMGB protein when the amount of the HMGB protein bound to the immobilized nucleic acid in the presence of the test substance is less than the amount of the HMGB protein bound to the immobilized nucleic acid in the absence of the test substance and determining the test substance as an enhancer of activation of an immune response mediated by the HMGB protein when the amount of the HMGB protein bound to the immobilized nucleic acid in the presence of the test substance is higher than the amount of the HMGB protein bound to the immobilized nucleic acid in the absence of the test substance.

It is possible by this screening method to perform more simply and efficiently screening for an inhibitor or enhancer of activation of an immune response mediated by an HMGB protein.

In the contacting step, an HMGB protein is brought into contact with an immobilized nucleic acid in the presence and absence of a test substance. As the nucleic acid, for example, a phosphorothioate oligonucleotide consisting of the nucleotide sequence as set forth in SEQ ID NO: 40 can be used. The method of immobilizing the nucleic acid is not particularly limited and can be performed by, for example, binding the nucleic acid labeled with biotin to a multi-well plate coated with streptavidin. As the HMGB protein, any of the recombinants of HMGB1, 2 and 3 can be suitably used.

The test substance is not particularly limited as long as it does not activate any immune response when animal cells, including human cells, are stimulated with the test substance only, and a nucleic acid, a nucleic acid analogue, a protein, a low molecular compound, etc. can be used. As the solvent for the test substance, a buffer such as PBS can be used. It is preferable that the concentration of the test substance in the contacting step is 0.1 to 100 μM. It is preferable that the contacting step is performed at 4 to 37° C. for 0.5 to 24 hours. It is preferable to remove unreacted test substance and control material by washing with a buffer such as PBS after the contacting step. The test substance added in the contacting step may inhibit the binding between the nucleic acid and the HMGB protein, and the test substance that performs such inhibition is an inhibitor of activation of an immune response mediated by the HMGB protein.

In the quantifying step, the HMGB protein bound to the immobilized nucleic acid is quantified. The method of quantifying the labeled nucleic acid is not particularly limited. For example, the HMGB protein is labeled with a fluorescent material in advance, and the fluorescence can be quantified. Alternatively, the HMGB protein may be quantified using an antibody against the HMGB protein.

In the determination step, the amount of the HMGB protein bound to the immobilized nucleic acid in the presence of the test substance and the amount of the HMGB protein bound to the immobilized nucleic acid in the absence of the test substance are compared to each other, and the test substance is determined as an inhibitor of activation of an immune response mediated by the HMGB protein when the amount of the HMGB protein bound to the immobilized nucleic acid in the presence of the test substance is less than the amount of the HMGB protein bound to the immobilized nucleic acid in the absence of the test substance. Alternatively, the test substance is determined as an enhancer of activation of an immune response mediated by the HMGB protein when the amount of the HMGB protein bound to the immobilized nucleic acid in the presence of the test substance is higher than the amount of the HMGB protein bound to the immobilized nucleic acid in the absence of the test substance.

The enhancer of activation of an immune response mediated by an HMGB protein obtained by the above-described screening methods can be used for the purpose of, for example, activating a defense mechanism against infection of a virus, a microorganism, a parasite, or the like; enhancing an anti-virus activity; remedying allergy symptoms by controlling the balance of immune cell differentiation; and activating antitumor response. These immune responses are examples of having advantageous effects.

EXAMPLES

Pull-Down Assay

Prior to mass spectrometry, mouse embryonic fibroblasts (MEFs) were stimulated with poly(dA:dT)•(dT:dA) (B-DNA, 10 μg/mL) for 4 hours. After the stimulation, the cells were homogenized in a homogenization buffer (20 mM HEPES, pH 7.4, 20% glycerol, 50 mM KCl, 2 mM $MgCl_2$, 1 mM PMSF, 10 μg/mL aprotinin, 10 μg/mL leupeptin) using a dounce homogenizer (Wheaton Science Products). A cytoplasmic protein extract was prepared by centrifuging the homogenized sample at 14500 rpm for 30 minutes. The cytoplasmic protein extract was incubated together with 1.4 μg/mL of B-DNA labeled with biotin at the 5' end, and then streptavidin-bound magnetic beads (Invitrogen Corporation) were added thereto, followed by incubation at 4° C. for 15 minutes. Pulled down sample was reacted with DNase I (Invitrogen Corporation) in a reaction buffer (20 mM Tris-Cl, pH 8.4, 20 mM $MgCl_2$, 50 mM KCl), and the supernatant was subjected to silver staining (Invitrogen Corporation) or mass spectrometry.

In vitro pull-down assay was carried out as follows. At first, a recombinant of HMGB1, 2, or 3 was treated in the presence or absence of a competitor at room temperature for 30 minutes. The supernatant was mixed with a biotin-labeled B-DNA at 4° C. for 30 minutes, then streptavidin-bound magnetic beads (Invitrogen Corporation) were added thereto, and the mixture was incubated in a binding buffer (50 mM Tris-Cl, pH 7.5, 150 mM NaCl, 1 mM EDTA, 1% NP-40, 100 μg/mL leupeptin, 1 mM PMSF, 1 mM $Na_3VO_4$). Subsequently, the mixture was sufficiently washed with a binding buffer, was separated by SDS-PAGE, and then was immunoblotted using an anti-HMGB1, 2, or 3 antibody.

(Mouse, Cell and Reagent)

Mice having C57BL/6 genetic background were used, except for Tlr9−/− mice, which have Balb/c genetic background. $Tlr9^{-/-}$, $Hmgb1^{-/-}$ and $Hmgb2^{-/-}$ mice were produced by conventional methods. MEFs, RAW264.7, NIH3T3, HEK293T cells, cDCs (conventional dendritic cells) and pDCs (plasmacytoid dendritic cell precursors) derived from the bone marrow of $Tlr9^{-/-}$ mice were maintained by conventional methods. $Hmgb1^{-/-}$ macrophages, cDCs and pDCs were prepared by culturing fetal liver hematopoietic progenitor cells (differentiation marker-free cells purified by a MACS Lineage depletion kit of Miltenyi Biotec GmbH) in the presence of SCF (20 ng/mL), IL-3 (10 ng/mL), and IL-6 (10 ng/mL) for 2 days and then in the presence of 20 ng/mL of M-CSF (microphage), 20 ng/mL of GM-CSF (cDCs) and 100 ng/mL of human Flt3L (pDCs) for 6 days. SCF, IL-3 and IL-6 were purchased from PeproTech Inc. IFN-γ and TNF-α were purchased from R&D systems, Inc. IFN-β was kindly provided by Toray Industries, Inc. B-DNA and bovine thymus DNA were purchased from Sigma-Aldrich Corporation. Biotin-labeled poly(dA:dT)•(dT:dA) was purchased from Hokkaido System Science Co., Ltd. ISD (IFN-stimulatory DNA), CpG ODN, FITC-labeled base-free phosphorothioate deoxyribose homopolymer (PS, 20-mer) and FITC-labeled base-free natural deoxyribose homopolymer (PD, 20-mer) were purchased from Fasmac Co., Ltd. PD is one where the phosphorothioate linkage of PS is converted into phosphodiester linkage. Purified vaccinia virus DNA (MO strain) was provided by A. Kato and M. Kidokoro. HSV DNA was kindly provided by Y. Kawaguchi. 5'-triphosphate RNA was provided by C. Reis e Sousa and J. Rehwinkel. Escherichia coli DNA (microbial DNA) and R837 were purchased from InvivoGen. Poly(U) and lipopolysaccharide (LPS) were purchased from Sigma-Aldrich Corporation. Poly(I:C) was purchased from GE Healthcare Bio-Sciences AB. B-DNA, poly(I:C) and other nucleic acid ligands were each used at a concentration of 10 μg/mL unless otherwise specified. The complex formation of CpG-A ODN and DOTAP (F. Hoffmann-La Roche Ltd.) was performed by a conventional method. MitoTracker Deep Red 633 was purchased from Invitrogen Corporation. Anti-HMGB1 antibody and anti-HMGB2 antibody were purchased from Abcam plc. Anti-HMGB3 antibody was purchased from Trans Genic Inc. Anti-IRF3 antibody (ZM3) was purchased from Zymed Laboratories Inc. Anti-β-actin antibody (AC-15) was purchased from Sigma-Aldrich Corporation. Anti-NF-κB p65 antibody (C20) was purchased from Santa Cruz Biotechnology, Inc. Anti-phosphorylated STAT1 antibody (58D6) was purchased from Cell Signaling Technology, Inc.

(Plasmid Construction)

Mouse HMGB cDNA was obtained by RT-PCR of total RNA derived from MEFs and was cloned into the Sal I and Not I sites of pGEX4T3 vector (GE Healthcare Bio-Sciences AB). Glutathione S-transferase (GST)-tagged HMGB protein was purified using glutathione sepharose beads (GE Healthcare Bio-Sciences AB). HMGB protein and GST protein were separated by thrombin protease (Novagen) treatment.

The cDNAs of mouse RIG-I (SEQ ID NO: 3), HMGB1 (SEQ ID NO: 4) and Rab5 (SEQ ID NO: 5) were obtained by reverse transcription polymerase chain reaction (hereinafter, sometimes referred to as RT-PCR) for total RNA derived from MEFs and were cloned into XhoI and NotI recognition sites of pCAGGS-CFP, pCAGGS-YFP and pCAGGS-RFP vectors (see Proc. Natl. Acad. Sci. USA, 101, 15416-15421, 2004), respectively, to give CFP-RIG-I, YFP-HMGB1 and RFP-Rab5.

(Immunoblot Analysis)

Cytolysis and immunoblot analysis were performed by conventional methods. The IRF dimer was performed by native PAGE and subsequent immunoblot analysis using an anti-mouse IRF3 antibody. The quantitative measurement of IRF3 dimer was performed with NIH Image software. Similar results were obtained in each independent experiment performed three times.

(RNA Analysis)

RNA extraction and reverse transcription reaction were performed by conventional methods. Quantitative real-time RT-PCR analysis (quantitative RT-PCR) was performed using LightCycler 480 (trade name, F. Hoffmann-La Roche Ltd.) and SYBR Green system (F. Hoffmann-La Roche Ltd.). All data were shown with a relative expression unit standardized using the results obtained for a glyceraldehyde triphosphate dehydrogenase (GAPDH) gene. The data were shown as mean±standard deviation of triplicate measurements. Regarding all data, similar results were obtained in each independent experiment performed at least twice.

Primer sequences for quantitative RT-PCR were as follows: HMGB1 sense: 5'-CCAAAGGGGAGACCAAAAAG-3' (SEQ ID NO: 6), HMGB1 antisense: 5'-TCATAGGGCT-GCTTGTCATCT-3' (SEQ ID NO: 7), HMGB2 sense: 5'-TGCCTTCTTCCTGTTTTGCT-3' (SEQ ID NO: 8), HMGB2 antisense: 5'-GGACCCTTCTTTCCTGCTTC-3' (SEQ ID NO: 9), HMGB3 sense: 5'-GGAGATGAAAGAT-TATGGACCAG-3' (SEQ ID NO: 10), HMGB3 antisense: 5'-CTTTGCTGCCTTGGTG-3' (SEQ ID NO: 11), GBP1 sense: 5'-CTCAGCAGCAGTGCAAAAGG-3' (SEQ ID NO: 12), GBP1 antisense: 5'-GCTCCTGGAGGGTTTCTGTG-3' (SEQ ID NO: 13), IRF7 sense: 5'-GCAAGGGTCACCA-CACTA-3' (SEQ ID NO: 14), IRF7 antisense: 5'-CAAGCA-CAAGCCGAGACT-3' (SEQ ID NO: 15), IL-12p40 sense: 5'-GACACGCCTGAAGAAGATGAC-3' (SEQ ID NO: 16), IL-12p40 antisense: 5'-TAGTCCCTTTGGTCCAGTGTG-3' (SEQ ID NO: 17), GAPDH sense: 5'-CTCATGACCA-CAGTCCATGC-3' (SEQ ID NO: 18), GAPDH antisense: 5'-CACATTGGGGGTAGGAACAC-3' (SEQ ID NO: 19), IL-6 sense: 5'-ATGAAGTTCCTCTCTGCAAGAGACT-3' (SEQ ID NO: 20), IL-6 antisense: 5'-CACTAGGTTTGC-CGAGTAGATCTC-3' (SEQ ID NO: 21), RANTES sense: 5'-ACGTCAAGGAGTATTTCTACAC-3' (SEQ ID NO: 22), RANTES antisense: 5'-GATGTATTCTTGAACCCACT-3' (SEQ ID NO: 23), IκB-α sense: 5'-TTGGTGACTTTGGGT-GCT-3' (SEQ ID NO: 24), IκB-α antisense: 5'-TGACAT-CAGCCCCACATTT-3' (SEQ ID NO: 25), IFN-α1 sense: 5'-GCCTTGACACTCCTGGTACAAATGAG-3' (SEQ ID NO: 26), IFN-α1 antisense: 5'-CAGCACATTGGCAGAG-GAAGACAG-3' (SEQ ID NO: 27), IFN-α4 sense: 5'-GAC-GACAGCCAAAGAAGTGA-3' (SEQ ID NO: 28), IFN-α4 antisense: 5'-GAGCTATGTCTTGGCCTTCC-3' (SEQ ID NO: 29), IFN-β sense: 5'-CCACCACAGCCCTCTCCAT-CAACTAT-3' (SEQ ID NO: 30) and IFN-β antisense: 5'-CAAGTGGAGAGCAGTTGAGGACATC-3' (SEQ ID NO: 31).

However, the nucleotide sequences of primers used in the quantitative RT-PCR in Examples 50, 54 and 56 were as follows: Ifna4 forward chain (Fw): 5'-CAATGACCT-CAAAGCCTGTGTG-3' (SEQ ID NO: 47), Ifna4 reverse chain (Rv): 5'-CACAGTGATCCTGTGGAAGT-3' (SEQ ID NO: 48), Ifnb1 (Fw): 5'-CCACCACAGCCCTCTCCAT-CAACTAT-3' (SEQ ID NO: 49), Ifnb1 (Rv): 5'-CAAGTG-GAGAGCAGTTGAGGACATC-3' (SEQ ID NO: 50), 116 (Fw): 5'-ACGATGATGCACTTGCAGAA-3' (SEQ ID NO: 51), 116 (Rv): 5'-GTAGCTATGGTACTCCAGAAGAC-3' (SEQ ID NO: 52), Tnfa (Fw): 5'-TCATACCAG-GAGAAAGTCAACCTC-3' (SEQ ID NO: 53), Tnfa (Rv): 5'-GTATATGGGCTCATACCAGGGTTT-3' (SEQ ID NO: 54), Ccl5 (RANTES) (Fw): 5'-ACGTCAAGGAGTATTTC-TACAC-3' (SEQ ID NO: 22), Ccl5 (RANTES) (Rv): 5'-GAT-GTATTCTTGAACCCACT-3' (SEQ ID NO: 23), Gapdh (Fw): 5'-CTCATGACCACAGTCCATGC-3' (SEQ ID NO: 18) and Gapdh (Rv): 5'-CACATTGGGGGTAGGAACAC-3' (SEQ ID NO: 19).

(Statistical Analysis)

The results of control groups and test groups were evaluated by Student's t-test.

(ELISA)

Mouse IFN-β, IL-6 and IL-1β were measured by ELISA. The IFN-β ELISA kit was purchased from PBL Interferon Source. The IL-6 and IL-1β ELISA kits were purchased from R&D systems, Inc. Regarding all data, similar results were obtained in an additional independent test performed twice.

(RNA Interference)

The siRNA vector was constructed by inserting an oligonucleotide into EcoRI and HindIII sites of a pSUPER.retro.puro retrovirus vector. The target sequences of siRNA of mouse HMGB1, 2 and 3 (pan-HMGB-siRNA, hereinafter, sometimes referred to as HMBG-si); HMGB2; and Renilla luciferase (control, hereinafter, sometimes referred to as Ctrl-si) were respectively 5'-GTATGAGAAGGATATTGCT-3' (SEQ ID NO: 32), 5'-GCGTTACGAGAAACCAGTT-3' (SEQ ID NO: 33) and 5'-GTAGCGCGGTGTATTATACA-3' (SEQ ID NO: 34). The MEFs and RAW264.7 cells into which genes have been introduced were respectively selected with 2 µg/mL of puromycin (Sigma-Aldrich Corporation) and 4 µg/mL of puromycin for 48 hours.

Electrophoretic Mobility Shift Assay (EMSA)

EMSA was performed by a conventional method. The consensus sequence (5'-TCGACCCGGGACTTTCCGCCGG-GACTTTCCGCCGGGACTT TCCGG-3', SEQ ID NO: 35) of NF-κB was used. The presence of p65 present in a NF-κB-DNA complex was confirmed by detection of a super-shift band using an anti-p65 antibody.

(Virus Infection)

Cells were infected with HSV-1 or VSV at an MOI (multiplicity of infection) of 1.0 for 12 hours. In the measurement of the yields of HSV-1 and VSV, plaque formation assay was performed by a conventional method. Regarding all data, similar results were obtained in an additional independent test performed twice. The viruses were prepared by a conventional method.

(Fluorescence Microscopic Observation)

HeLa cells ($5 \times 10^4$ cells) were cultured on a 35-mm tissue culture dish having a glass bottom (Matsunami Glass Ind., Ltd.). The fluorescence microscopic observation was performed using a laser scanning confocal microscope IX81 (Olympus Corporation). Double and triple color images were photographed with a continuous shooting mode to prevent cross excitation.

(Oligonucleotide)

CpG-B (SEQ ID NO: 37, hereinafter, sometimes expressed as "CpG-B(S)"), CpG-Rev (SEQ ID NO: 38, hereinafter, sometimes expressed as "CpG-Rev(S)") and CpG-M (SEQ ID NO: 39, hereinafter, sometimes expressed as "CpG-M(S)"), which are phosphorothioate oligonucleotide and PS were used. The nucleotide sequences of these compounds are shown in FIG. 46. In FIG. 46, underlined CG (CpG-B(S)), GC (CpG-Rev(S)) and GG (CpG-M(S)) are characteristic nucleotide sequences in the respective phosphorothioate oligonucleotides. In addition to the above, the following phosphorothioate oligonucleotides: CpG ODN 1018(S): 5'-TGACTGTGAACGTTCGAGATGA-3' (SEQ ID NO: 55) and ODN 1019(S): 5'-TGACTGTGAAGGTTA-GAGATGA-3' (SEQ ID NO: 56) were also used. In addition, the following oligonucleotide: CpG-A: 5'-ggTGCATCGAT-GCAgggggG-3' (SEQ ID NO: 2) was used. In CpG-A, the nucleotides represented by small letters have phosphorothioate backbones and the nucleotides represented by capital letters have phosphodiester backbones.

(Preparation of Mouse Splenocytes)

The spleen of C57BL/6J mice was removed and was injected with PBS containing DNase I collagenase D using a 25G needle (Nipro Corporation), and the exuded cell suspension was collected. Furthermore, the spleen was chopped in a new PBS containing DNase I collagenase D, was collected, and was incubated (for 30 minutes) at 37° C. The both were filtered through a cell strainer (mesh size: 40 μm, Becton, Dickinson and Company), were washed with PFE (prepared by adding 1 mM of EDTA (Gibco Corporation) and 2% FCS (HyClone Laboratories Inc.) to PBS (Invitrogen Corporation), pH 7.2), and were then suspended in 1×RBC Lysis Buffer (eBioscience, Inc.) to hemolyze erythrocytes. The resulting cells were further washed with PFE twice, were then filtered through a cell strainer (mesh size: 40 μm, Becton, Dickinson and Company) again, and were suspended in an RPMI medium.

(Analysis of Activation of Signaling Pathway by Western Blotting)

In Example 53, the following antibodies were used as primary antibodies: rabbit anti-IRF3 polyclonal antibody (Invitrogen Corporation), rabbit anti-phosphorylated IRF3 (Ser396) (4D4G) antibody (Cell Signaling Technology, Inc.), mouse anti-IκBα (L35A5) antibody (Cell Signaling Technology, Inc.), rabbit anti-phosphorylated IκBα (Ser32) (14D4) antibody (Cell Signaling Technology, Inc.), rabbit anti-JNK antibody (Cell Signaling Technology, Inc.), rabbit anti-phosphorylated JNK (Thr183/Tyr185) (81E11) antibody (Cell Signaling Technology, Inc.), rabbit anti-p38 MAP kinase antibody (Cell Signaling Technology, Inc.) and rabbit anti-phosphorylated p38 MAP kinase (Thr180/Tyr182) antibody (Cell Signaling Technology, Inc.). In addition, the following antibodies were used as secondary antibodies: anti-rabbit IgG HRP-bound antibody (GE Healthcare UK Ltd.) and anti-mouse IgG HRP-bound antibody (GE Healthcare UK Ltd.).

Role of HMGB in Immune Response Activated by Cytoplasmic DNA or RNA

Example 1

Hmgb1$^{+/+}$ MEFs or Hmgb1$^{-/-}$ MEFs were stimulated with B-DNA (FIG. 1*a*) or poly(I:C) (FIG. 1*b*) for 6 hours or with lipopolysaccharide (LPS) (200 ng/mL) (FIG. 1*c*) for 2 hours. The induction levels of IFN-β mRNA were measured by quantitative RT-PCR. The results are shown in FIG. 1. The symbol "*" indicates p<0.01 in comparison with Hmgb1$^{+/+}$ MEFs. All data were shown as mean±standard deviation (n=3). ND means not detected.

In Hmgb1$^{-/-}$ MEFs, the IFN-β induction by delivery of DNA or RNA to cytoplasms decreased.

Example 2

Figure 2:
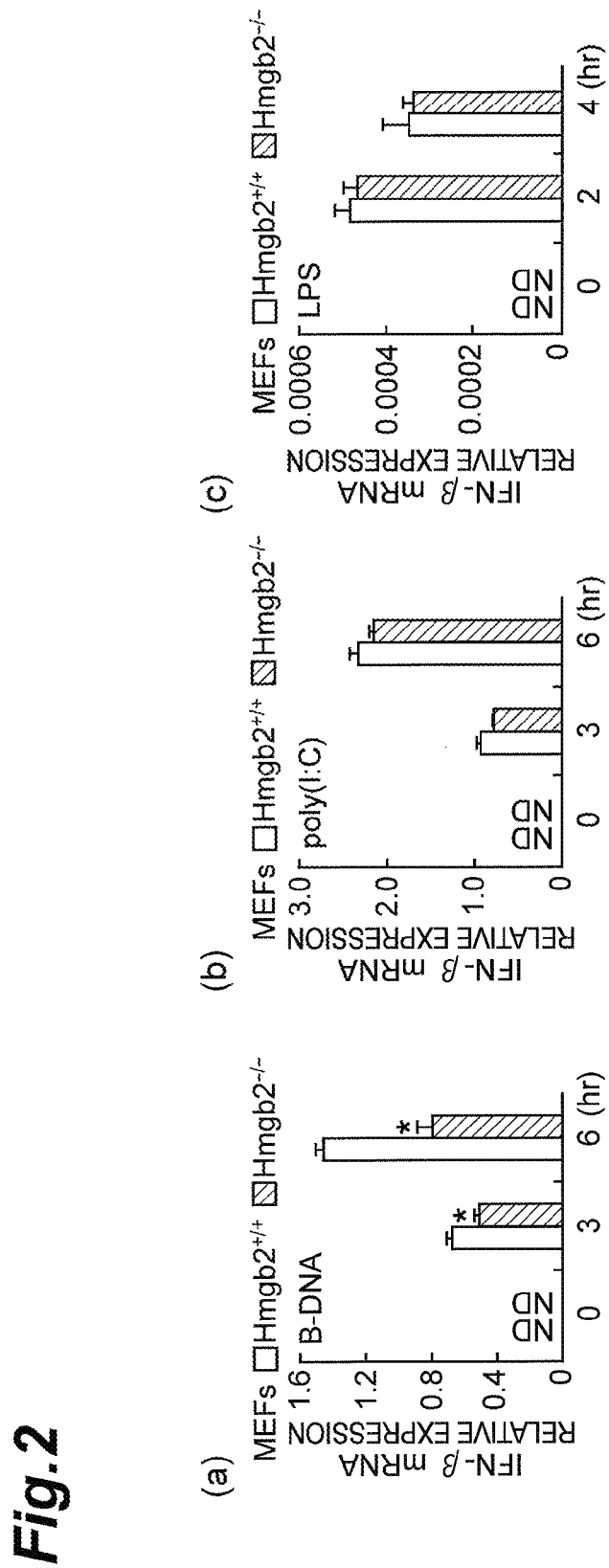
FIG. 2 is a set of graphs showing the results of Example 2.

Hmgb2$^{+/+}$ MEFs or Hmgb2$^{-/-}$ MEFs were stimulated with B-DNA (FIG. 2*a*) or poly(I:C) (FIG. 2*b*) for 6 hours or with LPS (200 ng/mL) (FIG. 2*c*) for 2 hours. The induction levels of IFN-β mRNA were measured by quantitative RT-PCR. The results are shown in FIG. 2. The symbol "*" indicates p<0.001 in comparison with Hmgb2$^{+/+}$ MEFs. All data were shown as mean±standard deviation (n=3). ND means not detected.

A decrease of IFN-β induction in Hmgb2$^{-/-}$ MEFs was observed by delivery of DNA to cytoplasms, but was not observed by delivery of RNA.

Example 3

Figure 3:
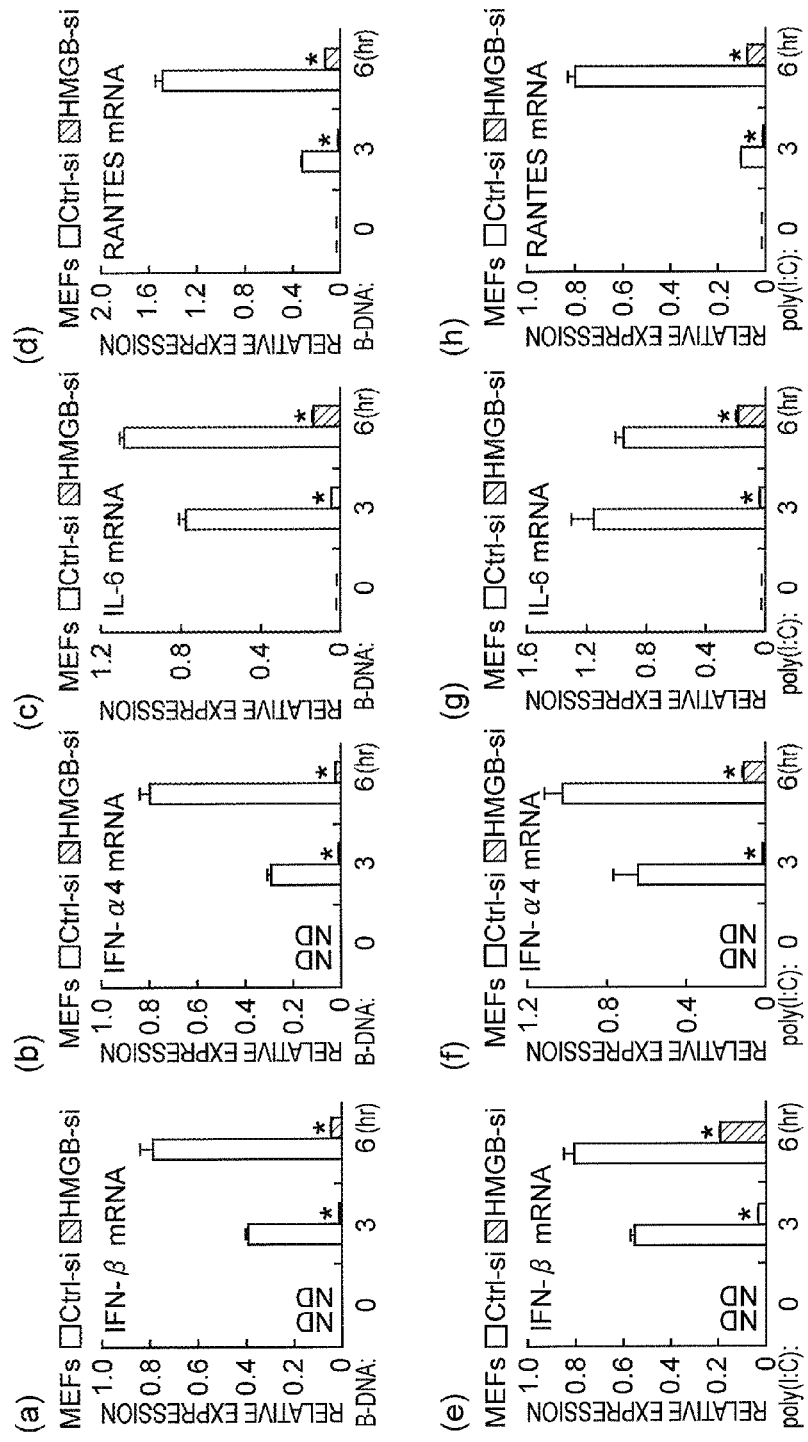
FIG. 3 is a set of graphs showing the results of Example 3.

B-DNA or poly(I:C) was lipotransfected (lipofection) into MEFs transformed with retrovirus expressing siRNA targeting all HMGBs (HMBG-si) or control siRNA (Ctrl-si). Subsequently, the expression levels of mRNAs of IFN-β (FIGS. 3*a* and *e*), IFN-α4 (FIGS. 3*b* and *f*), IL-6 (FIGS. 3*c* and *g*) and RANTES (FIGS. 3*d* and *h*) were measured by quantitative RT-PCR. The results are shown in FIG. 3. The symbol "*" indicates p<0.01 in comparison with Ctrl-si-MEF. All data were shown as mean±standard deviation (n=3). ND means not detected.

MEFs of which all HMGBs were deleted were deficient in immune response against cytoplasmic DNA or RNA.

Example 4

Figure 4:
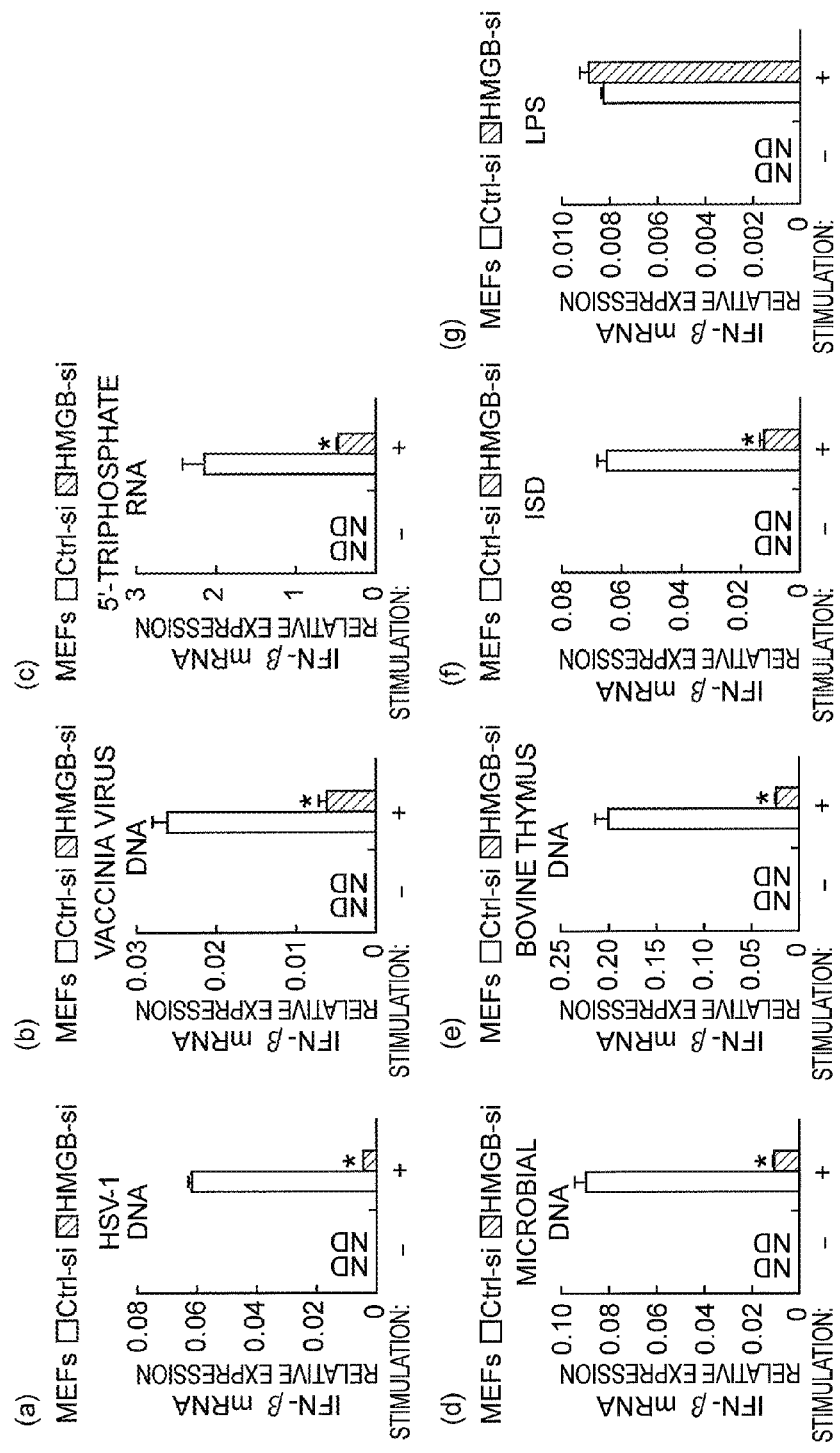
FIG. 4 is a set of graphs showing the results of Example 4.

Nucleic acids prepared from various supply sources, i.e., HSV-1 DNA (FIG. 4*a*), vaccinia virus DNA (FIG. 4*b*), 5'-triphosphate RNA (FIG. 4*c*), microbial DNA (FIG. 4*d*), bovine thymus DNA (FIG. 4*e*) and ISD (FIG. 4*f*), were lipotransfected into MEFs of which all HMGBs were deleted and were delivered to the cytoplasms. The nucleotide sequence of the ISD is 5'-TACAGATCTACTAGTGATCTATGACT-GATCTGTACATGATCTA CA-3' (SEQ ID NO: 36). Stimulation with LPS was also performed as a control (FIG. 4*g*). The expression levels of IFN-β mRNA at 6 hours after lipotransfection were measured by quantitative RT-PCR. The results are shown in FIG. 4. The symbol "*" indicates p<0.01 in comparison with Ctrl-si-MEF. All data were shown as mean±standard deviation (n=3). ND means not detected.

MEFs of which all HMGBs were deleted were stimulated with LPS (200 ng/mL) for 2 hours, and as a result, IFN-β was induced (FIG. 4*g*). In contrast, MEFs of which all HMGBs were deleted were deficient in IFN-β induction at 6 hours after delivery of nucleic acids prepared from various supply sources to cytoplasms (FIGS. 4*a* to *h*).

Activation of Signaling Pathway Mediated by Cytoplasmic Nucleic Acid Receptor and Necessity of HMGB in Anti-Virus Immune Response Example 5

B-DNA or poly(I:C) was lipotransfected (lipofection) into MEFs transformed with retrovirus expressing siRNA targeting all HMGBs (HMBG-si) or control siRNA (Ctrl-si).

Figure 5:
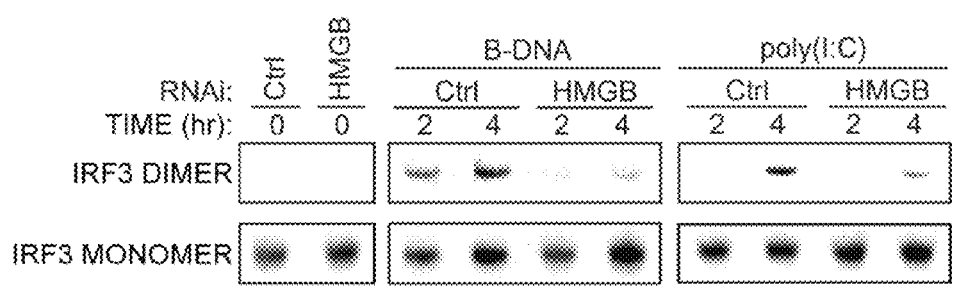
FIG. 5 is a set of photographs showing the results of Example 5.

Dimerization of IRF3 was evaluated by native PAGE and subsequent immunoblotting. The results are shown in FIG. 5.

Example 6

Figure 6:
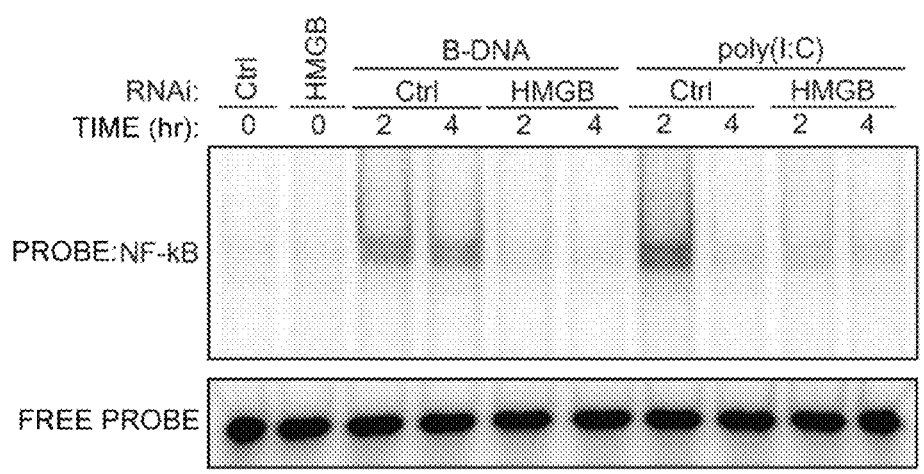
FIG. 6 is a set of photographs showing the results of Example 6.

B-DNA or poly(I:C) was lipotransfected (lipofection) into MEFs transformed with retrovirus expressing siRNA targeting all HMGBs (HMBG-si) or control siRNA (Ctrl-si). Activation of NF-κB was evaluated by EMSA. The results are shown in FIG. 6.

Example 7

Induction of type I IFN by virus infection was investigated. MEFs transformed with retrovirus expressing siRNA targeting all HMGBs (HMBG-si) or control siRNA (Ctrl-si) were infected with VSV or HSV-1. The expression levels of mRNAs of type I IFNs, i.e., IFN-β (FIGS. 7a and b), IFN-α1 (FIGS. 7c and d) and IFN-α4 (FIGS. 7e and f) were measured by quantitative RT-PCR. The results are shown in FIG. 7. All data were shown as mean±standard deviation (n=3). ND means not detected. The symbol "*" indicates $p<0.01$ in comparison with Ctrl-si-MEF and the symbol "**" indicates $p<0.05$ in comparison with Ctrl-si-MEF.

Example 8

It is known that in plasmacytoid dendritic cell precursors (pDCs), which are one of sub-sets of dendritic cells (DCs), production of a large amount of type I IFN is induced through TLR9. It has been reported that in pDCs derived from spleen, expression of type I IFN is induced through TLR9 by infection with herpes simplex virus type 1 (HSV-1), which is a DNA virus, but in pDCs and cDCs (conventional DCs) derived from bone marrow, a TLR9-independent pathway is also present in expression induction of type I IFN by HSV-I.

Figure 8:
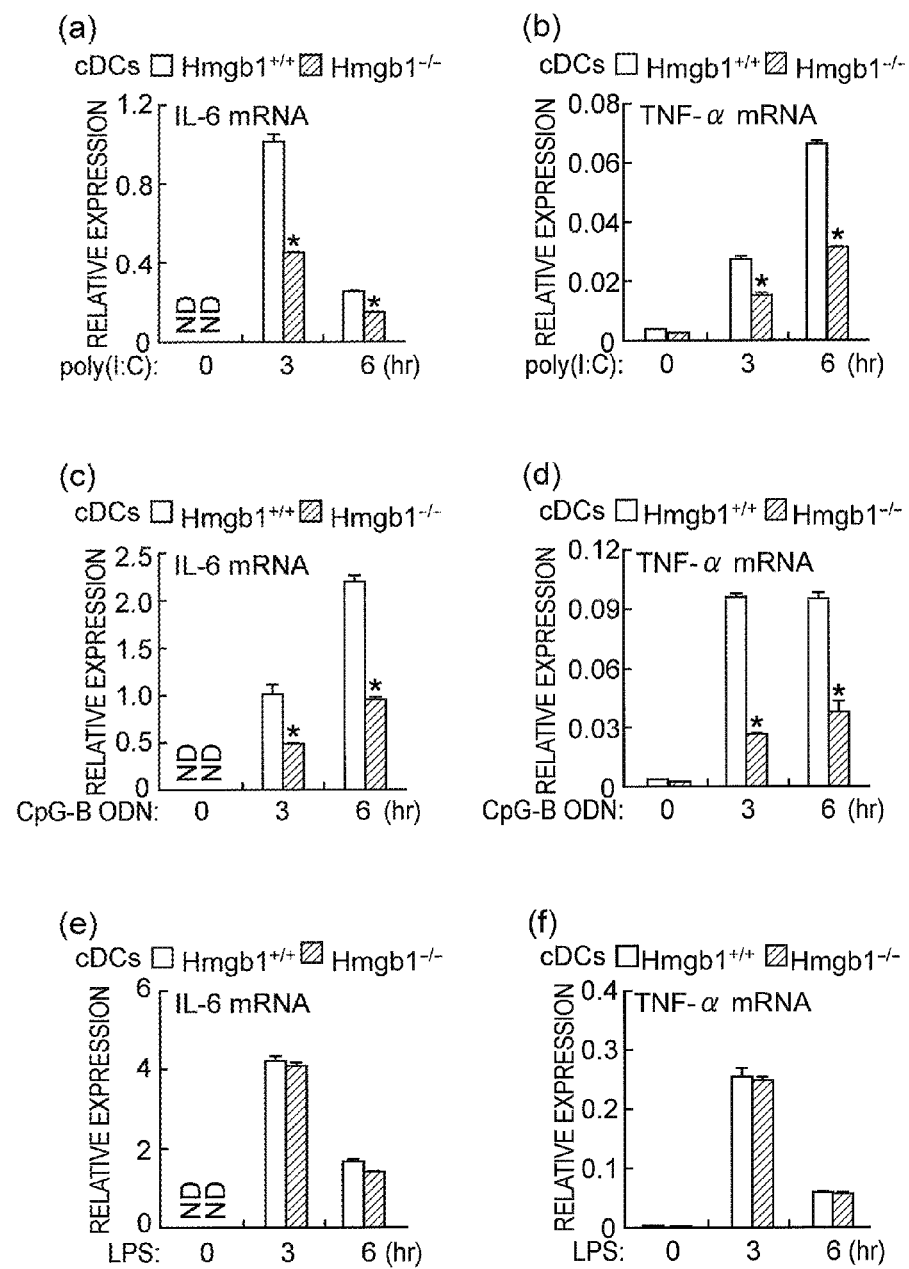
FIG. 8 is a set of graphs showing the results of Example 8.

Hmgb1$^{+/+}$ or Hmgb1$^{-/-}$ cDCs were stimulated with a TLR ligand, i.e., poly(I:C) (FIGS. 8a and b) or CpG-B ODN (FIGS. 8c and d). Stimulation with LPS was performed as a control (FIGS. 8e and f). Subsequently, the expression levels of mRNAs of IL-6 (FIGS. 8a, c and e) and TNF-α (FIGS. 8b, d and f) were measured by quantitative RT-PCR. The results are shown in FIG. 8. All data were shown as mean±standard deviation (n=3). ND means not detected. The symbol "*" indicates $p<0.01$ in comparison with wild-type cells.

Example 9

Figure 9:
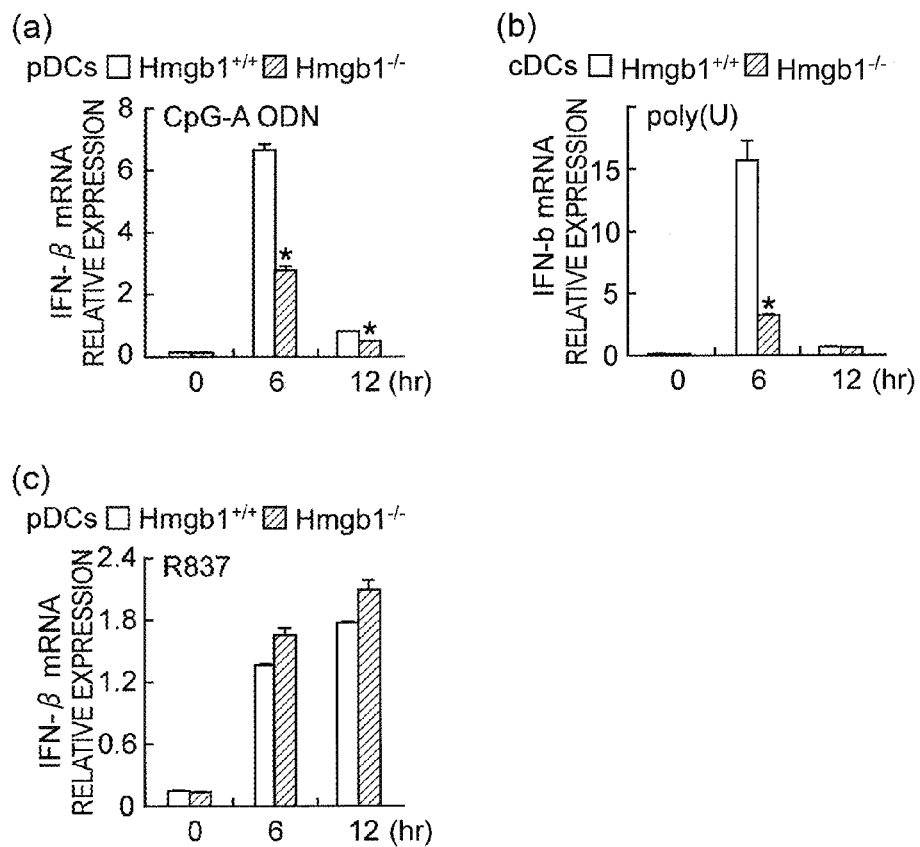
FIG. 9 is a set of graphs showing the results of Example 9.

Hmgb1$^{+/+}$ or Hmgb1$^{-/-}$ pDCs were stimulated with a TLR ligand, i.e., CpG-B ODN (FIG. 9a) or poly(U) (FIG. 9b). Stimulation with R837 (TLR7 agonist) was also performed as a control (FIG. 9c). Subsequently, the expression levels of mRNA of IFN-β were measured by quantitative RT-PCR. The results are sown in FIG. 9. All data were shown as mean±standard deviation (n=3). The symbol "*" indicates $p<0.01$ in comparison with wild-type cells.

Interference of Immune Response Activated by Nucleic Acid, Using HMGB-High-Binding Affinity Nucleic Acid Analogue

Example 10

MEFs are known that the expression level of TLR9 is low. MEFs pretreated with 1 μM of CpG-B ODN for 30 minutes or not pretreated were stimulated with delivery to cytoplasms of B-DNA (FIG. 10a), poly(I:C) (FIG. 10b), or LPS (FIG. 10c).

Figure 10:
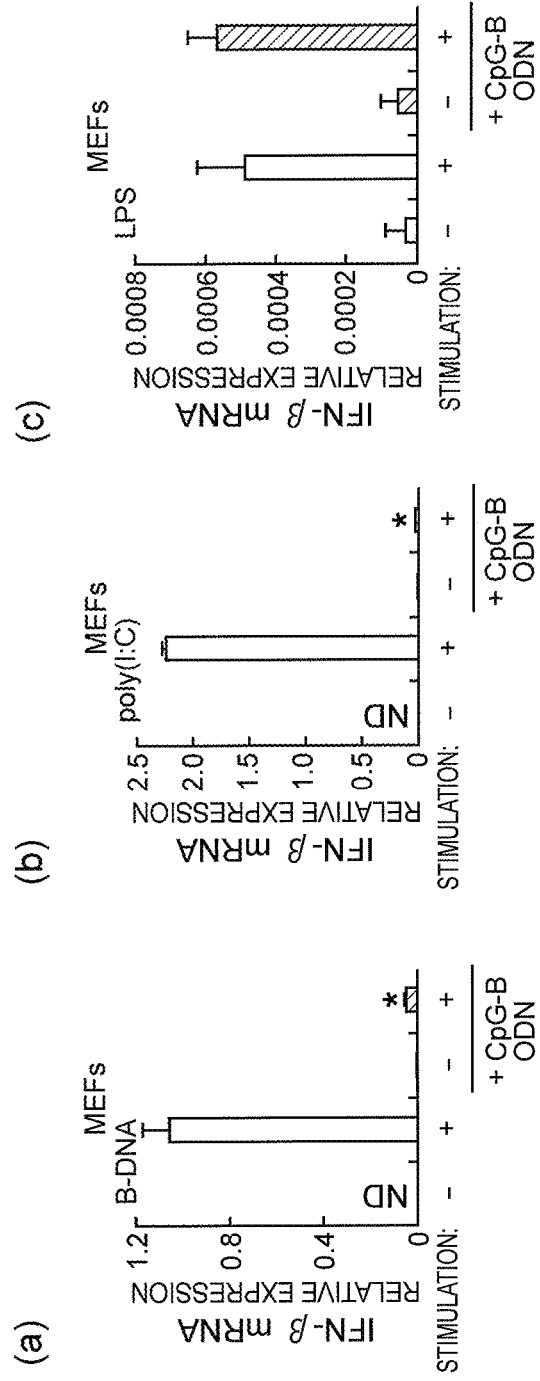
FIG. 10 is a set of graphs showing the results of Example 10.

The expression levels of IFN-β mRNA were measured by quantitative RT-PCR. The results are shown in FIG. 10. All data were shown as mean±standard deviation (n=3). ND means not detected. The symbol "*" indicates that the results of pretreated cells are $p<0.01$ with respect to the results of cells not subjected to the pretreatment.

Example 11

Figure 11:
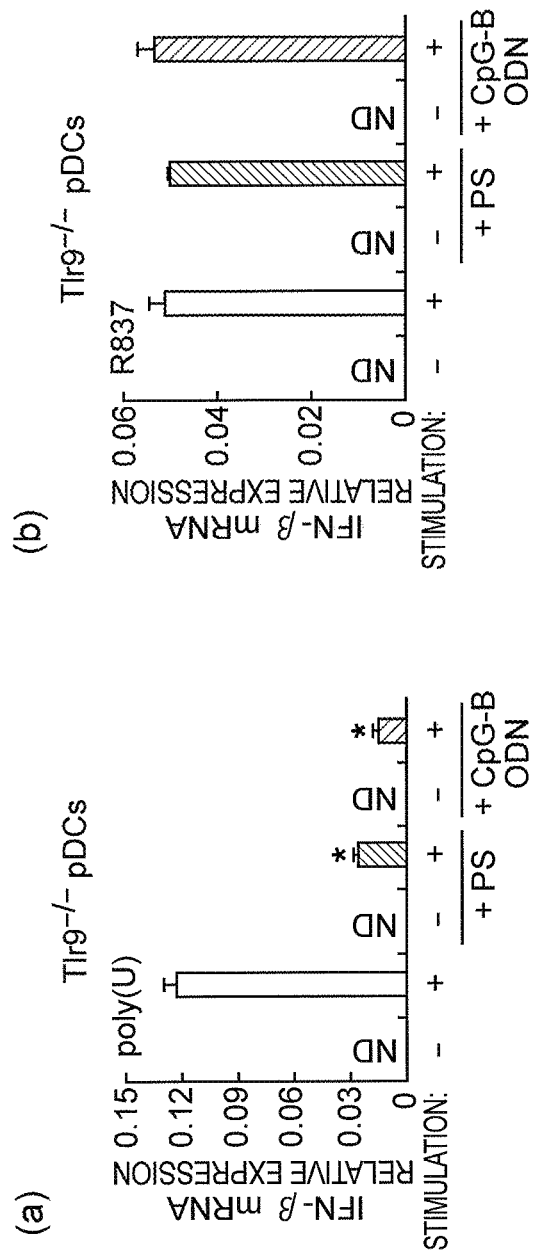
FIG. 11 is a set of graphs showing the results of Example 11.

Bone marrow-derived Tlr9$^{-/-}$ pDCs pretreated with 5 μM of PS or 1 μM of CpG-B ODN for 30 minutes or not pretreated were stimulated with lipotransfection of 1 μg/mL of poly(U) (FIG. 11a) or 25 μg/mL of R837 (FIG. 11b) for 8 hours. The expression of IFN-β mRNA was measured by quantitative RT-PCR. The results are shown in FIG. 11. The symbol "*" indicates that the results of pretreated cells are $p<0.01$ with respect to the results of cells not subjected to the pretreatment.

Identification of HMGB and its Binding to DNA and RNA

Example 12

Figure 12:
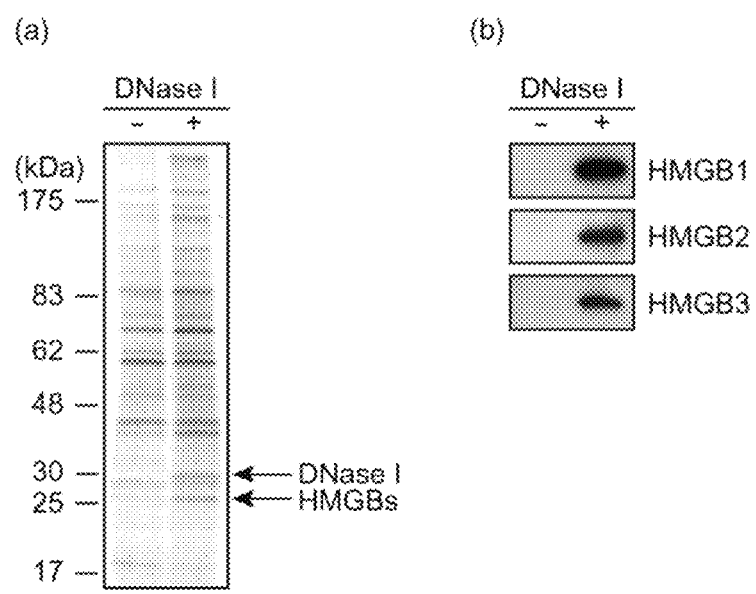
FIG. 12 is a set of photographs showing the results of Example 12.

HMGB was identified. Cytoplasmic extract of MEFs stimulated with B-DNA for 4 hours was subjected to a pull-down assay using biotin-bound B-DNA and streptavidin-bound magnetic beads. The protein bound to the B-DNA was eluted by DNase I treatment. The eluted protein was visualized by SDS-PAGE and subsequent silver staining (FIG. 12a) and was subsequently analyzed by mass spectrometry. FIG. 12a shows the results of the silver staining. FIG. 12b shows the results of immunoblot analysis using antibodies against HMGB1, 2 and 3.

Example 13

Figure 13:
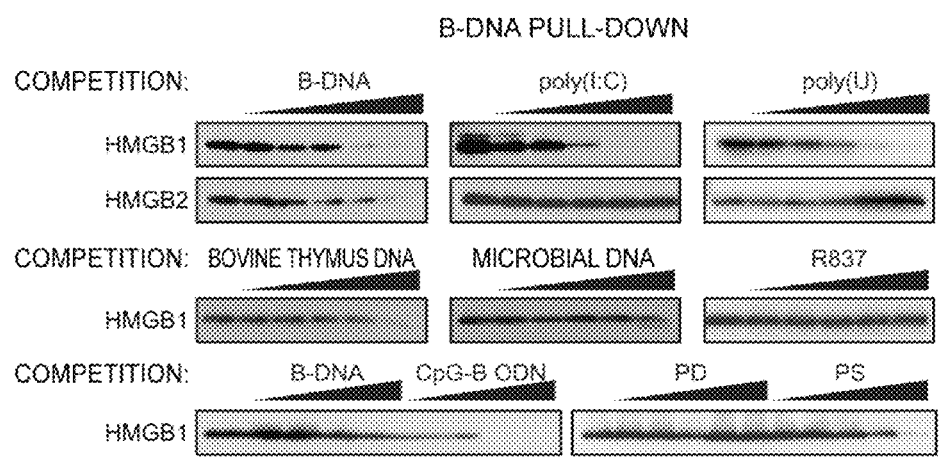
FIG. 13 is a set of photographs showing the results of Example 13.

Binding of HMGB to DNA, RNA and base-free phosphorothioate deoxyribose homopolymer (PS) was investigated. The results are shown in FIG. 13. In vitro pull-down assay using recombinant HMGB1 or 2 and biotin-bound B-DNA was performed in the presence of 1, 3, 10, 30 and 100 μg/mL of unlabeled nucleic acid (B-DNA, poly(I:C), poly(U), bovine thymus DNA, or microbial DNA), R837 (1, 3, 10, 30 and 100 μg/mL) (upper and middle panels), base-free natural deoxyribose homopolymer (PD: 0.01, 0.1, 0.3, 1 and 3 μg/mL, lower panel), or base-free phosphorothioate deoxyribose homopolymer (PS: 0.01, 0.1, 0.3, 1 and 3 μg/mL, lower panel). In the lower panel, unlabeled B-DNA or CpG-B ODN having stepwise increasing concentrations (0.1, 0.3, 1 and 3 μg/mL) was also used. The median inhibition concentrations (IC$_{50}$) of CpG-B ODN and PS were 1/150 and 1/100, respectively, of that of unlabeled B-DNA.

Example 14

Figure 14:
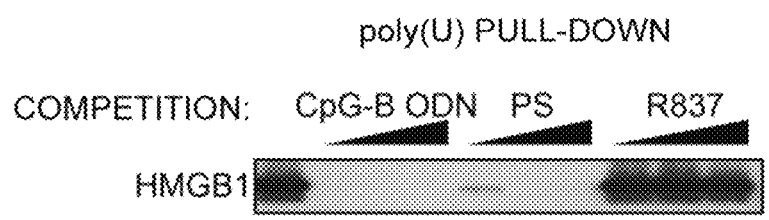
FIG. 14 is a set of photographs showing the results of Example 14.

In vitro pull-down assay using recombinant HMGB1 and biotin-bound poly(U) was performed in the presence of unlabeled CpG-B ODN, PS, or R837 having stepwise increasing concentrations (0.1, 1 and 10 μg/mL) The results are shown in FIG. 14.

Example 15

Figure 15:
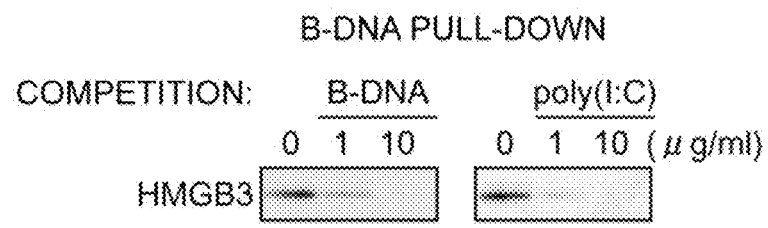
FIG. 15 is a set of photographs showing the results of Example 15.

In vitro pull-down assay using recombinant HMGB3 and biotin-bound B-DNA was performed in the presence or absence of 1 or 10 μg/mL of unlabeled B-DNA or poly(I:C). The results are shown in FIG. 15.

Essential Role of HMGB in Immune Response Activated by Nucleic Acid

Example 16

Figure 16:
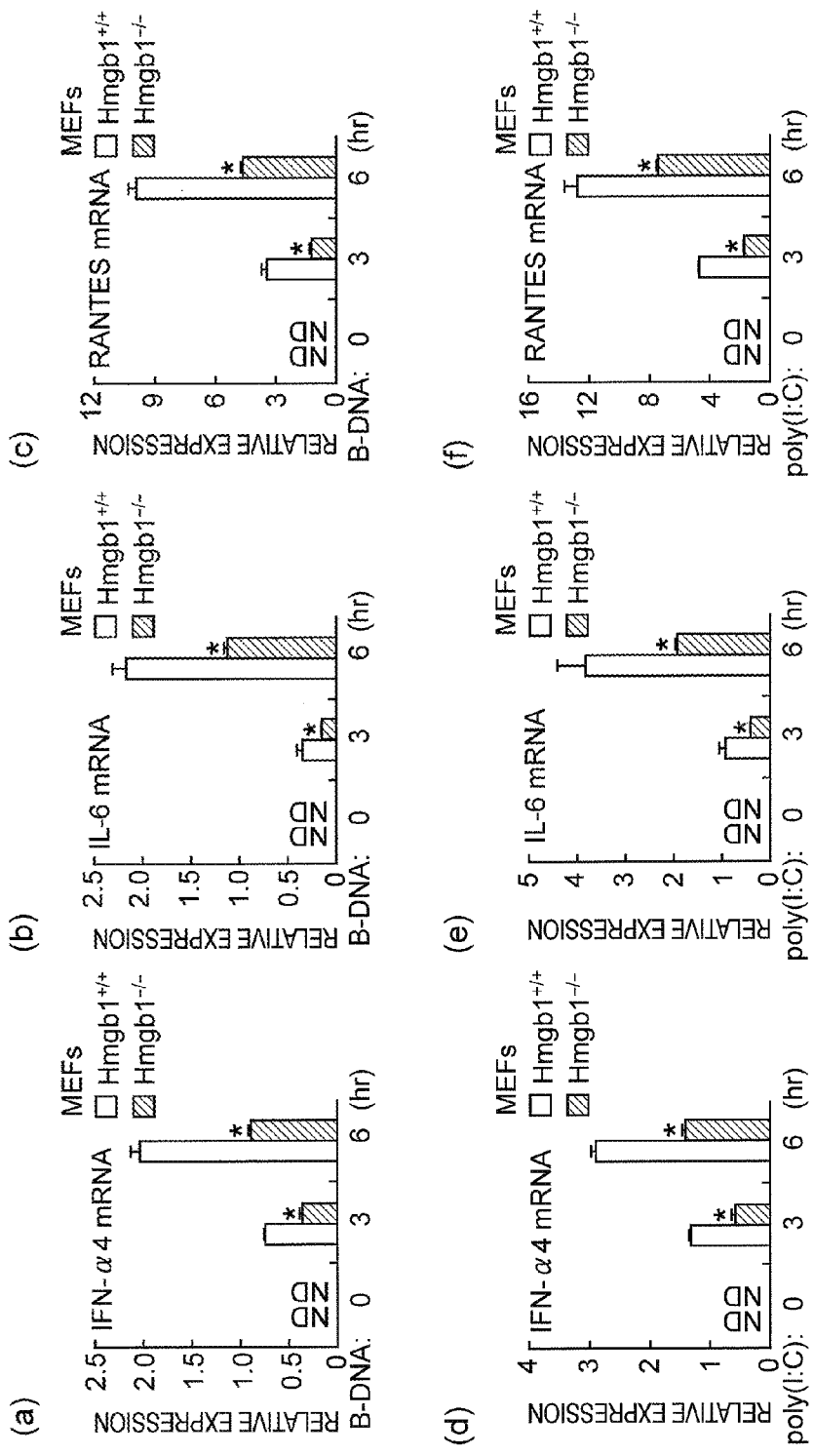
FIG. 16 is a set of graphs showing the results of Example 16.

B-DNA (FIGS. 16a, b and c) or poly(I:C) (FIGS. 16d, e and f) was lipotransfected (lipofection) into Hmgb1$^{+/+}$ or Hmgb1$^{-/-}$ MEFs. Subsequently, the expression levels of mRNAs of IFN-α4 (FIG. 16a and d), IL-6 (FIGS. 16b and e) and RANTES (FIGS. 16c and f) were measured by quantitative RT-PCR. The results are shown in FIG. 16. All data were shown as mean±standard deviation (n=3). ND means not detected. The symbol "*" indicates p<0.01 in comparison with Hmgb1$^{+/+}$ MEFs. The induction of various cytokine and chemokine genes decreased in the absence of HMGB1.

Example 17

Figure 17:
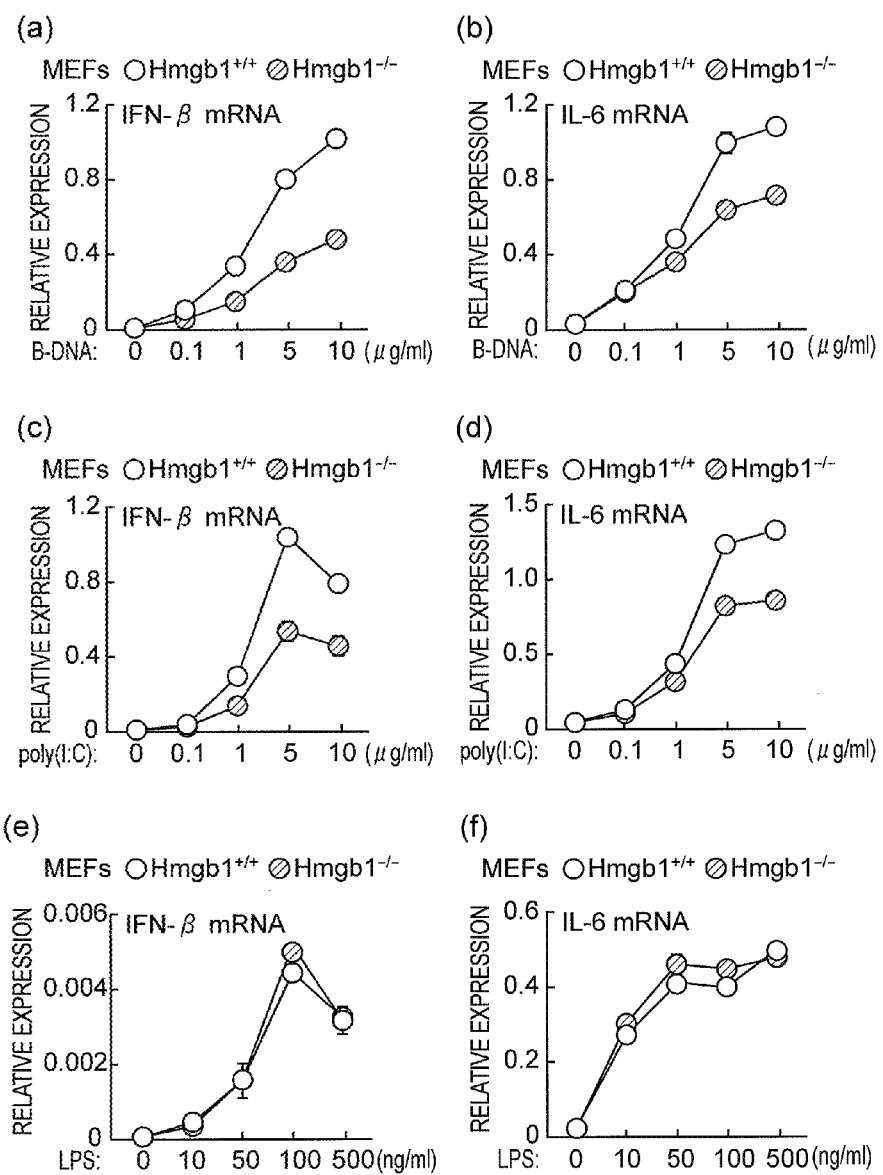
FIG. 17 is a set of graphs showing the results of Example 17.

Hmgb1$^{-/-}$ MEFs derived from wild-type and litters were stimulated with B-DNA having stepwise increasing concentrations (0.1, 1, 5 and 10 μg/mL) (FIGS. 17a and b) or poly(I:C) having stepwise increasing concentrations (0.1, 1, 5 and 10 μg/mL) (FIGS. 17c and d) for 6 hours or stimulated with LPS having stepwise increasing concentrations (10, 50, 100 and 500 ng/mL) (FIGS. 17e and f) for 2 hours. The expression of mRNAs of IFN-β (FIGS. 17a, c and e) and IL-6 (FIGS. 17b, d and f) was measured by quantitative RT-PCR. The results are shown in FIG. 17.

Example 18

Figure 18:
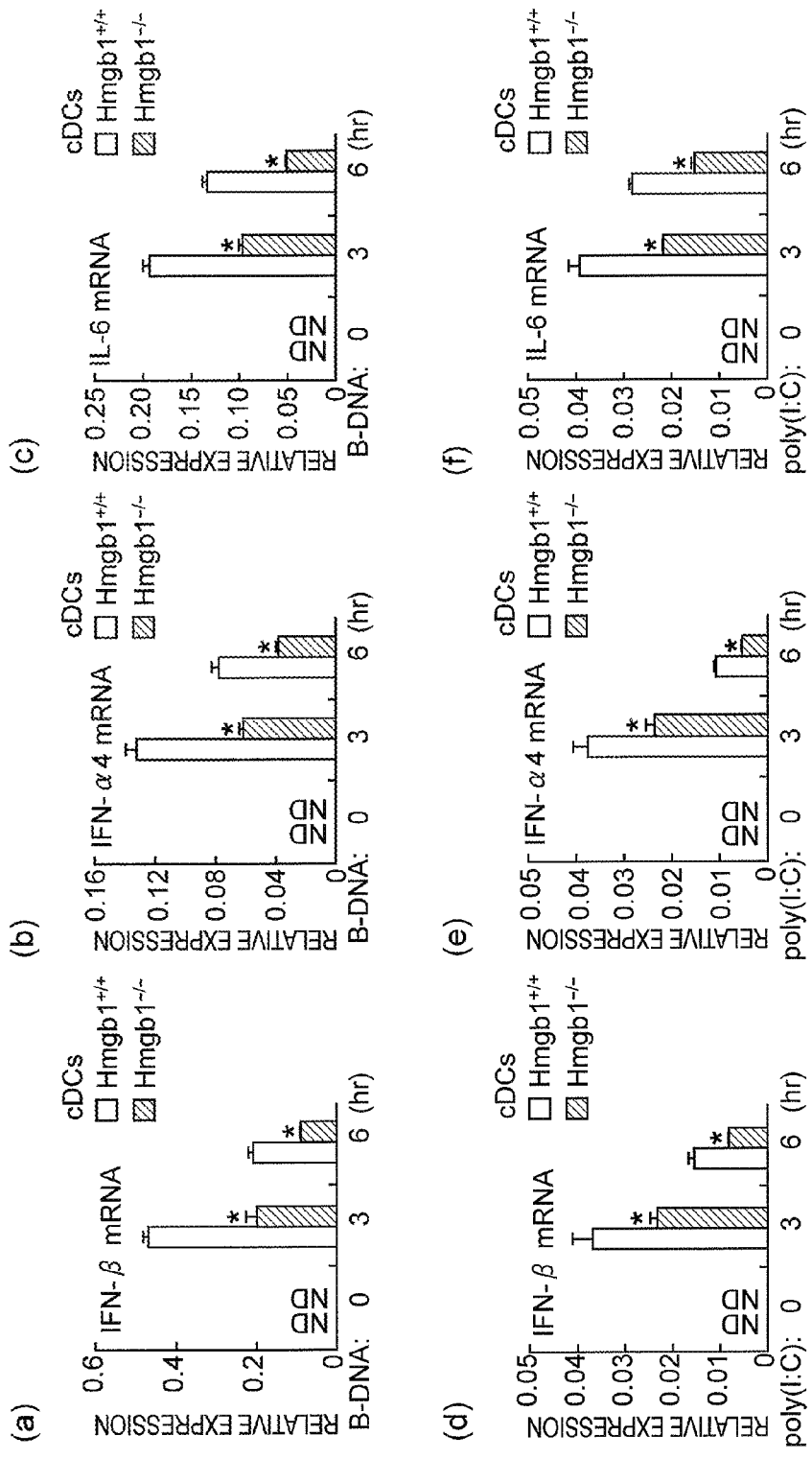
FIG. 18 is a set of graphs showing the results of Example 18.

B-DNA (FIGS. 18a, b and c) or poly(I:C) (FIGS. 18d, e and f) were lipotransfected (lipofection) into Hmgb1$^{+/+}$ or Hmgb1$^{-/-}$ cDCs (conventional dendritic cells). Subsequently, expression levels of mRNAs of IFN-β (FIGS. 18a and d), IFN-α4 (FIGS. 18b and e), IL-6 (FIGS. 18c and f) were measured by quantitative RT-PCR. The results are shown in FIG. 18. All data were shown as mean±standard deviation (n=3). ND means not detected. The symbol "*" indicates p<0.01 in comparison with Hmgb1$^{+/+}$ cDCs.

The induction of various cytokine and chemokine genes decreased in the absence of HMGB1. It is believed that the response to poly(I:C) in cDCs is mediated by both RLR and TLR3.

Example 19

Figure 19:
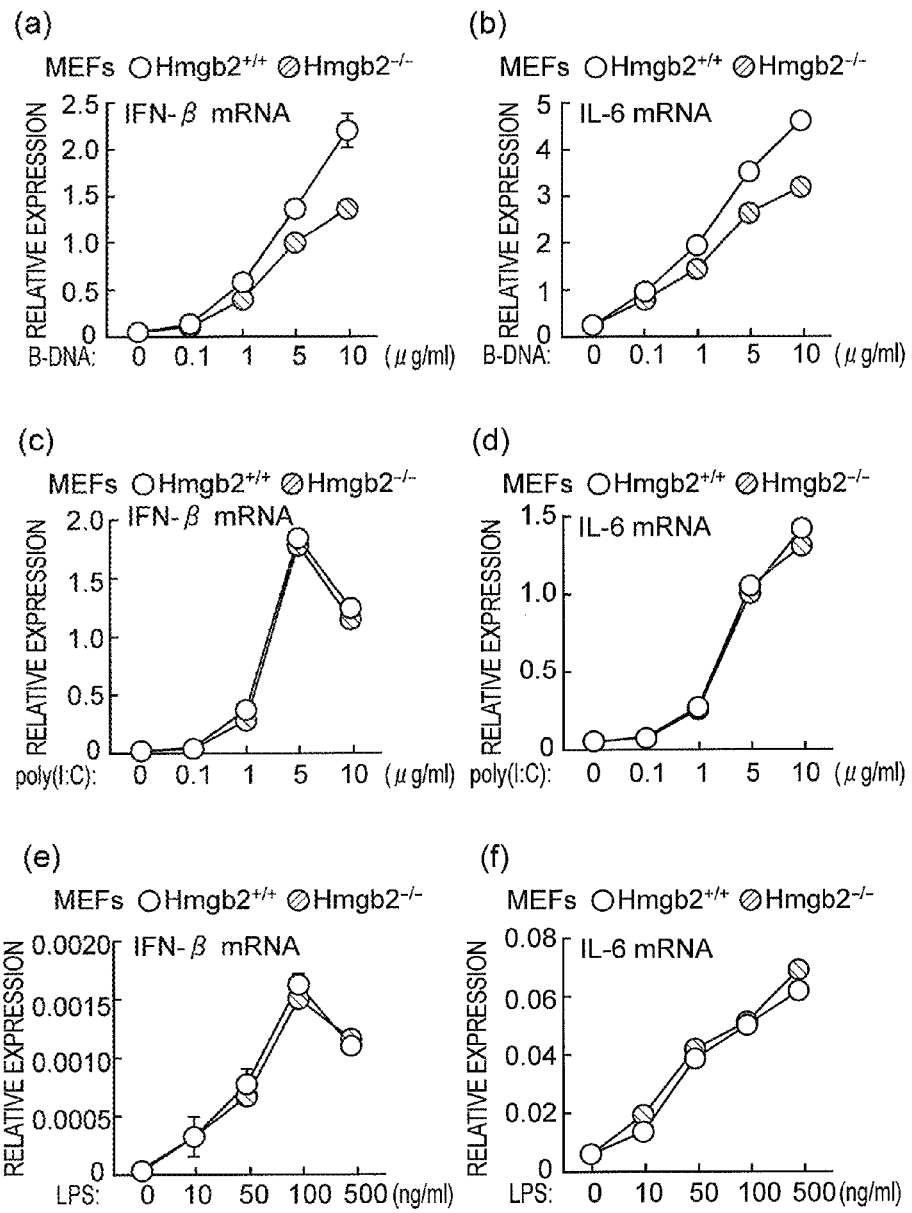
FIG. 19 is a set of graphs showing the results of Example 19.

Induction of cytokine genes in the absence of HMGB2 was investigated. Hmgb2$^{-/-}$ MEFs derived from wild-type and litters were stimulated with B-DNA having stepwise increasing concentrations (0.1, 1, 5 and 10 μg/mL) (FIGS. 19a and b) or poly(I:C) having stepwise increasing concentrations (0.1, 1, 5 and 10 μg/mL) (FIGS. 19c and d) for 6 hours or stimulated with LPS having stepwise increasing concentrations (10, 50, 100 and 500 ng/mL) (FIGS. 19e and f) for 2 hours. The expression of mRNAs of IFN-β (FIGS. 19a, c and e) and IL-6 (FIGS. 19b, d and f) was measured by quantitative RT-PCR. The results are shown in FIG. 19. All data were shown as mean±standard deviation (n=3).

Example 20

Figure 20:
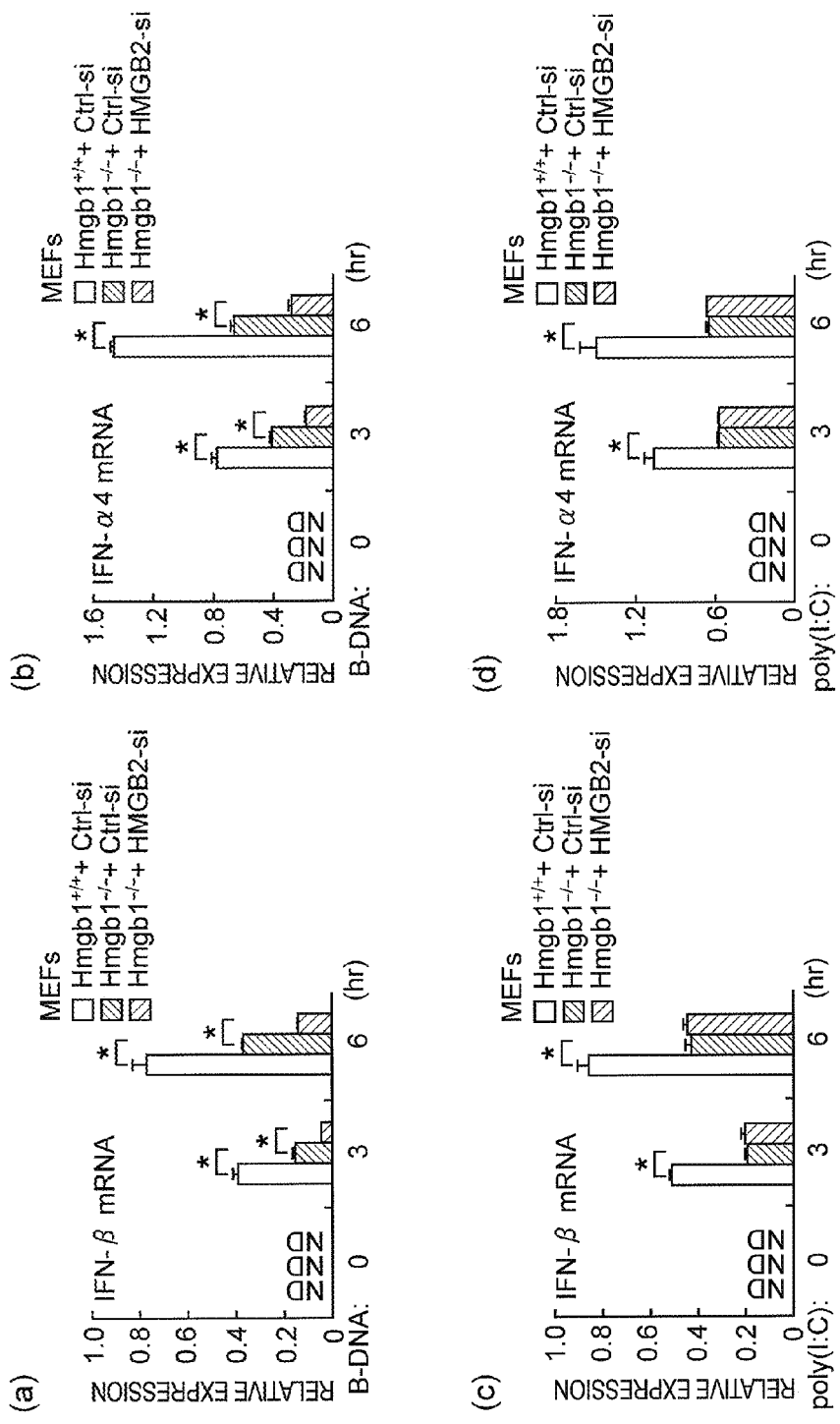
FIG. 20 is a set of graphs showing the results of Example 20.

The influence of knock-down of HMGB2 in Hmgb1$^{-/-}$ MEFs was investigated. Hmgb1$^{-/-}$ MEFs transformed with retrovirus expressing siRNA (HMBG2-si) targeting HMGB2 or control siRNA (Ctrl-si) were stimulated with B-DNA (FIGS. 20a and b) or poly(I:C) (FIGS. 20c and d), and the expression of mRNAs of IFN-β (FIG. 20a and c) and IFN-α4 (FIGS. 20b and d) were measured by quantitative RT-PCR. Hmgb1$^{+/+}$ expressing control siRNA (Ctrl-si) was also analyzed for comparison. The results are shown in FIG. 20. All data were shown as mean±standard deviation (n=3). The symbol "*" indicates p<0.01 in comparison with the cells expressing control siRNA (Ctrl-si).

Example 21

Figure 21:
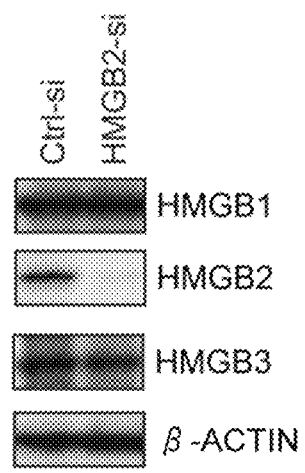
FIG. 21 is a set of photographs showing the results of Example 21.

The effect of siRNA targeting HMGB2 was investigated. Wild-type MEFs were transformed with the shown siRNA retrovirus, and the expression of each HMGB protein was analyzed by immunoblot analysis. The results are shown in FIG. 21.

Example 22

Figure 22:
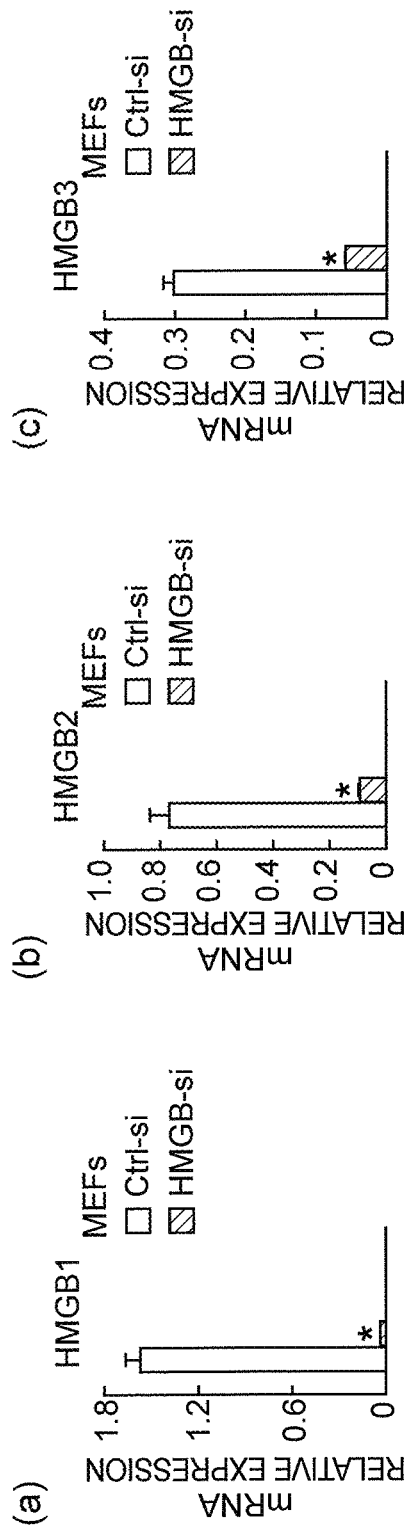
FIG. 22 is a set of graphs showing the results of Example 22.

The effect of siRNA targeting all HMGBs was investigated. Wild-type MEFs were transformed with retrovirus expressing siRNA targeting all HMGBs (HMBG-si) or control siRNA (Ctrl-si), and the expressions of HMGB1 (FIG. 22a), HMGB2 (FIG. 22b) and HMGB3 (FIG. 22c) proteins were analyzed by quantitative RT-PCR. The results are shown in FIG. 22. The symbol "*" indicates p<0.01 in comparison with the Ctrl-si-introduced MEFs.

Example 23

Figure 23:
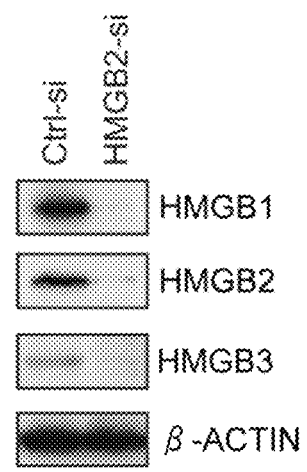
FIG. 23 is a set of photographs showing the results of Example 23.

The effect of siRNA targeting all HMGBs was investigated. Wild-type MEFs were transformed with retrovirus expressing siRNA targeting all HMGBs (HMBG-si) or control siRNA (Ctrl-si), and the expression of each HMGB protein was analyzed by immunoblot analysis. The results are shown in FIG. 23.

Example 24

Figure 24:
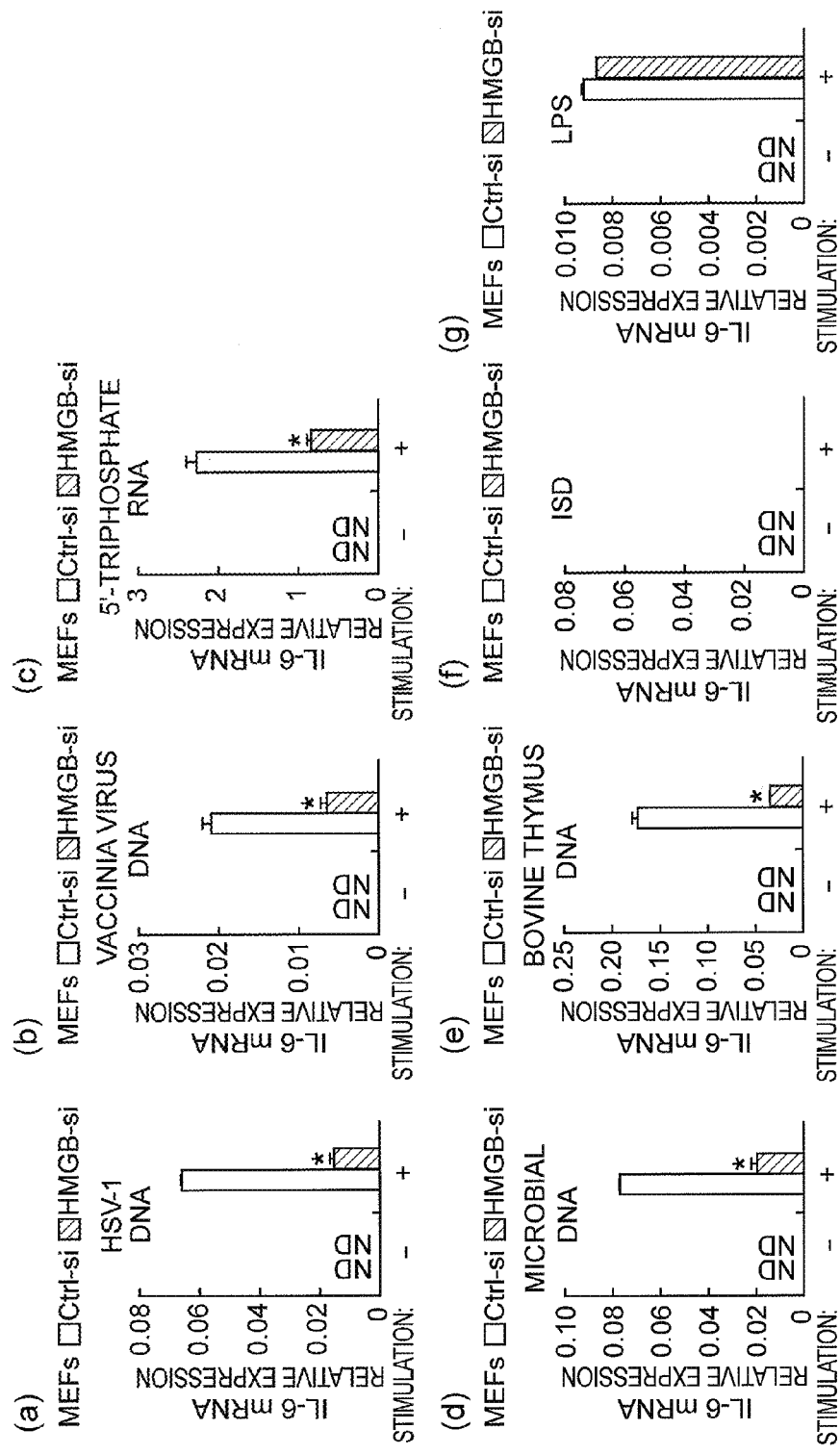
FIG. 24 is a set of graphs showing the results of Example 24.

Deficiency in immune response against stimulations of cytoplasms with various nucleic acids in HMGB deletion cells was investigated. MEFs transformed with retrovirus expressing siRNA targeting all HMGBs (HMBG-si) or control siRNA (Ctrl-si) were stimulated with shown nucleic acids of HSV-1 DNA (FIG. 24a), vaccinia virus DNA (FIG. 24b), 5'-triphosphate RNA (FIG. 24c), microbial DNA (FIG. 24d), bovine thymus DNA (FIG. 24e), or ISD (FIG. 24f) for 6 hours or with LPS (200 ng/mL) (FIG. 24g) for 2 hours. The mRNA expression levels of the IL-6 gene were measured by quantitative RT-PCR. The results are shown in FIG. 24. All data were shown as mean±standard deviation (n=3). The symbol "*" indicates p<0.01 in comparison with Ctrl-si-introduced MEFs.

Example 25

Figure 25:
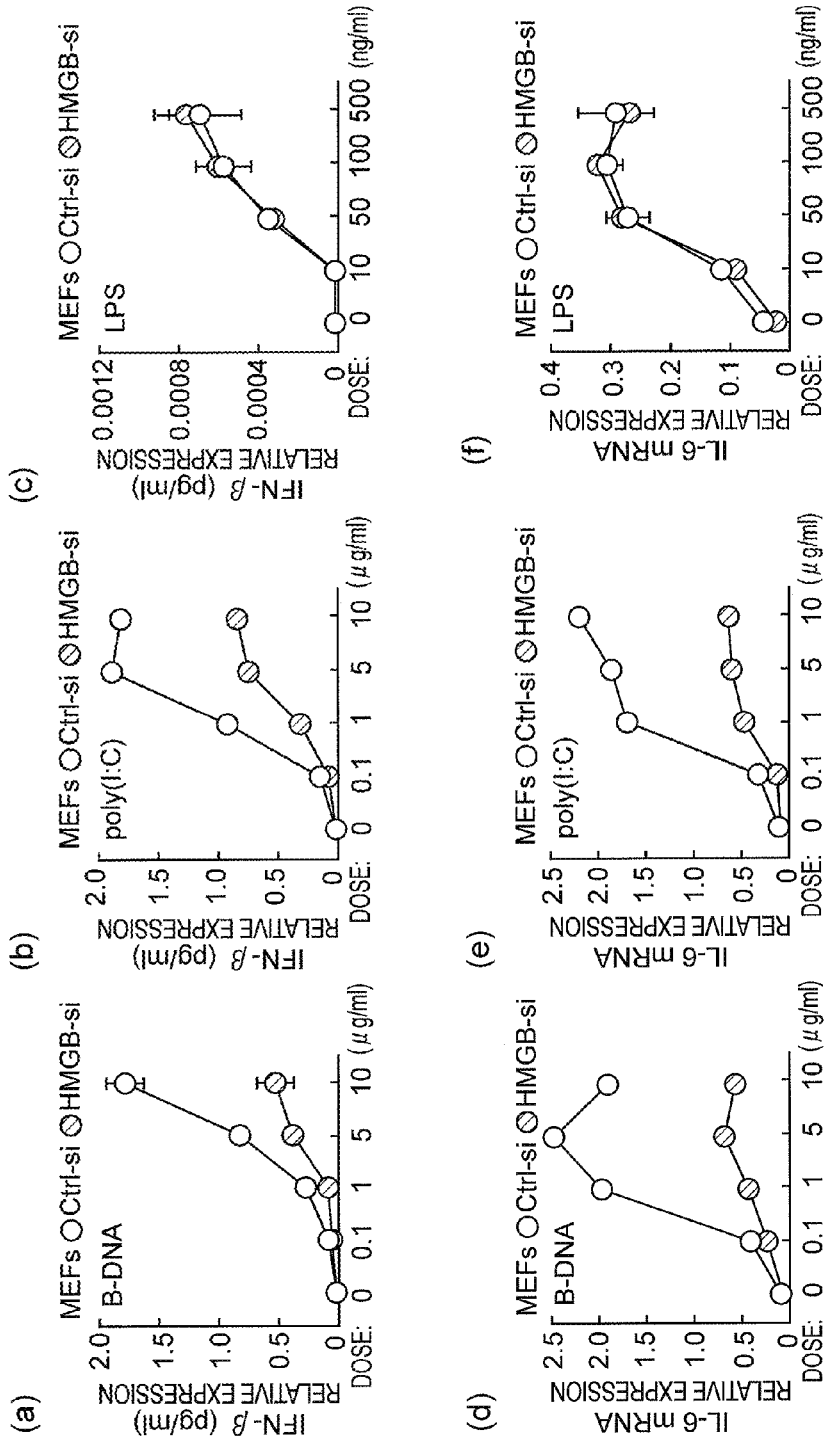
FIG. 25 is a set of graphs showing the results of Example 25.

Deficiency in immune response against nucleic acid ligands at various concentrations in HMGB deletion cells was investigated. MEFs expressing siRNA targeting all HMGBs (HMBG-si) or control siRNA (Ctrl-si) were stimulated with B-DNA having stepwise increasing concentrations (0.1, 1, 5 and 10 µg/mL) (FIGS. 25a and d) or poly(I:C) having stepwise increasing concentrations (0.1, 1, 5 and 10 µg/mL) (FIGS. 25b and e) for 6 hours or stimulated with LPS having stepwise increasing concentrations (10, 50, 100 and 500 ng/mL) (FIGS. 25c and f) for 2 hours. The expression of mRNA of IFN-β (FIGS. 25a, b and c) or IL-6 (FIGS. 25d, e and f) was measured by quantitative RT-PCR. The results are shown in FIG. 25. All data were shown as mean±standard deviation (n=3).

Example 26

Figure 26:
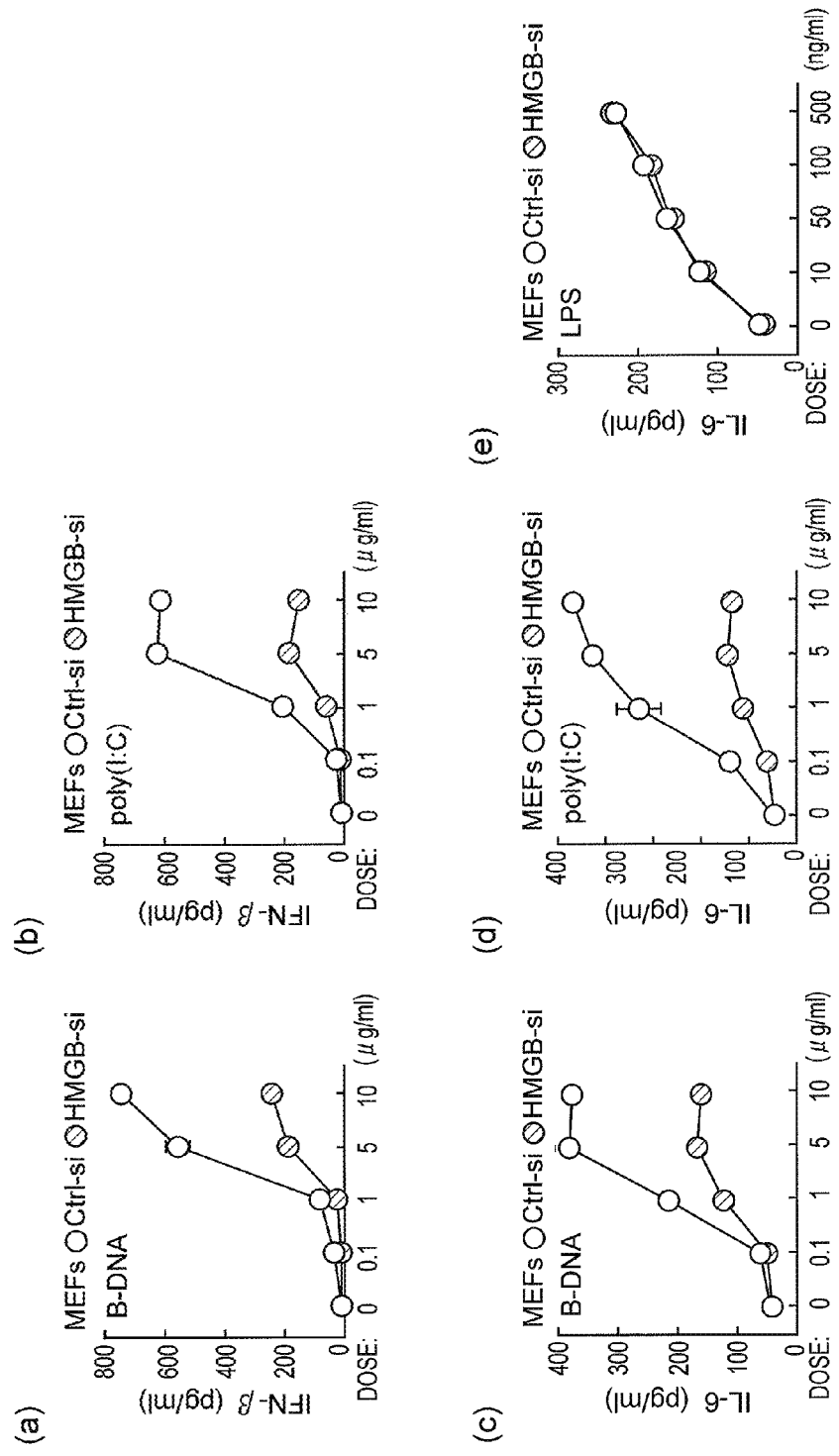
FIG. 26 is a set of graphs showing the results of Example 26.

Deficiency in immune response against nucleic acid ligands at various concentrations in HMGB deletion cells was investigated. MEFs expressing siRNA targeting all HMGBs (HMBG-si) or control siRNA (Ctrl-si) were stimulated with B-DNA having stepwise increasing concentrations (0.1, 1, 5 and 10 µg/mL) (FIGS. 26a and c) or poly(I:C) having stepwise increasing concentrations (0.1, 1, 5 and 10 µg/mL) (FIGS. 26b and d) for 6 hours or stimulated with LPS having stepwise increasing concentrations (10, 50, 100 and 500 ng/mL) (FIG. 26e) for 2 hours. The expression of IFN-β (FIGS. 26a and b) or IL-6 (FIGS. 26c, d and e) was measured by ELISA. The results are shown in FIG. 26. All data were shown as mean±standard deviation (n=3).

Example 27

Figure 27:
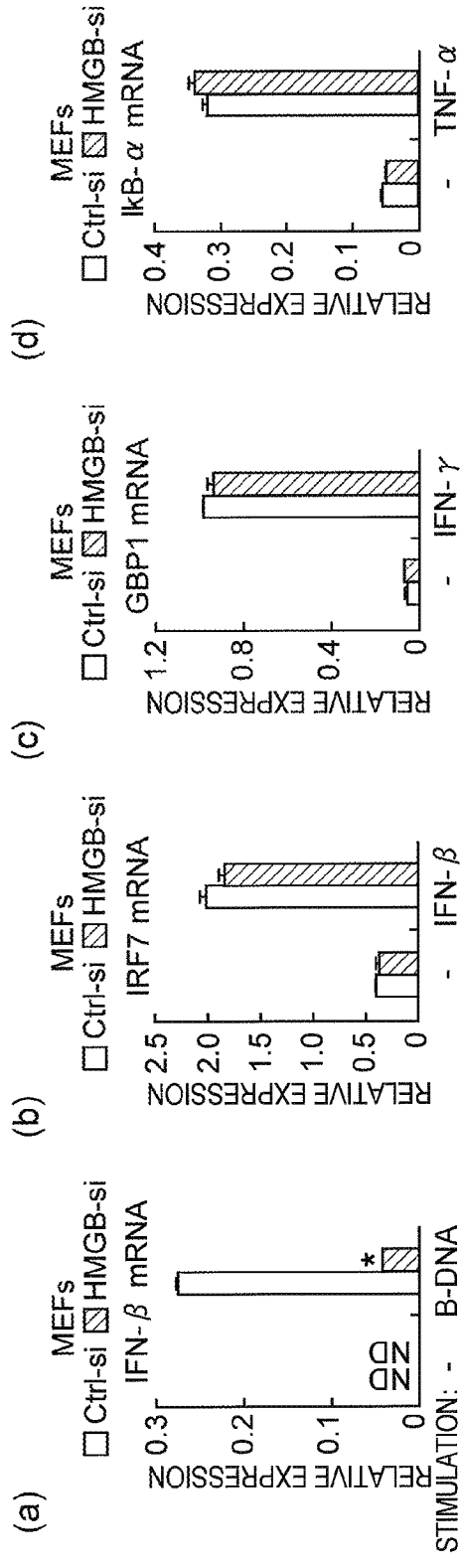
FIG. 27 is a set of graphs showing the results of Example 27.

Responses against various cytokine stimulations in HMGB deletion cells were investigated. MEFs expressing siRNA targeting all HMGBs (HMBG-si) or control siRNA (Ctrl-si) were stimulated with B-DNA (10 µg/mL) for 6 hours (FIG. 27a), IFN-β (500 units/mL) for 6 hours (FIG. 27b), IFN-γ (1 unit/mL) for 2 hours (FIG. 27c), or TNF-α (10 ng/mL) for 2 hours (FIG. 27d). The mRNA expression levels of IFN-β (FIG. 27a), IRF7 (FIG. 27b), GBP1 (FIG. 27c) and IκB-α (FIG. 27d) were measured by quantitative RT-PCR. The results are shown in FIG. 27. All data were shown as mean±standard deviation (n=3). Basically, the same results were obtained in different amounts of these ligands.

Example 28

Figure 28:
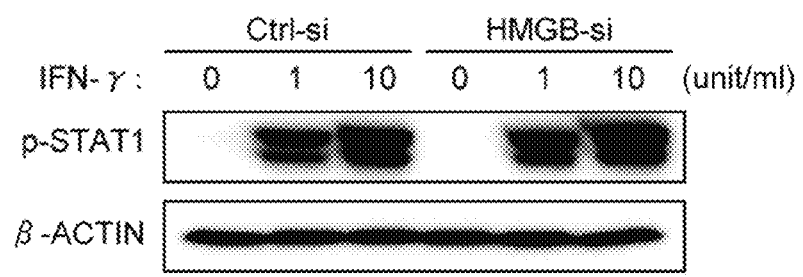
FIG. 28 is a set of photographs showing the results of Example 28.

Activation of STAT1 induced by IFN-γ in HMGB deletion cells was investigated. MEFs expressing siRNA targeting all HMGBs (HMBG-si) or control siRNA (Ctrl-si) were stimulated with IFN-γ (1 or 10 units/mL) for 30 minutes. Phosphorylated STAT1 and β-actin were detected with anti-phosphorylated STAT1 (p-STAT1) and anti-β-actin antibodies, respectively. The results are shown in FIG. 28.

Example 29

Figure 29:
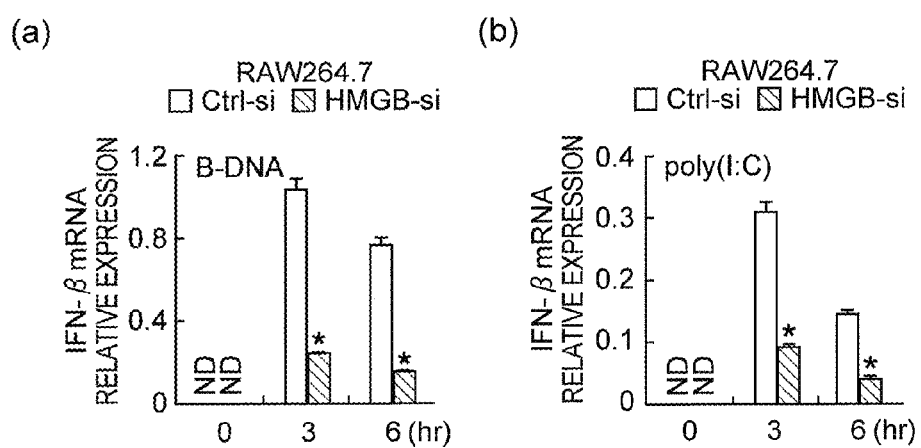
FIG. 29 is a set of graphs showing the results of Example 29.

Deficiency in immune response against stimulation of cytoplasms with nucleic acid in HMGB deletion RAW264.7 cells was investigated. RAW264.7 cells expressing siRNA targeting all HMGBs (HMBG-si) or control siRNA (Ctrl-si) were stimulated with B-DNA (FIG. 29a) or poly(I:C) (FIG. 29b) for the shown periods of time. The mRNA expression levels of IFN-β genes were measured by quantitative RT-PCR. The results are shown in FIG. 29. The symbol "*" indicates p<0.01 in comparison with Ctrl-si-expressing cells.

Example 30

Figure 30:
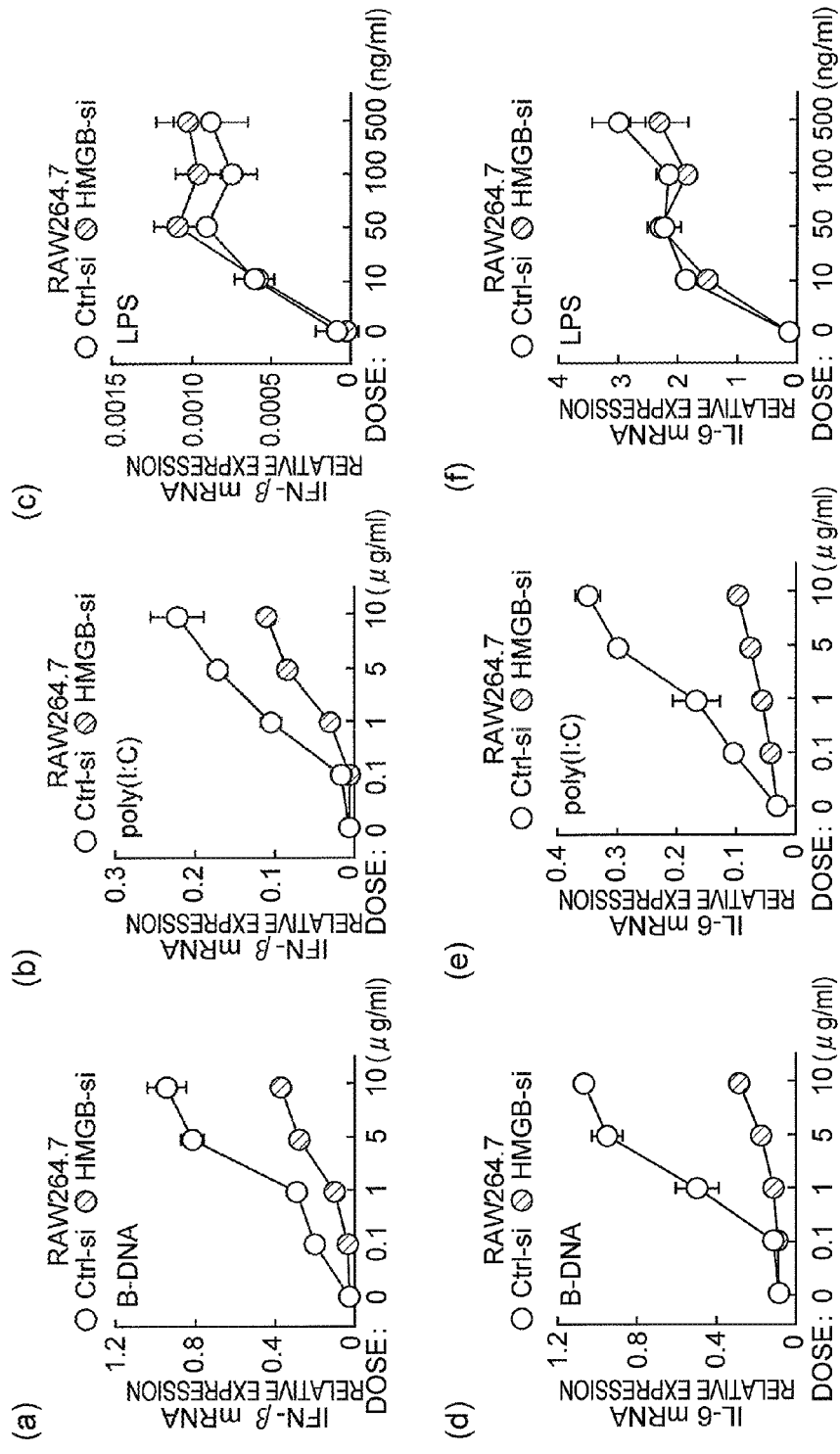
FIG. 30 is a set of graphs showing the results of Example 30.

RAW264.7 cells expressing HMBG-si or Ctrl-si were stimulated with B-DNA having stepwise increasing concentrations (0.1, 1, 5 and 10 µg/mL) (FIGS. 30a and d) or poly(I:C) having stepwise increasing concentrations (0.1, 1, 5 and 10 µg/mL) (FIGS. 30b and e) for 6 hours or stimulated with LPS having stepwise increasing concentrations (10, 50, 100 and 500 ng/mL) (FIGS. 30c and f) for 2 hours. The mRNA expression levels of shown cytokine genes were measured by quantitative RT-PCR. The results are shown in FIG. 30. All data were shown as mean±standard deviation (n=3).

Example 31

Figure 31:
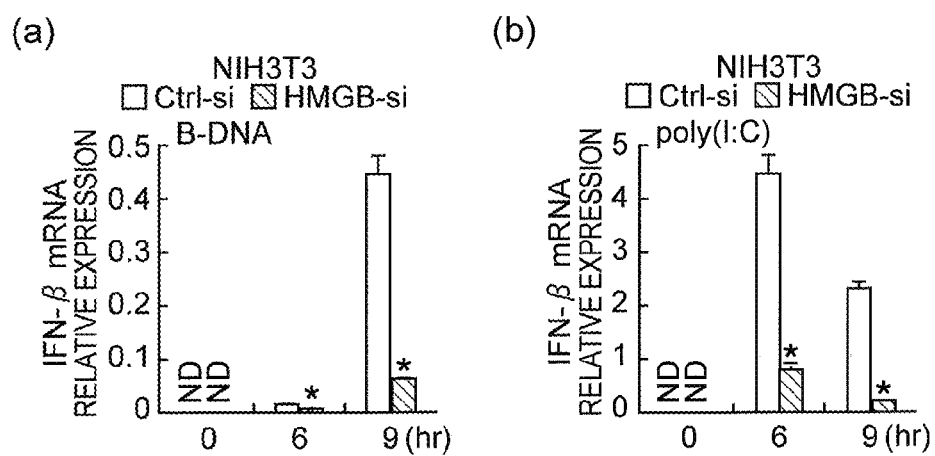
FIG. 31 is a set of graphs showing the results of Example 31.

Immune response against stimulations of cytoplasms with nucleic acid in HMGB deletion NIH3T3 cells was investigated. NIH3T3 cells expressing siRNA targeting all HMGBs (HMBG-si) or control siRNA (Ctrl-si) were stimulated with B-DNA (FIG. 31a) or poly(I:C) (FIG. 31b) for the shown periods of time. The mRNA expression levels of IFN-β were measured by quantitative RT-PCR. The results are shown in FIG. 31. The symbol "*" indicates p<0.01 in comparison with Ctrl-si-expressing cells.

Example 32

Figure 32:
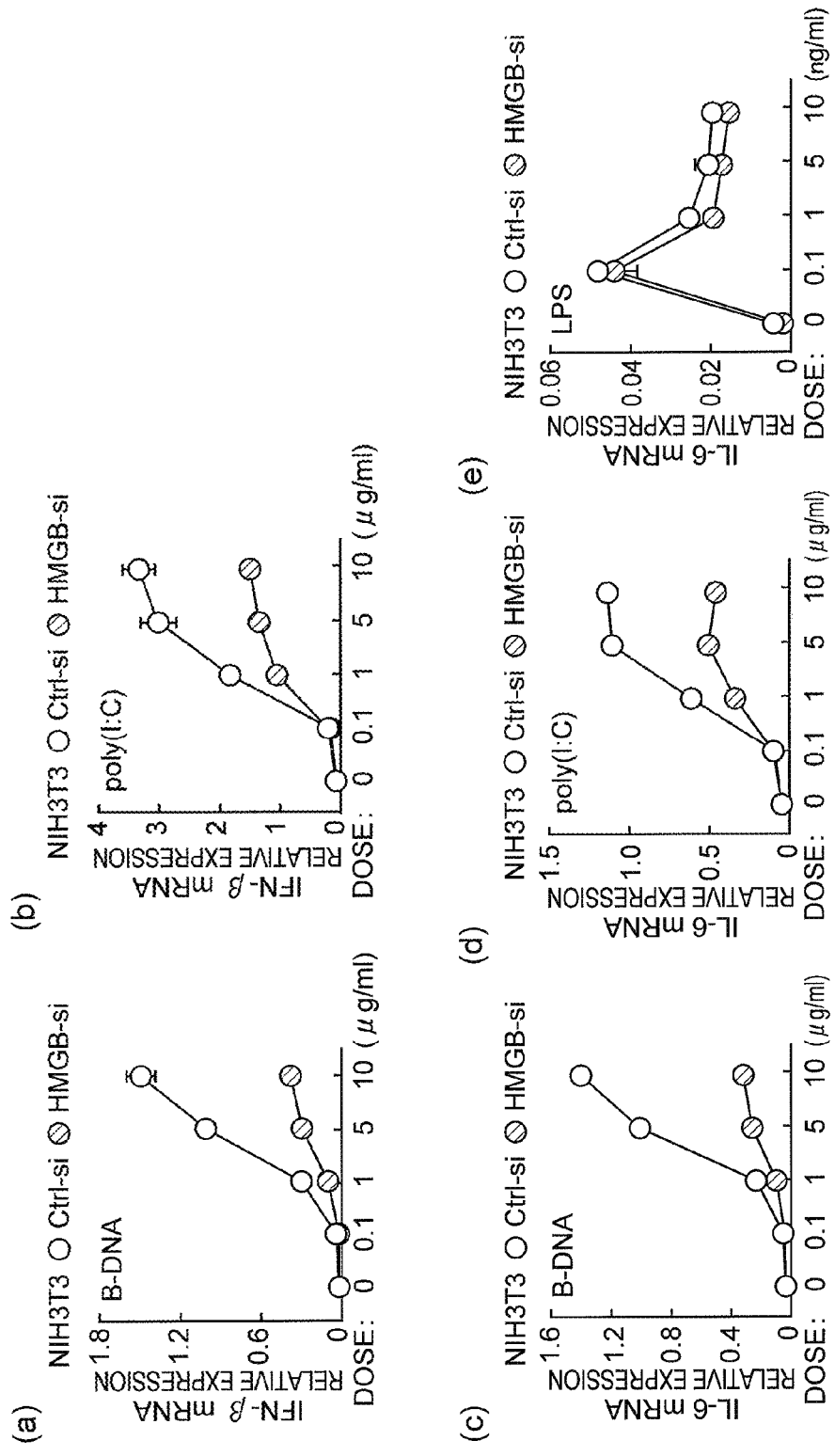
FIG. 32 is a set of graphs showing the results of Example 32.

NIH3T3 cells expressing HMBG-si or Ctrl-si were stimulated with B-DNA having stepwise increasing concentrations (0.1, 1, 5 and 10 µg/mL) (FIGS. 32a and c) or poly(I:C) having stepwise increasing concentrations (0.1, 1, 5 and 10 µg/mL) (FIGS. 32b and d) for 9 hours or stimulated with LPS having stepwise increasing concentrations (10, 50, 100 and 500 ng/mL) (FIG. 32e) for 2 hours. The mRNA expression levels of IFN-β (FIGS. 32a and b) or IL-6 (FIGS. 32c, d and e) were measured by quantitative RT-PCR. The results are shown in FIG. 32. All data were shown as mean±standard deviation (n=3).

Example 33

Involvement of HMGB in activation of the inflammasome pathway by B-DNA stimulation and cell death was investigated.

Figure 33:
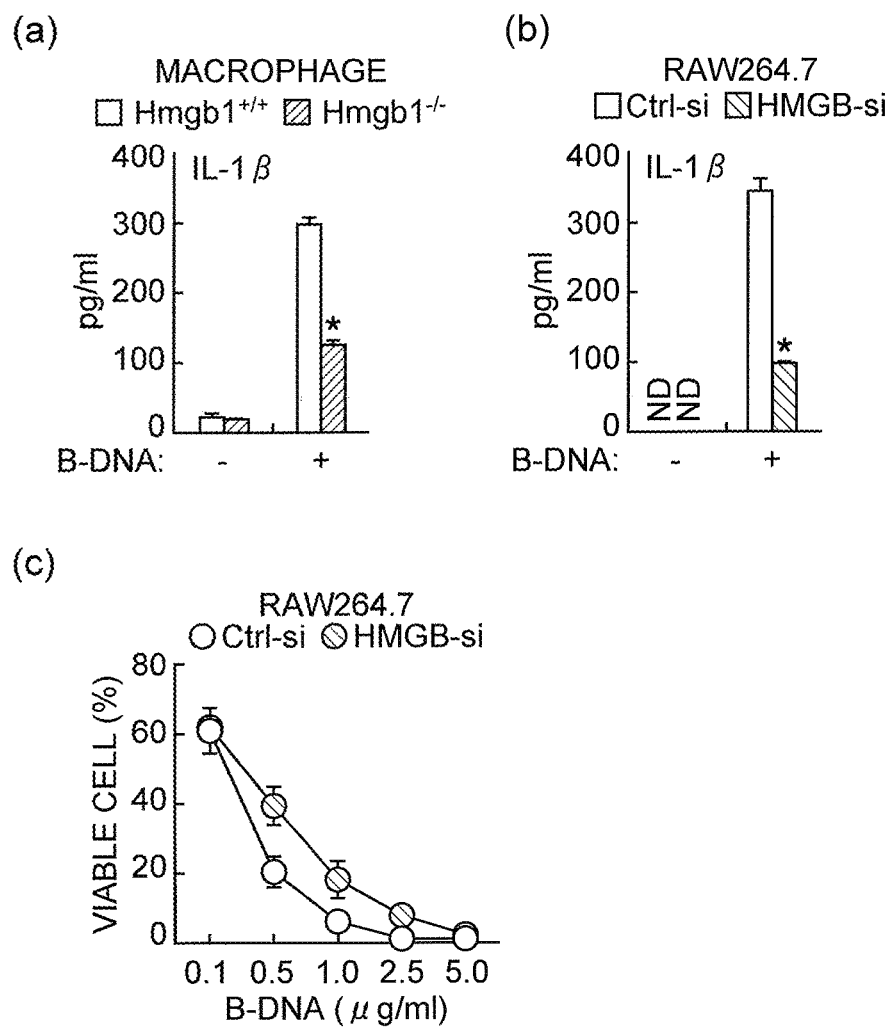
FIG. 33 is a set of graphs showing the results of Example 33.

B-DNA was lipotransfected into Hmgb1$^{+/+}$ or Hmgb1$^{-/-}$ fetal liver hematopoietic progenitor cell-derived macrophages (FIG. 33a) and RAW264.7 cells (FIG. 33b) expressing siRNA targeting all HMGBs (HMBG-si) or control siRNA (Ctrl-si), and the amounts of secreted mature IL-1β were measured by ELISA 12 hours later. RAW264.7 cells were stimulated with 50 ng/mL of LPS for 16 hours to activate inflammasome. The results are shown in FIG. 33. All data were shown as mean±standard deviation (n=3). The results are shown in FIG. 33. The symbol "*" indicates p<0.01 in comparison with wild-type cells or Ctrl-si-expressing cells. ND means not detected.

RAW264.7 cells expressing HMBG-si or Ctrl-si were stimulated with B-DNA having stepwise increasing concentrations. The cells were collected after the stimulation for 24 hours and were stained with trypan blue. The percentage of viable cells to untreated cells was calculated. The results are shown in FIG. 33c. RAW264.7 cells expressing HMGB-si showed higher resistance to cell death induced by DNA. All data were shown as mean±standard deviation (n=3).

Example 34

Figure 34:
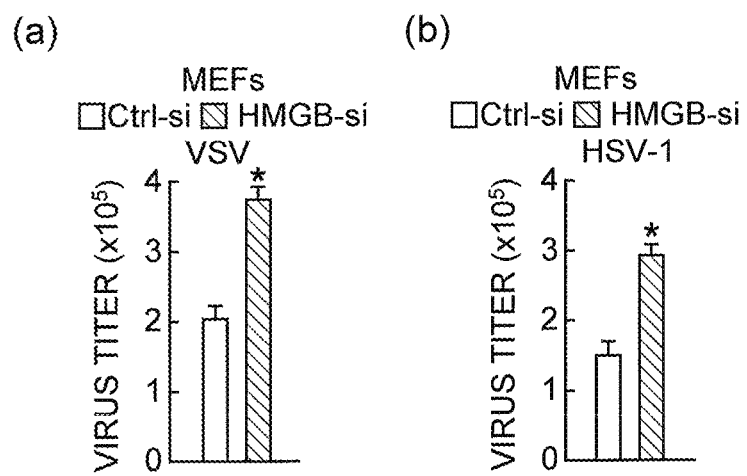
FIG. 34 is a set of graphs showing the results of Example 34.

MEFs expressing siRNA targeting all HMGBs (HMBG-si) or control siRNA (Ctrl-si) were infected with VSV (FIG. 34a) or HSV-1 (FIG. 34b), and the virus titers were measured 24 hours later. The results are shown in FIG. 34. All data were shown as mean±standard deviation (n=3). The symbol "*" indicates p<0.01 in comparison with Ctrl-si-expressing cells.

Example 35

Figure 35:
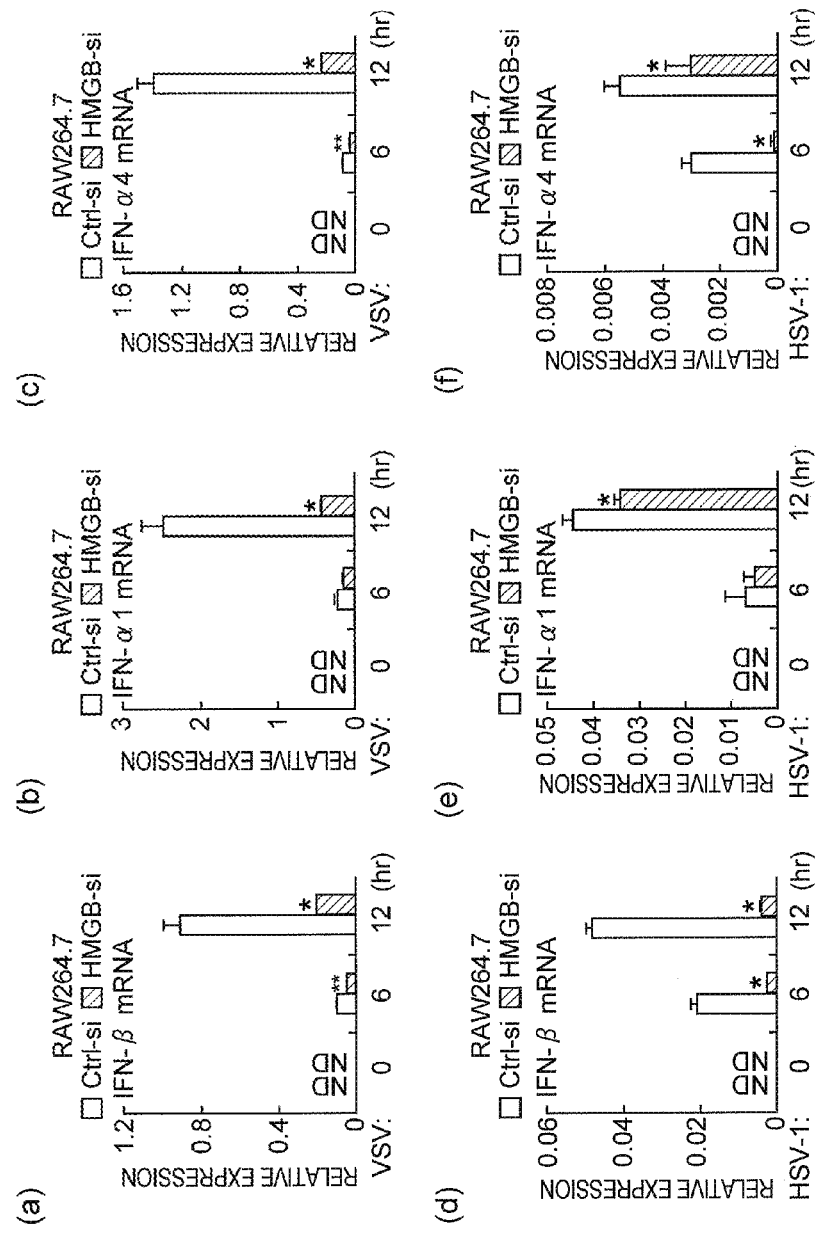
FIG. 35 is a set of graphs showing the results of Example 35.

RAW264.7 cells expressing siRNA targeting all HMGBs (HMBG-si) or control siRNA (Ctrl-si) were infected with VSV (FIGS. 35a, b and c) or HSV-1 (FIGS. 35d, e and f). Subsequently, mRNA expression levels of IFN-β (FIGS. 35a and d), IFN-α1 (FIGS. 35b and e) and IFN-α4 (c and f) were measured. The results are shown in FIG. 35. The symbol "*" indicates p<0.01 in comparison with Ctrl-si-expressing cells and the symbol "**" indicates p<0.05 in comparison with Ctrl-si-expressing cells. ND means not detected.

Example 36

Figure 36:
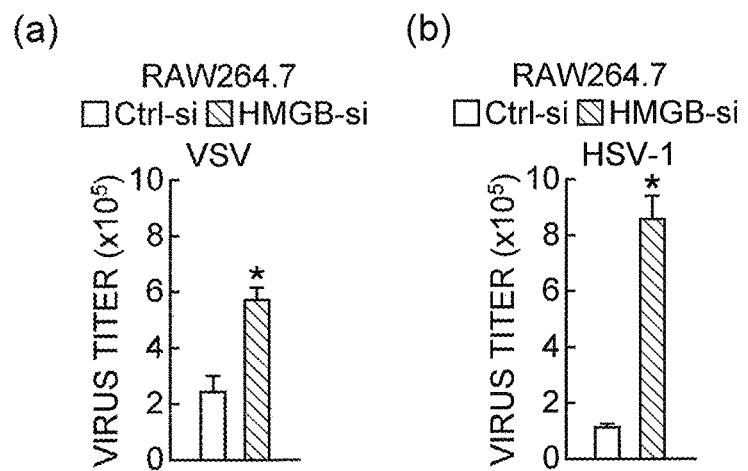
FIG. 36 is a set of graphs showing the results of Example 36.

RAW264.7 cells expressing siRNA targeting all HMGBs (HMBG-si) or control siRNA (Ctrl-si) were infected with VSV or HSV-1. Subsequently, the virus titers were measured. The results are shown in FIG. 36. The symbol "*" indicates p<0.01 in comparison with Ctrl-si-expressing cells.

HMGB is Necessary for Activation of TLR Mediated by Nucleic Acid

Example 37

Figure 37:
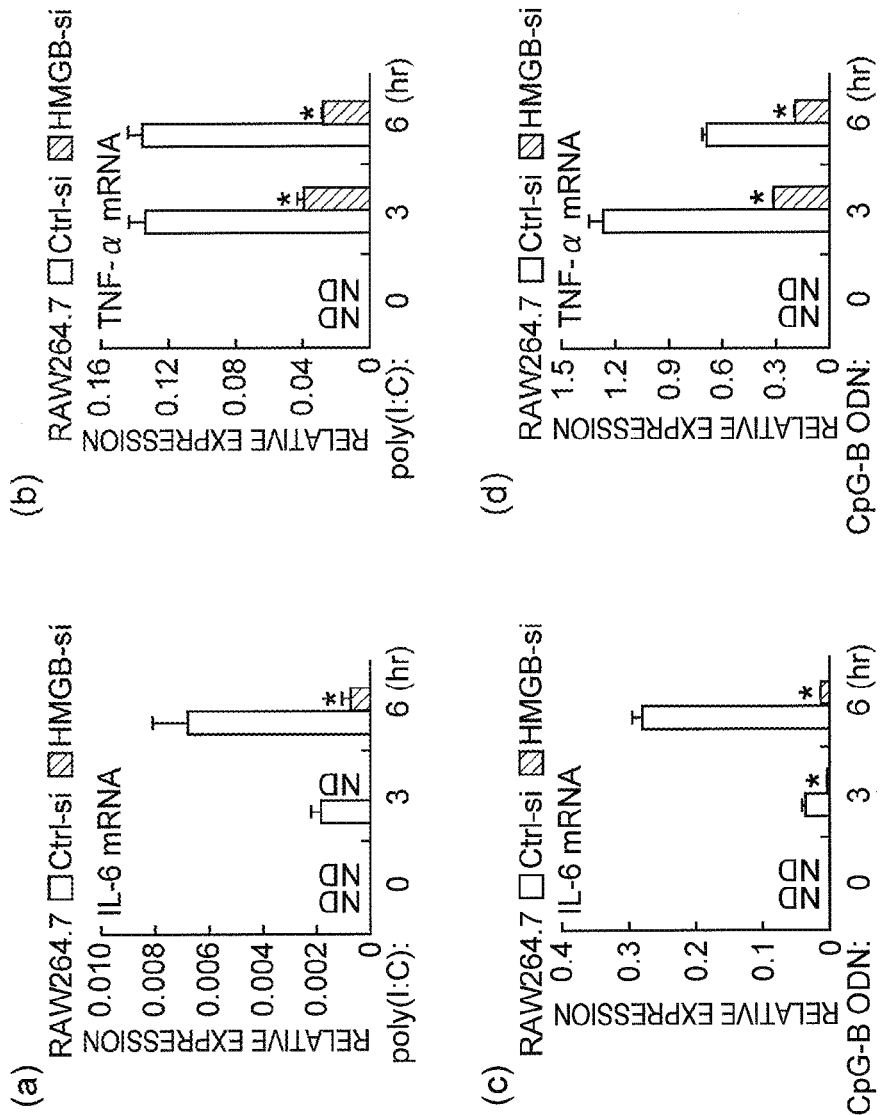
FIG. 37 is a set of graphs showing the results of Example 37.

RAW264.7 cells expressing siRNA targeting all HMGBs (HMBG-si) or control siRNA (Ctrl-si) were stimulated with poly(I:C) (FIGS. 37a and b) or CpG-B ODN (FIGS. 37c and d), and the expression levels of mRNAs of IL-6 (FIGS. 37a and c) and TNF-α (FIGS. 37b and d) were measured by quantitative RT-PCR. The results are shown in FIG. 37. All data were shown as mean±standard deviation (n=3). The symbol "*" indicates p<0.01 in comparison with Ctrl-si-expressing cells. ND means not detected.

Example 38

Figure 38:
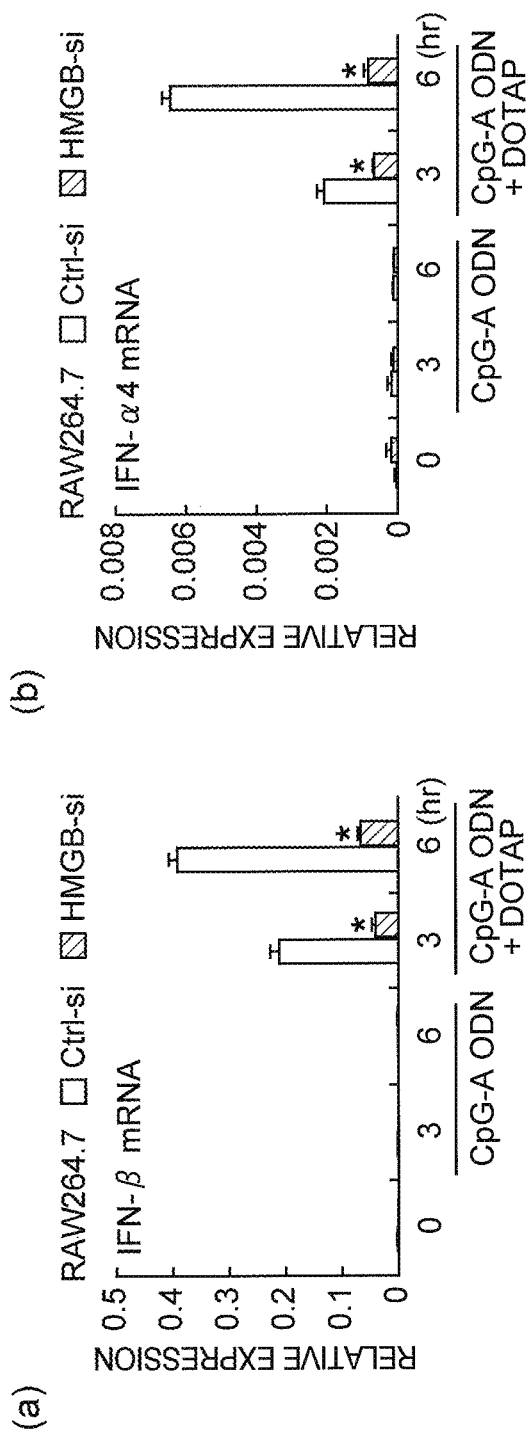
FIG. 38 is a set of graphs showing the results of Example 38.

RAW264.7 cells expressing siRNA targeting all HMGBs (HMBG-si) or control siRNA (Ctrl-si) were stimulated with CpG-A ODN or CpG-A ODN and DOTAP, and expression levels of mRNAs of IFN-β (FIG. 38a) and IFN-α4 (FIG. 38b) were measured by quantitative RT-PCR. DOTAP (trade name, Roche Diagnostics K.K.) is a reagent for introducing molecules negatively charged, such as DNA and RNA, into eukaryotic cells through cationic liposome. The results are shown in FIG. 38. All data were shown as mean±standard deviation (n=3). The symbol "*" indicates p<0.01 in comparison with Ctrl-si-expressing cells.

Example 39

Figure 39:
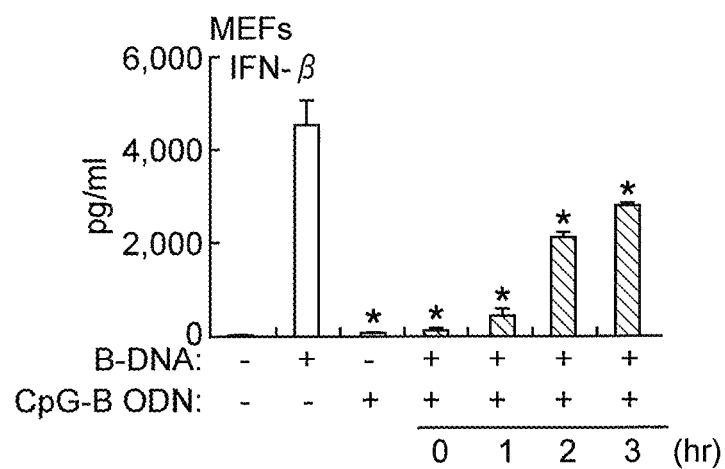
FIG. 39 is a graph showing the results of Example 39.

Inhibition of immune response activated by nucleic acid by stimulation using a nucleic acid analogue was investigated. MEFs were lipotransfected with B-DNA and were then co-stimulated with 1 μM CpG-B ODN for 0, 1, 2, or 3 hours, and induction of IFN-β was measured by ELISA. The results are shown in FIG. 39. All data were shown as mean±standard deviation (n=3). The symbol "*" indicates p<0.01 in comparison with stimulation with B-DNA without performing stimulation with CpG-B ODN.

Example 40

Figure 40:
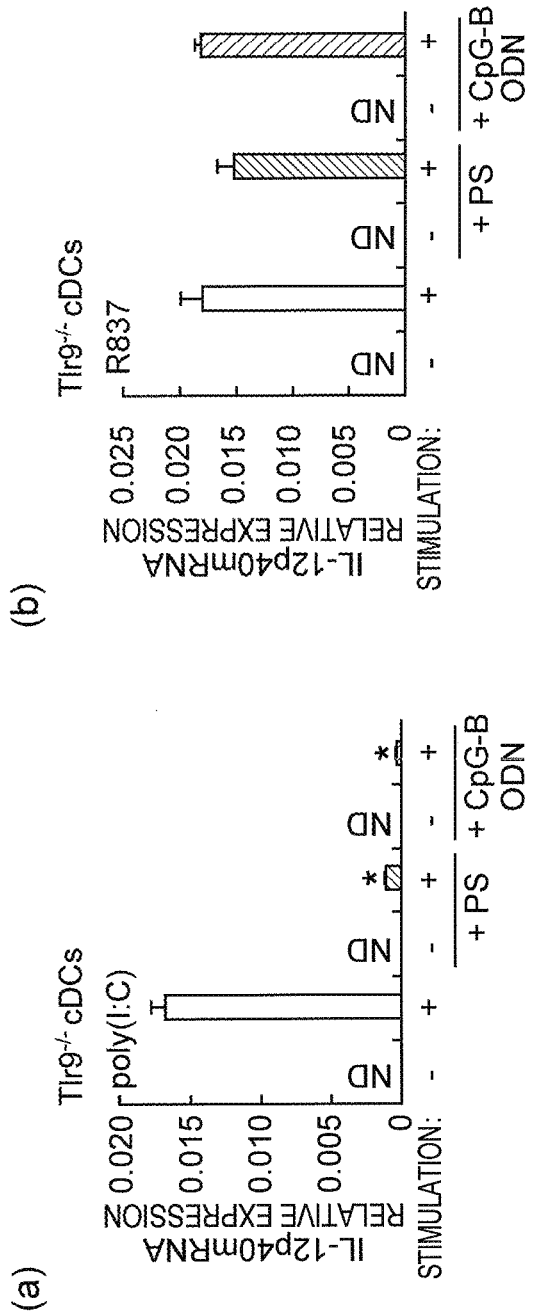
FIG. 40 is a set of graphs showing the results of Example 40.

Bone marrow-derived Tlr9$^{-/-}$ cDCs were pretreated with 5 μM PS or 1 μM CpG-B ODN for 30 minutes or not pretreated and then stimulated with 50 μg/mL of poly(I:C) (without lipotransfection) (FIG. 40a) or 25 μg/mL of R837 (FIG. 40b) for 4 hours. The expression levels of IL-12p40 mRNA were measured by quantitative RT-PCR. The results are shown in FIG. 40. All data were shown as mean±standard deviation (n=3). The symbol "*" indicates that the results of cells not subjected to the pretreatment are p<0.01 with respect to the results of pretreated cells. ND means not detected.

Example 41

Intracellular localization of HMGB1 and RIG-I was investigated. Expression vectors of CFP-tagged RIG-I (CFP-RIG-I) and YFP-tagged HMGB1 (YFP-HMGB1) were introduced, together with RFP-tagged Rab5 (RFP-Rab5) or without RFP-Rab5, into HeLa cells. At 16 hours after the gene transfer, the cells were stimulated with poly(I:C) for 2 hours, and fluorescence microscopic observation was performed using a laser scanning confocal microscope.

Figure 41:
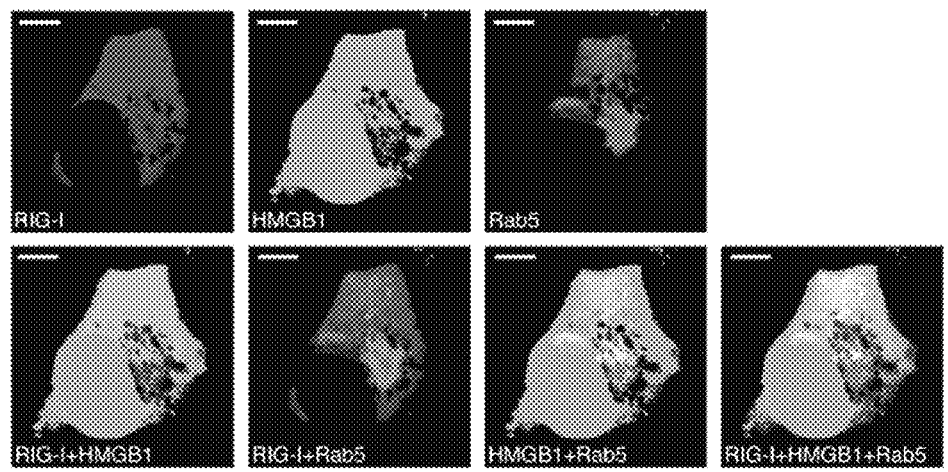
FIG. 41 is a set of photographs showing the results of Example 41.

FIG. 41 shows the fluorescence microscopy photographs of cells cotransfected with expression vectors (CFP-RIG-I, YFP-HMGB1 and RFP-Rab5). The upper and lower stages of FIG. 41 respectively show photographs of single (from the left to the right, RIG-I, HMGB1 and Rab5) and superposition (from the left to the right, CFP-RIG-I+YFP-HMGB1, CFP-RIG-I+RFP-Rab5, YFP-HMGB1+RFP-Rab5 and CFP-RIG-I+YFP-HMGB1+RFP-Rab5). The scale bar indicates 5 μm. Typical results observed in a large number of cells are shown. Both the RIG-I and HMGB1 partially overlapped the Rab5, which shows recruitment of RIG-I and HMGB1 to endosome membrane and probably activation of RIG-I by HMGB.

Example 42

Figure 42:
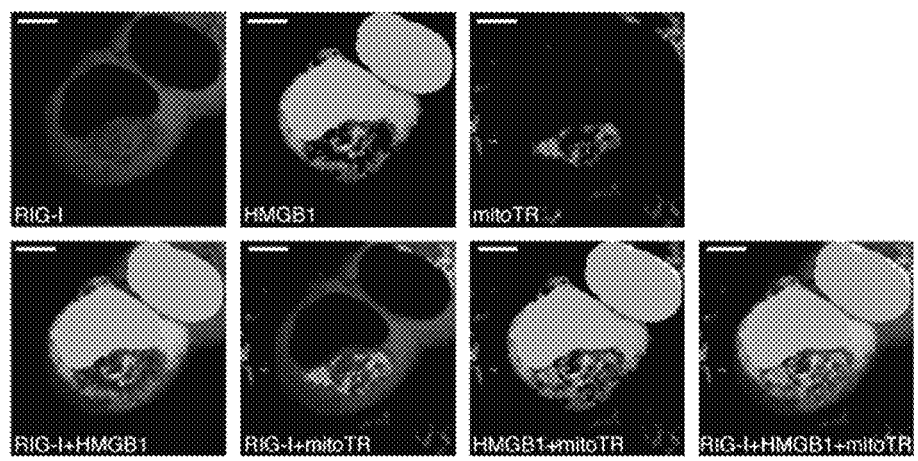
FIG. 42 is a set of photographs showing the results of Example 42.

The cells cotransfected with CFP-RIG-I and YFP-HMGB1 expression vectors were stimulated with poly(I:C) and were then stained with MitoTracker Deep Red 633 (mitoTR, Invitrogen Corporation) to perform fluorescence microscopic observation using a laser scanning confocal microscope. FIG. 42 shows fluorescence microscopy photographs of cells. The upper and lower stages in FIG. 42 respectively show photographs of single (from the left to the right, CFP-RIG-I, YFP-HMGB1 and mitoTR) and superposition (from the left to the right, CFP-RIG-I+YFP-HMGB1, CFP-RIG-I+mitoTR, YFP-HMGB1+mitoTR and CFP-RIG-I+YFP-HMGB1+mitoTR). The scale bar indicates 5 μm.

As shown herein, RIG-I overlapped mitoTR, but no overlapping between HMGB1 and mitoTR was observed at all. Together with the results shown in Example 41, the results are interpreted as follows. After recognition of poly(I:C) by HMGB1, RIG-I is activated and is localized in the mitochondria and interacts with IPS-1/MAVS therein.

These observations are "snapshot" in a series of actions of nucleic acid recognition and activation of immune response, and in the observations, a part of fractions of RIG-I interacts with HMGB1, and at the same time, another fraction dissociates from HMGB1 to binds to IPS-1/MAVS.

Figure 43:
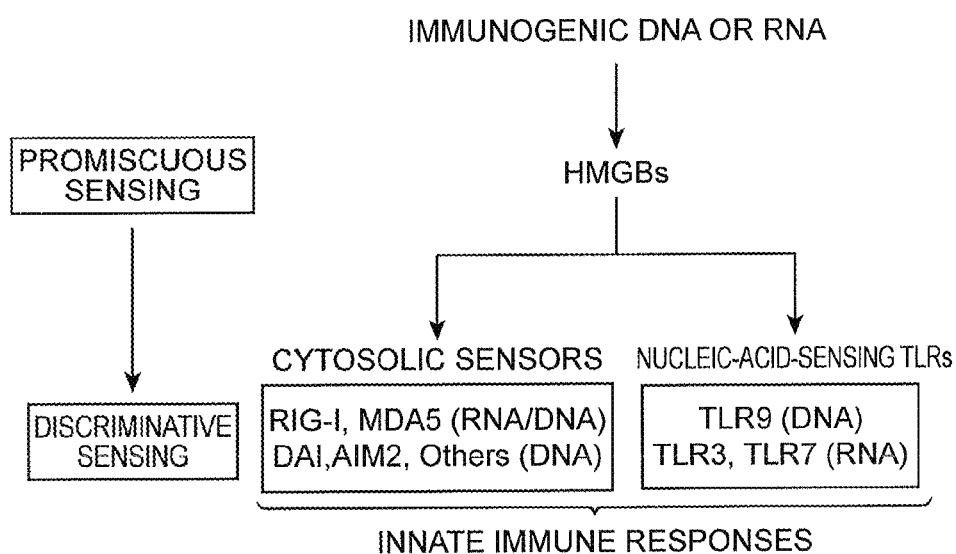
FIG. 43 is a schematic diagram illustrating the activation of an immune response mediated by an HMGB protein.

FIG. 43 shows a schematic diagram of the activation of an immune response mediated by nucleic acid, i.e., the activation of an immune response mediated by an HMGB protein, made on the basis of the results of the above-described Examples. All immunogenic nucleic acids bind to HMGB (promiscuous sensing), which is necessary for recognition by a specific pattern recognition receptor (discriminative sensing) for activating the subsequent immune response.

Example 43

The method of screening for an inhibitor of activation of an immune response mediated by an HMGB protein with an immobilized HMGB protein was evaluated using a microplate. A recombinant HMGB1 protein dissolved in PBS at a concentration of 5 μg/mL was dispensed by 100 μL in each well of a 96-well microplate and was left at 25° C. for 1 hour for immobilization. Each well was washed with PBS solution twice, and then 100 μL of a 2% BSA-PBS solution was added to each well, followed by incubation at 25° C. for 1 hour for blocking. Each well was washed with a PBS solution twice, and then 100 μL of a PBS solution only or a PBS solution containing 75 μg/mL of B-DNA, 100 μg/mL of poly(I:C), 100 ng/mL of LPS, or 25 μg/mL of R837 dissolved therein was added to each well, followed by incubation at 25° C. for 1 hour. Subsequently, each well was washed with a PBS solution twice, and then 100 μL of 1 μM B-DNA labeled with biotin at the 5' end or a PBS solution only was added to each well, followed by incubation at 25° C. for 1 hour. Subsequently, each well was washed with a PBS solution twice, then 100 μL of HRP-labeled anti-biotin antibody (R&D systems, Inc.) diluted 200 times with a PBS solution was added to each well, followed by incubation at 25° C. for 1 hour. Each well was washed with a PBS solution twice, and then 100 μL of a substrate solution (BD Biosciences) of HRP was added to each well, followed by color development at 25° C. for 15 minutes. The absorbance of each well was quantified with a microplate reader (Model 680, Bio-Rad Laboratories, Inc.). FIG. 45(*a*) shows the photographs of the microplate after color development, and FIG. 45(*b*) shows a graph of absorbance of each sample. All data were shown as mean±standard deviation (n=3).

(Effects of Phosphorothioate Oligonucleotide and PS on Activation of Immune Response Mediated by HMGB Protein)

Experiments using CpG-B(S), CpG-Rev(S) and CpG-M(S), which are phosphorothioate oligonucleotides and PS were carried out. FIG. 46 shows nucleotide sequences of these compounds. In FIG. 46, the underlined CG (CpG-B(S)), GC (CpG-Rev(S)) and GG (CpG-M(S)) are characteristic nucleotide sequences of the respective phosphorothioate oligonucleotides.

In Vitro Pull-Down Assay

Example 44

Figure 47:
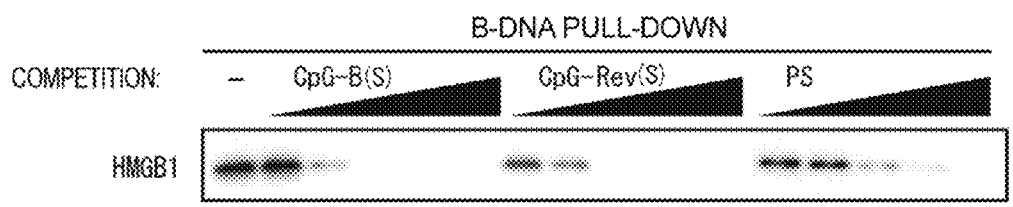
FIG. 47 is a set of photographs showing the results of Example 44.

As in Example 13, in vitro pull-down assay using recombinant HMGB1 and biotin-bound B-DNA was performed for 0.1, 0.5, 2.5, 12.5 and 62.5 μg/mL of CpG-B(S), CpG-Rev(S), CpG-M(S) and PS, as competitors. The results are shown in FIG. 47. CpG-Rev(S) and CpG-M(S) (data are not shown) showed higher competitivity than PS.

Inhibition of Activation of Immune Response Mediated by HMGB Protein

Example 45

Figure 48:
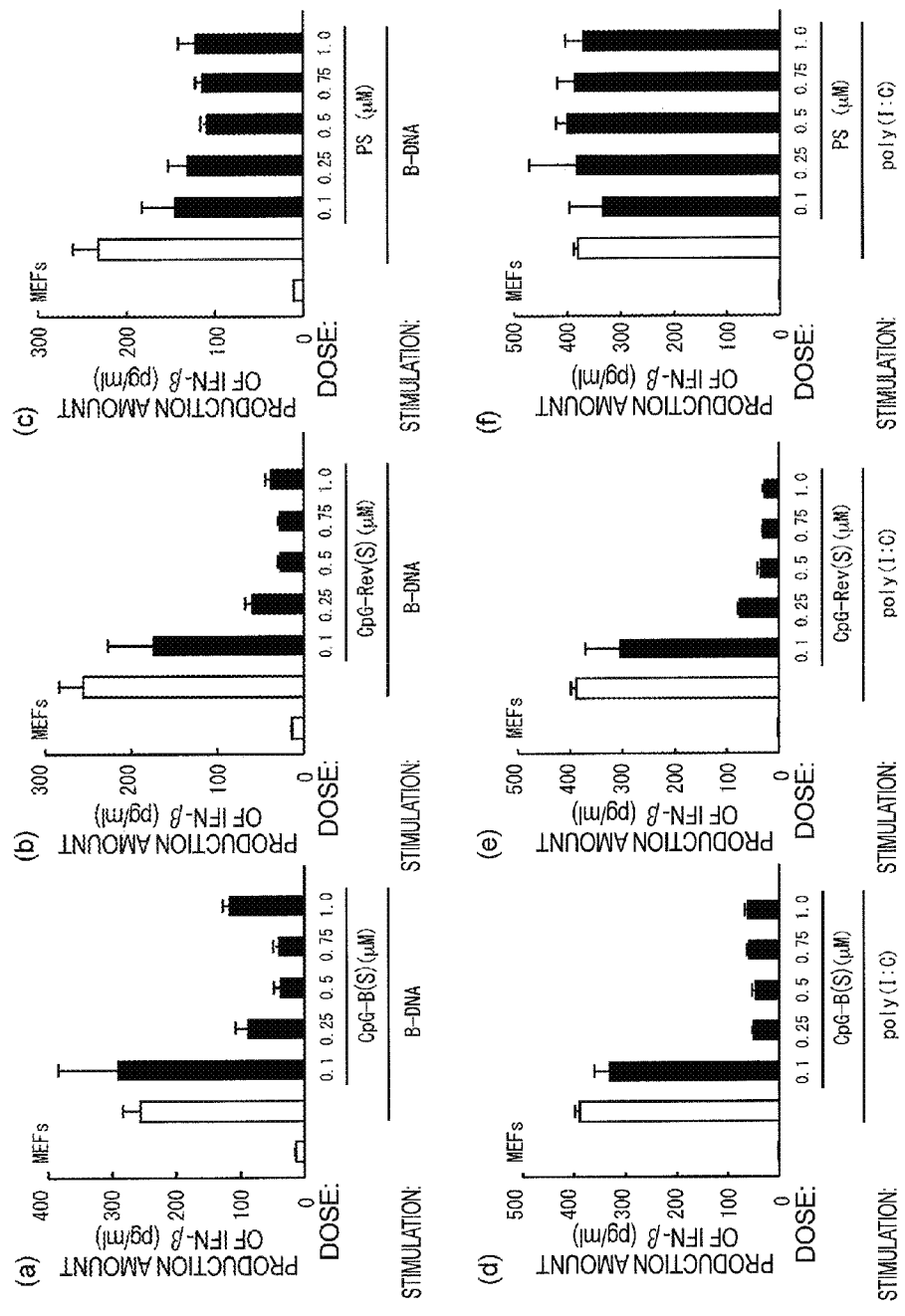
FIG. 48 is a set of graphs showing the results of Example 45.

CpG-B(S), CpG-Rev(S), or PS was added to the media of MEFs at a concentration of 0.1, 0.25, 0.5, 0.75, or 1 μM, and treatment was carried out for 1 hour. Subsequently, these MEFs were lipotransfected with 5 μg/mL of B-DNA or 5 μg/mL of poly(I:C) to stimulate for 24 hours, and production of IFN-β was measured by an ELISA method. The results are shown in FIG. 48. All data were shown as mean±standard deviation (n=3). (a) to (c) show the results of stimulation with B-DNA, and (d) to (f) show the results of stimulation with poly(I:C). As a result, in MEFs treated with CpG-B(S) (FIG. 48*a* and *d*) or CpG-Rev(S) (FIGS. 48*b* and *e*), the production of IFN-β were notably decreased. In addition, it was revealed that in the concentrations in this experiment, inhibition of production of IFN-β by MEFs in the case of using PS is weaker than that in the case of using CpG-B(S) or CpG-Rev(S) (FIGS. 48*c* and *f*).

From the results above, it was revealed that the presence of the base moiety is important for inhibiting the production of IFN-β by MEFs. It is known that the 8th and 9th nucleotides of CpG-B (SEQ ID NO: 1) being a sequence of CG is important for activating the immune response mediated by TLR9, but in MEFs treated with CpG-Rev(S) (SEQ ID NO: 38) in which this sequence was changed to GC and all phosphodiester linkages were replaced by phosphorothioate linkages, the production of IFN-β was notably decreased. It is believed from this result that the unmethylated CG sequence (5'-CG-3') is not important for inhibition of the activation of an immune response mediated by the HMGB protein and that (1) the presence of phosphorothioate linkage and (2) the presence of base are important.

Example 46

Figure 49:
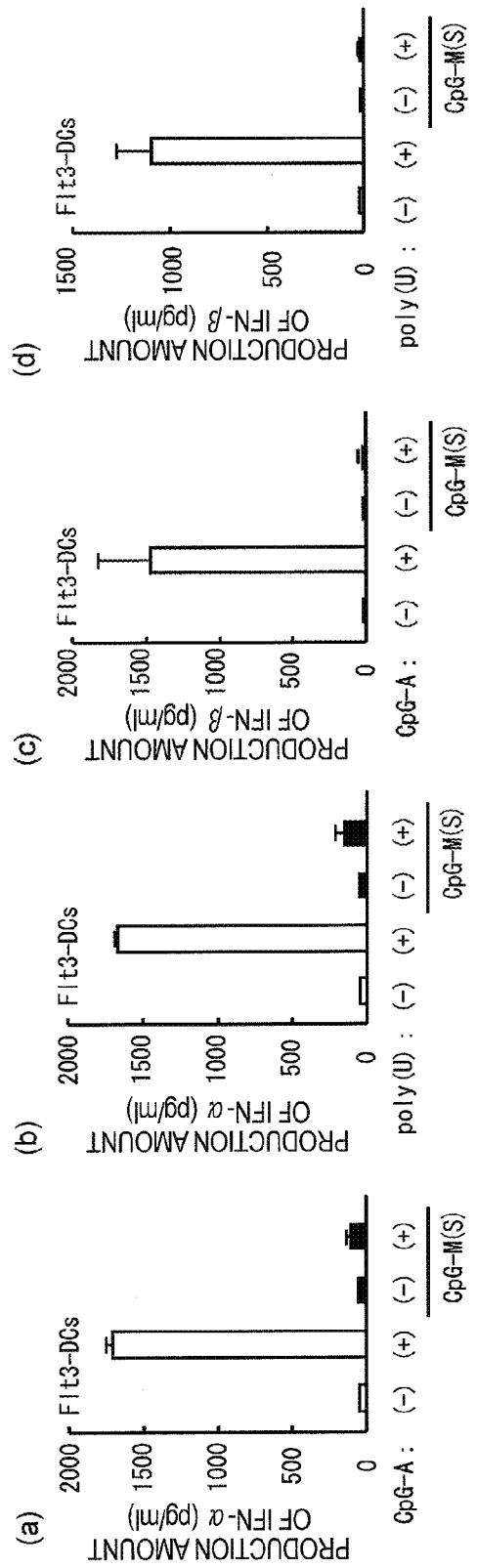
FIG. 49 is a set of graphs showing the results of Example 46.

Differentiation of wild-type mouse-derived bone marrow cells was induced with human Flt3L as described above to give pDCs. The pDCs (hereinafter, sometimes referred to as "Flt3-DCs") were treated in the presence of 3 μM of CpG-M(S) for 1 hour and were then lipotransfected with 1 μM of CpG-A (TLR9 agonist) or 5 μg/mL of poly(U) (TLR7 agonist) to stimulate for 24 hours, and the production of IFN-α and IFN-β was measured by the ELISA method. The results are shown in FIG. 49. (a) and (b) show the measurement results of production amount of IFN-α, and (c) and (d) show the measurement results of production amount of IFN-β. In addition, (a) and (c) show the results of stimulation with CpG-A, and (b) and (d) show the results of stimulation with poly(U). All data were shown as mean±standard deviation (n=3). As a result, it was revealed that in Flt3-DCs treated with CpG-M(S), the production of IFN-α and IFN-β when the Flt3-DCs are stimulated with CpG-A or poly(U) are notably inhibited.

In Vivo Septicemia Model

Example 47

LPS administration to mice is employed as a septicemia model. In the case of administering a lethal dose of LPS to a mouse, the blood concentrations of inflammatory cytokines, TNF-α, IL-1β and IL-6, increase shortly after the administration of LPS, reach their peaks 2 to 3 hours later, and then return to the base levels within several hours. Meanwhile, in tracking of survival progress of the mice, it takes 12 to 48 hours from the LPS administration until death of many individuals. The cytokine found to be present in the blood at a high level during this period is HMGB1. The blood level of HMGB1 does not change within 8 hours after LPS administration, then increases, and maintains a high level 16 to 36 hours after the administration. The importance of contribution of HMGB1 to lethality of septicemia is seen from the correlation between the blood concentration of HMGB1 and severity of septicemia and an increase in survival rate by administration of HMGB1 neutralizing antibody.

In addition, it is known that in a septicemia model, necrosis of hepatocytes occurs, and a possibility is suggested that DAMPs, such as nucleic acid, released by necrotic cells exacerbate the symptoms. The possibility of improving symptoms by inhibiting these so-called inflammation mediators was investigated.

Figure 50:
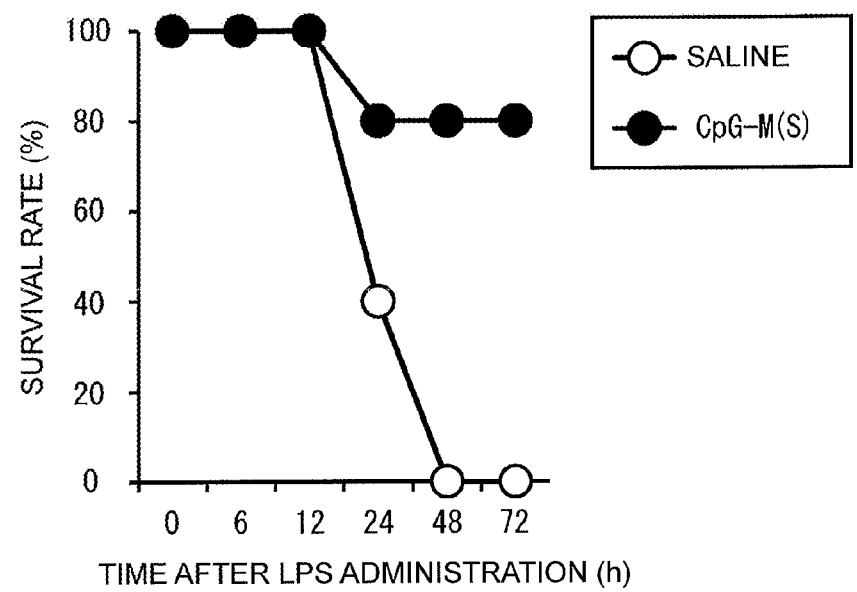
FIG. 50 is a graph showing the results of Example 47.

The effect of CpG-M(S) was investigated in a septicemia model that is initiated by intraperitoneal administration of LPS to C57BL/6 mice at 1.25 mg/mouse. At 1 hour before the administration of LPS, 100 μg/mouse of CpG-M(S) or saline was administered to each mouse through the tail vein, and the survival rate of mice was measured. The results are shown in FIG. 50. In mice administered with CpG-M(S), improvement in survival rate was recognized. It is believed that the administration of LPS causes cell death in, for example, the liver to release nucleic acids and that these nucleic acids induce the activation of an immune response mediated by an HMGB protein. Though it is not to stick to a specific theory, it is believed that such activation of an immune response mediated by an HMGB protein is inhibited by the administration of CpG-M(S).

As shown in FIG. 50, in the sample group (n=10) where LPS was injected after administration of CpG-M(S), 70% of individuals survived, whereas in the control group (n=10) where CpG-M(S) was not administered, all individuals died 12 to 48 hours after LPS injection.

Investigation of Nucleotide Sequence

Example 48

MEFs were pretreated for 1 hour with 1 μM of a phosphorothioate oligonucleotide (hereinafter, sometimes expressed as "poly(dA)(S)") including a nucleotide sequence of poly (dA) (purine base) of 5-mer, 10-mer (SEQ ID NO: 41), 15-mer (SEQ ID NO: 42), or 20-mer (SEQ ID NO: 43) or 1 μM of a phosphorothioate oligonucleotide (hereinafter, sometimes expressed as "poly(dC)(S)") including a nucleotide sequence of poly(dC) (pyrimidine base) of 5-mer, 10-mer (SEQ ID NO: 44), 15-mer (SEQ ID NO: 45), or 20-mer (SEQ ID NO: 46). Subsequently, the pretreated MEFs were stimulated by lipotransfection of B-DNA at a concentration of 5 μg/mL, and the induction of mRNA of IFN-β 3 hours or 6 hours later was investigated by RT-PCR.

Figure 51:
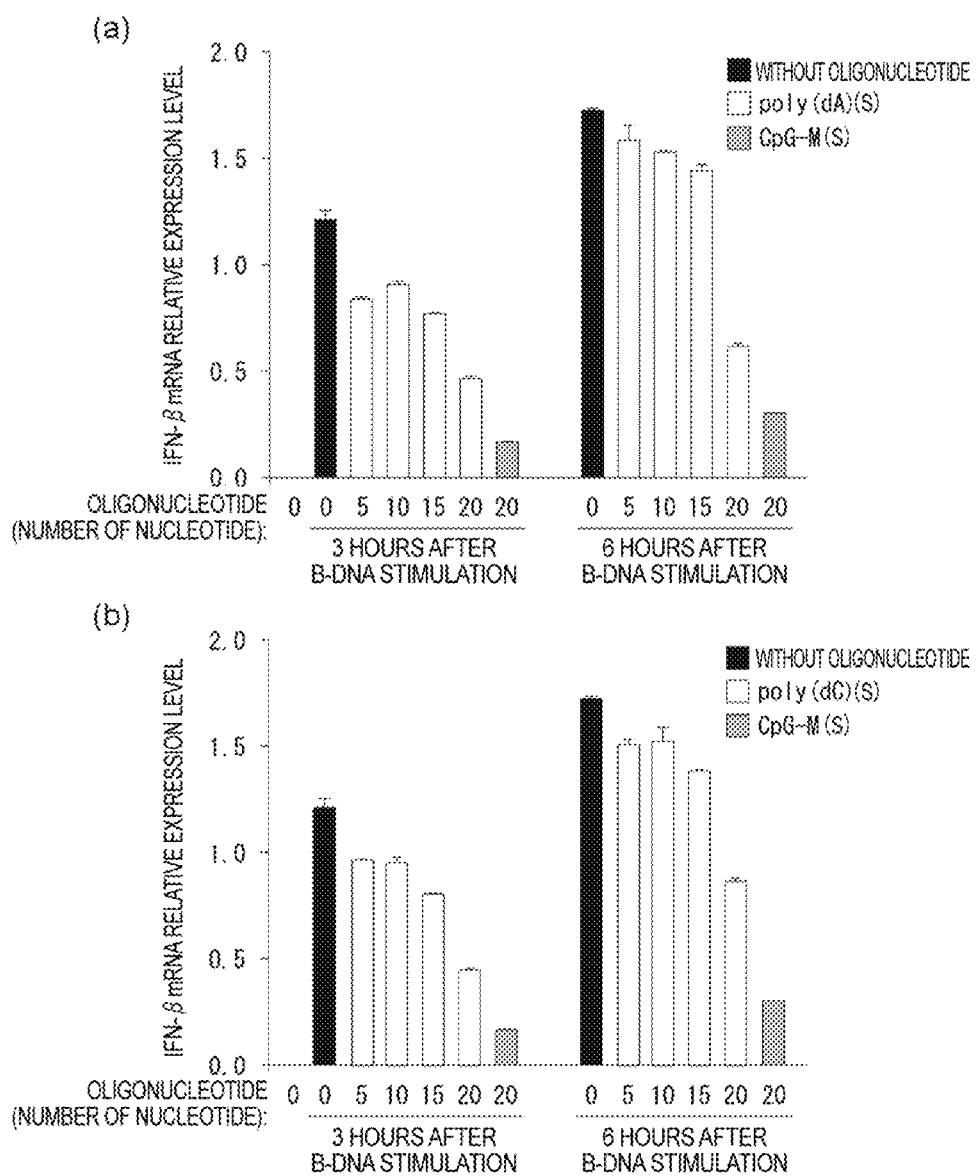
FIG. 51 is a set of graphs showing the results of Example 48.

The results are shown in FIG. 51. All data were shown as mean±standard deviation (n=3). (a) shows the results of poly (dA)(S) and (b) shows the results of poly(dC)(S). Cells pretreated with CpG-M(S) were used as a positive control and cells pretreated without addition of the oligonucleotide were used as a negative control. Both the poly(dA)(S) and poly(dC)(S) inhibited the induction of IFN-β mRNA by stimulation with B-DNA. In particular, the inhibition of induction of IFN-β mRNA was notable when a purine base, poly(dA)(S), was used. In addition, a phosphorothioate oligonucleotide having a length of 15-mer or more showed a high effect of inhibiting the induction of IFN-β mRNA.

(Search for Nonimmunogenic Oligodeoxyribonucleotide Inhibiting Nucleic Acid Recognition Receptor Signal)

Comparison of Ability of Inhibiting Production of Type I IFN by Various Oligodeoxyribonucleotides (ODNs)

Example 49

Figure 52:
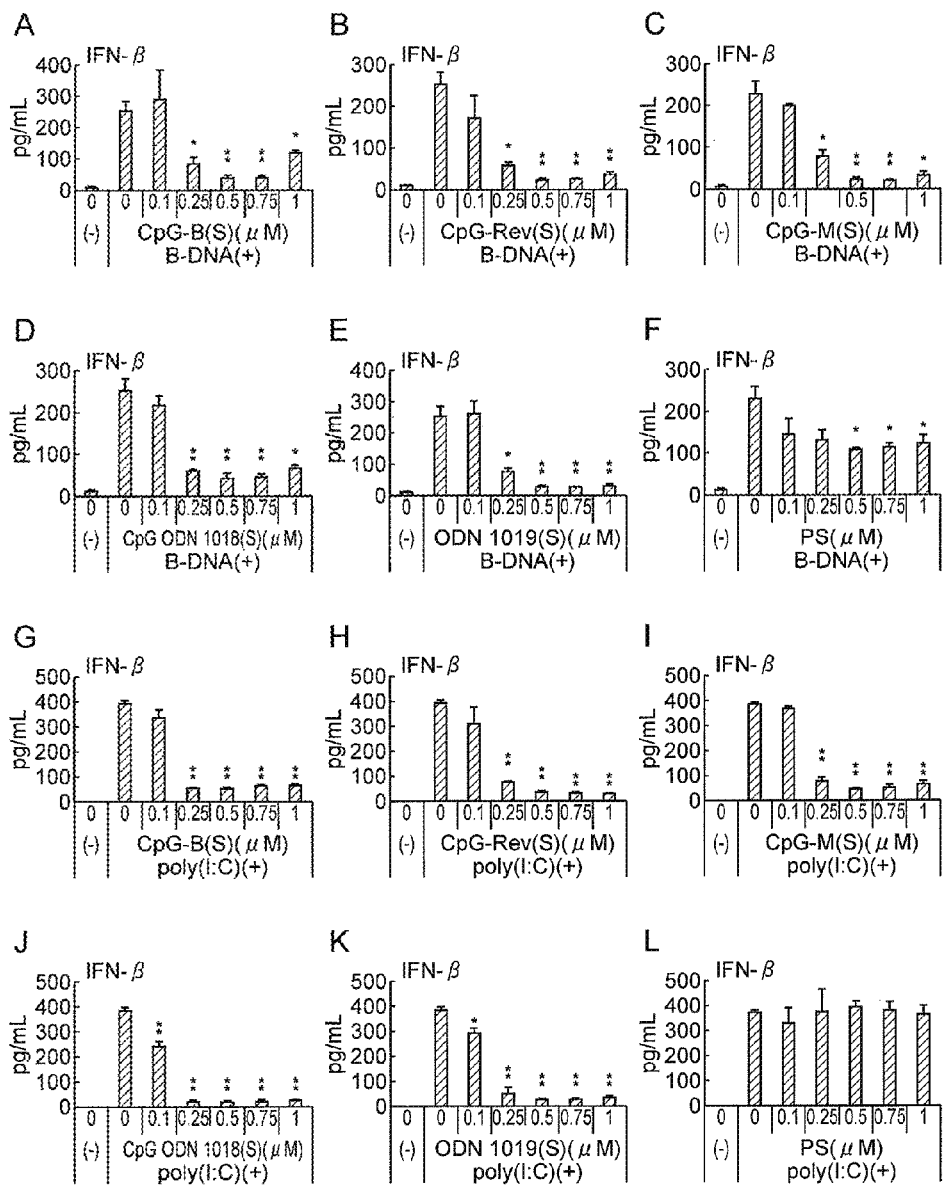
FIG. 52 is a set of graphs showing the results of Example 49.

It has been reported that when poly(dA:dT)•(dT:dA) (ds-DNA taking the B type conformation, hereinafter, referred to as "B-DNA"), or poly(I:C), which is a dsRNA, is introduced into mouse fetal fibroblasts (MEFs) by a lipofection method, type I IFN (IFN-α/β) and inflammatory cytokines are produced. Accordingly, first, immune response inhibition by addition of ODN to a medium in advance (hereinafter, referred to as "ODN pretreatment") was investigated using the production amount of type I IFN by nucleic acid stimulation as an index. The production amounts of type I IFN in MEFs were quantified by ELISA for the case of performing the pretreatment with various ODNs at 1 hour before the nucleic acid stimulation and the case of not performing the pretreatment. As a result, the production of type I IFN was inhibited depending on the increase in concentration of ODN in the medium when CpG-B(S), CpG-Rev(S), CpG-M(S), CpG ODN 1018(S), or ODN 1019(S) was used in the pretreatment. In addition, it was revealed that the ability of inhibiting the production of type I IFN in ODN(PS) not having the base and composed of only the phosphorothioate backbone is lower than that when the pretreatment was performed with ODN having the base. The results are shown in FIG. 52.

In more detail, MEFs were stimulated with 5 μg/mL of B-DNA (A-F) or 5 μg/mL of poly(I:C) (G-L) at 1 hour after the pretreatment with any of ODNs (CpG-B(S), CpG-Rev(S), CpG-M(S), CpG ODN 1018(S), ODN 1019(S) and PS) and the IFN-β in the supernatant of the culture 24 hours later was quantified by ELISA. The mean and the standard deviation of independent two samples were shown. In FIG. 52, the symbols "*" and "**" indicate that there are significant differences between the values of CpG-M(S)(+) and CpG-M(S)(−) at P<0.05 and P<0.01, respectively.

Example 50

Figure 53:
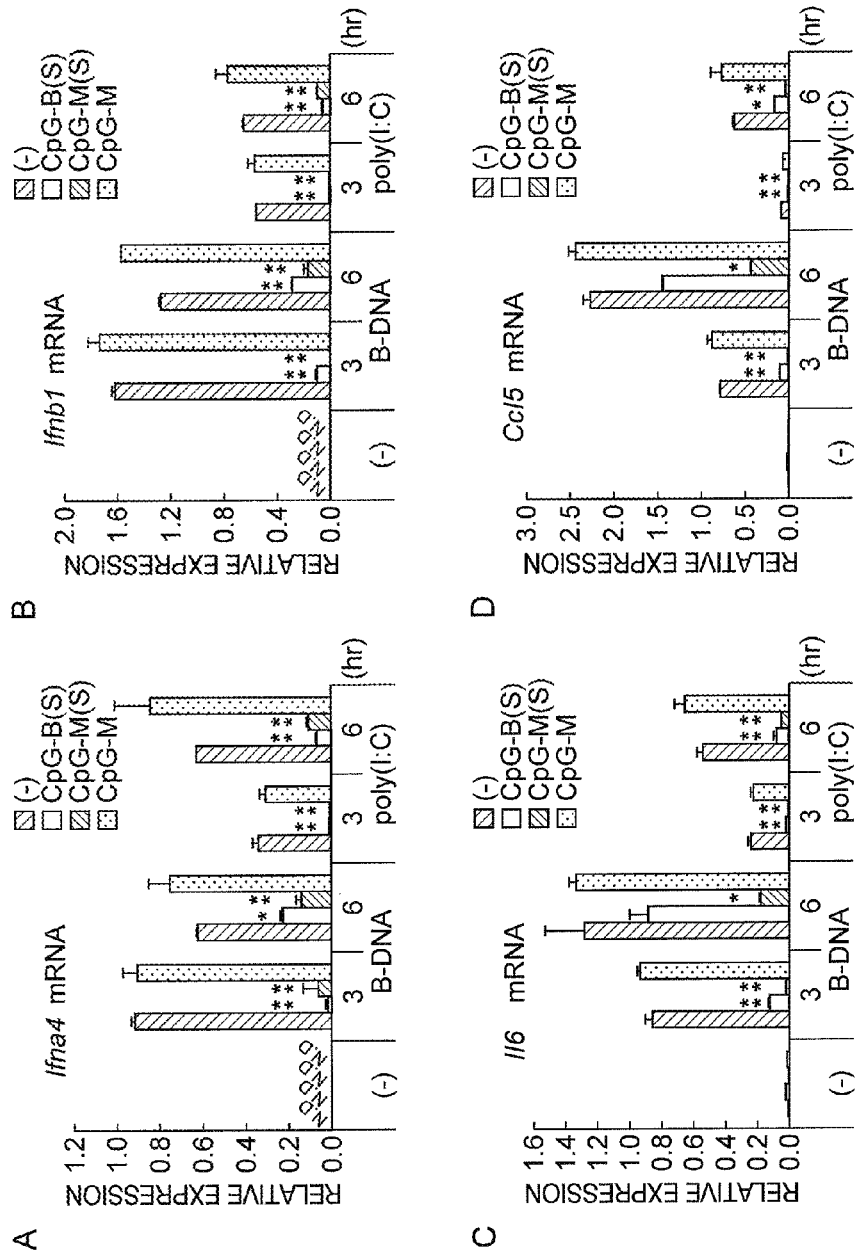
FIG. 53 is a set of graphs showing the results of Example 50.

It was investigated a possibility that the inhibition of protein synthesis is a cause of immune response inhibition by ODN. Regarding CpG-B(S) and CpG-M(S), induction of mRNAs of type I IFN and inflammatory cytokines in MEFs was investigated by quantitative RT-PCR. As a result, as shown in FIG. 53, the expression induction of mRNAs of both type I IFN and inflammatory cytokines was inhibited by using CpG-B(S) or CpG-M(S) in the pretreatment. Accordingly, it was suggested that these ODNs target upstream the mRNA expression induction to inhibit the immune response. In addition, in the pretreatment using ODN(CpG-M) having the same nucleotide sequence as that of CpG-M(S) and composed of a phosphodiester backbone, inhibition of expression induction of type I IFN and inflammatory cytokines was not observed, unlike in the pretreatment with CpG-M(S).

In more detail, 5 μg/mL of B-DNA or 5 μg/mL of poly(I:C) were introduced into MEFs for stimulation at 1 hour after the pretreatment with any of ODNs (CpG-B(S), CpG-M(S) and ODN(CpG-M) having the same sequence as that of CpG-M(S) and a phosphodiester backbone). Total RNA was collected at 3 hours and 6 hours after the stimulation, and the induction of mRNAs of (A) Ifna4, (B) Ifnb1, (C) Il6 and (D) Ccl5 was quantified by quantitative RT-PCR. The mean and the standard deviation of independent two samples were shown. In FIG. 53, N.D. indicates not detectable. The symbols "*" and "**" indicate that there are significant differences with the value of CpG-M(S)(−) at P<0.05 and P<0.01, respectively.

Analysis of Nucleic Acid Uptake Efficiency

Example 51

Figure 54:
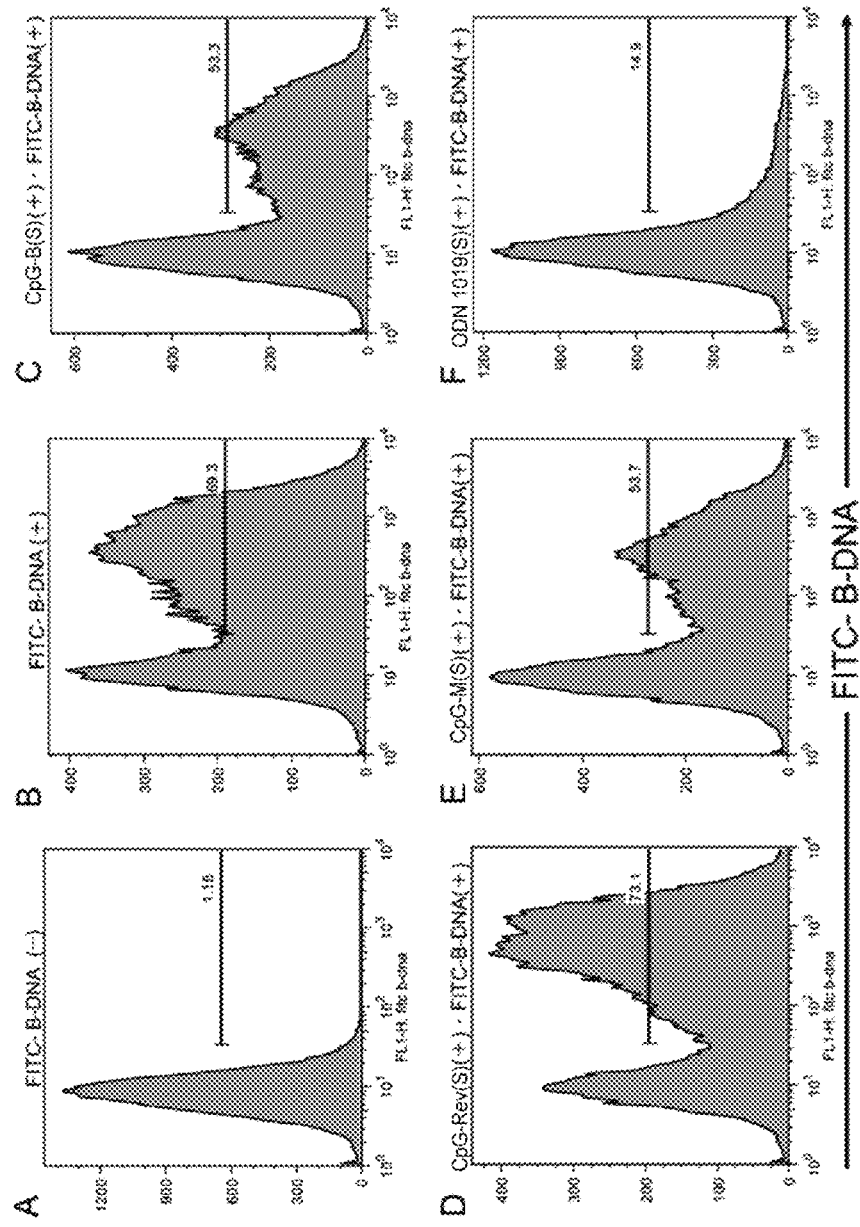
FIG. 54 is a set of graphs showing the results of Example 51.

The analysis in Example 50 showed that IFN production by stimulation with B-DNA or poly(I:C) is inhibited by subjecting the MEFs to ODN pretreatment. Regarding this result, it was investigated what kind of mechanism of the ODN inhibits the IFN production. In the stimulation of cells using B-DNA or poly(I:C), introduction by a lipofection method of nucleic acid is necessary. Consequently, in Example 50, it was suggested a possibility that the ODN inhibits the uptake by lipofection of B-DNA or poly(I:C) into cells and, as a result, inhibits the IFN production. Accordingly, in uptake of the B-DNA labeled with FITC at the 5' end into cells, the influence of the presence or absence of pretreatment with CpG-Rev(S), CpG-M(S), or ODN 1019(S), which is believed not to activate TLR9, on the uptake of the B-DNA was investigated. The results are shown in FIG. 54. In FITC-labeled B-DNA-introduced MEFs, the fluorescence derived from the FITC was observed by flow cytometry. The flow cytometric analysis was performed with FACS Calibur (Becton, Dickinson and Company). Under this condition, in samples pretreated with CpG-B(S), CpG-Rev(S), or CpG-M(S), which inhibits IFN production, (FIGS. 54, C, D and E), fluorescent intensity equivalent to or higher than that in the untreated control (FIG. 54, B) was observed, which revealed that the uptake of B-DNA was not inhibited. In contrast, in MEFs pretreated with ODN 1019(S) (FIG. 54, F), the number of cells emitting fluorescence derived from FITC was less than that in the control cell group (FIG. 54, B), which proved that the ODN 1019(S) inhibits the uptake by lipofection of B-DNA into MEFs.

In more detail, the fluorescence derived from FITC-labeled B-DNA taken up into MEFs was detected by flow cytometry for MEFs (A) not introduced with the FITC-labeled B-DNA without performing the pretreatment with various ODNs, MEFs (B) introduced with 3 μg/mL of FITC-labeled B-DNA only, and MEFs (C) to (F) introduced with 3 μg/mL of FITC-labeled B-DNA after the pretreatment for 1 hour with 1 μM of CpG-B(S), 1 μM of CpG-Rev(S), 1 μM of CpG-M(S), or 1 μM of ODN 1019(S), respectively. The number of cells was shown as a histogram with respect to the fluorescent intensity of the fluorescence derived from FITC on the abscissa. In FIG. 54, the number in each panel indicates the proportion of the FITC positive cells to the total cells.

The mechanism of how the ODN 1019(S) inhibits the introduction by lipofection of nucleic acid into cytoplasms is unclear, but the analysis of the style of the inhibitory action is not the main purpose here. Accordingly, in the specification, further analysis of the uptake-inhibiting mechanism by ODN 1019(S) is not performed, and CpG-M(S), which does not inhibit uptake of nucleic acid like CpG-B(S), was used in the following experiments.

Inhibition of Binding Between CpG-M(S) and HMGB Protein and Nucleic Acid Receptor Signaling Pathway Example 52

Figure 55:
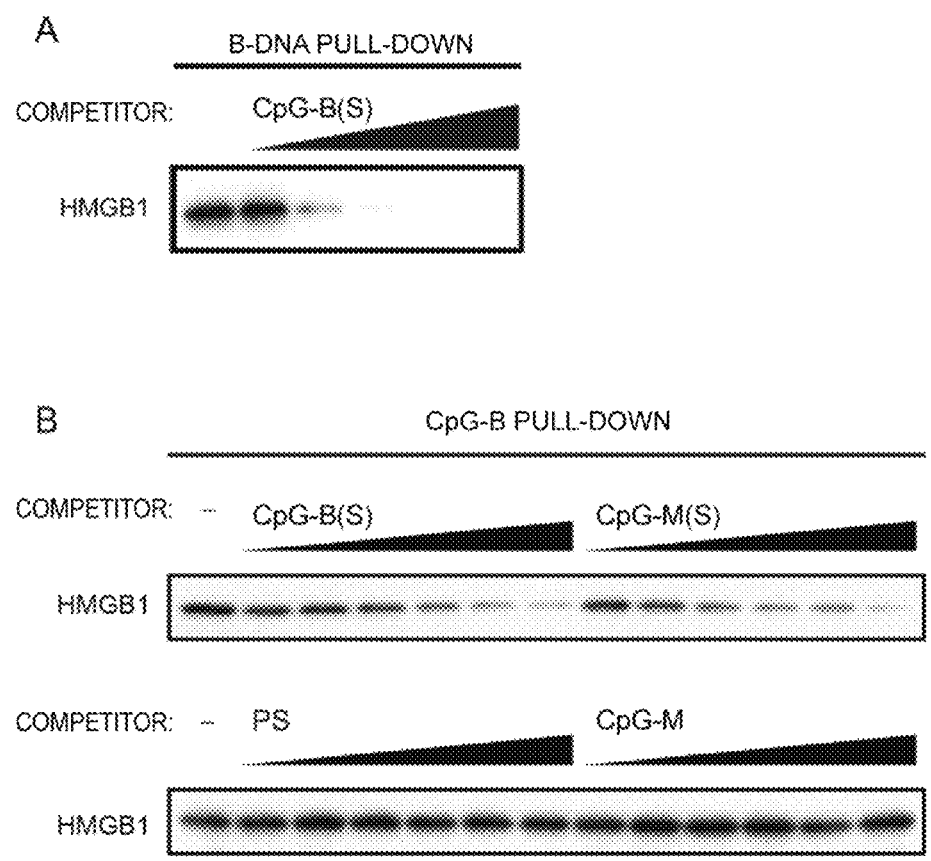
FIG. 55 is a set of photographs showing the results of Example 52.

It was clear from the results above that the inhibition of IFN production by CpG-M(S) is not performed by inhibition of nucleic acid uptake. Accordingly, it was investigated where is the site of action of inhibition by CpG-M(S). The analysis was carried out by focusing on the signaling molecules related to nucleic acid recognition. It is known that not only induction of type I IFN but also NF-κB pathway and MAP kinase pathway are activated by stimulation of B-DNA or poly(I:C), and it was investigated for a possibility of inhibiting activation of these signaling pathways by inhibiting the binding of B-DNA or poly(I:C) to HMGB protein. The binding of CpG-M(S) to HMGB protein was investigated by in vitro pull-down assay. HMGB1 bound to B-DNA, as shown in FIG. 55A, by purifying a recombinant protein of HMGB1 and mixing the protein with a biotin-labeled B-DNA. This binding was completely inhibited by adding CpG-B(S) as a competitor. Then, whether this strong binding between HMGB1 and CpG-B(S) can be inhibited by CpG-M(S) was investigated. As shown in FIG. 55B, it was revealed that the strong binding between CpG-B(S) and HMGB1 can be dose-dependently inhibited by adding CpG-M(S) to a mixture of biotin-labeled CpG-B(S) and the HMGB1 protein. Since the binding was inhibited equally to the case where CpG-B(S) not labeled with biotin was added, it was suggested that CpG-M(S) binds to HMGB1 with the same strength as that of CpG-B(S). At the same time, as shown in FIG. 55B, it was shown that CpG-M(S) binds to HMGB1 with a higher strength than ODN(PS) composed of only a phosphorothioate backbone and not having any base and ODN(CpG-M) having the same sequence as that of CpG-M(S) and a phosphodiester backbone.

In more detail, a final concentration of 0, 0.1, 0.5, 2.5, 12.5, or 62.5 μg/mL of CpG-B(S) as a competitor was added to 2 μg of a recombinant HMGB1 protein and a final concentration of 2.5 μg/mL of biotin-labeled B-DNA, and they were incubated (room temperature, 30 minutes). The biotin-labeled B-DNA was pulled down with streptavidin-bound magnetic beads, and HMGB1 in the coprecipitated protein was detected by Western blotting using an anti-HMGB1 antibody. The results are shown in FIG. 55A. In addition, a final concentration of 0, 1, 2, 4, 8, 16, or 32 μM of a competitor: CpG-B(S) not labeled with biotin, CpG-M(S), ODN(PS) composed of only a phosphorothioate backbone and not having any base, or ODN (CpG-M) having the same sequence as that of CpG-M(S) and a phosphodiester backbone, was added to 2 μg of the recombinant HMGB1 protein and a final concentration of 0.2 μM of biotin-labeled CpG-B(S). The biotin-labeled CpG-B was pulled down with streptavidin-bound magnetic beads, and HMGB1 in the coprecipitated protein was detected by Western blotting using an anti-HMGB1 antibody. The results are shown in FIG. 55B.

Example 53

In the investigation of Example 49, CpG-M(S), which is believed to have a high binding affinity to HMGB1, showed a stronger ability of inhibiting the IFN induction by nucleic acid stimulation than PS composed of only a phosphorothioate backbone; and in the investigation of Example 50, CpG-M(S) inhibited the mRNA induction of type I IFN and inflammatory cytokines, whereas CpG-M did not, therefore, it was believed that the immune response inhibitory action by CpG-M(S) arises from inhibition of binding and signaling to an immunoreceptor downstream by binding of an immunogenic nucleic acid to an HMGB protein through strong binding of CpG-M(S) to the HMGB protein. According to this hypothesis, the inhibitory action of CpG-M(S) should act on not only the induction of type I IFN, but also activation pathways of NF-κB and MAP kinase. Accordingly, subsequently, the inhibitory action of CpG-M(S) on activation of these transcription factors and signaling molecules by nucleic acid stimulation was investigated.

It has been reported that IFN regulatory factor 3 (IRF3), which is a transcription factor, plays an important role in induction of type I IFN by stimulation with nucleic acid such as B-DNA or poly(I:C). IRF3 is present in cytoplasm as a monomer in the absence of stimulation and is known to form a homodimer by activation with phosphorylation or the like and is transported into nuclei. Accordingly, the activation of IRF3 was investigated using phosphorylation as an index.

Figure 56:
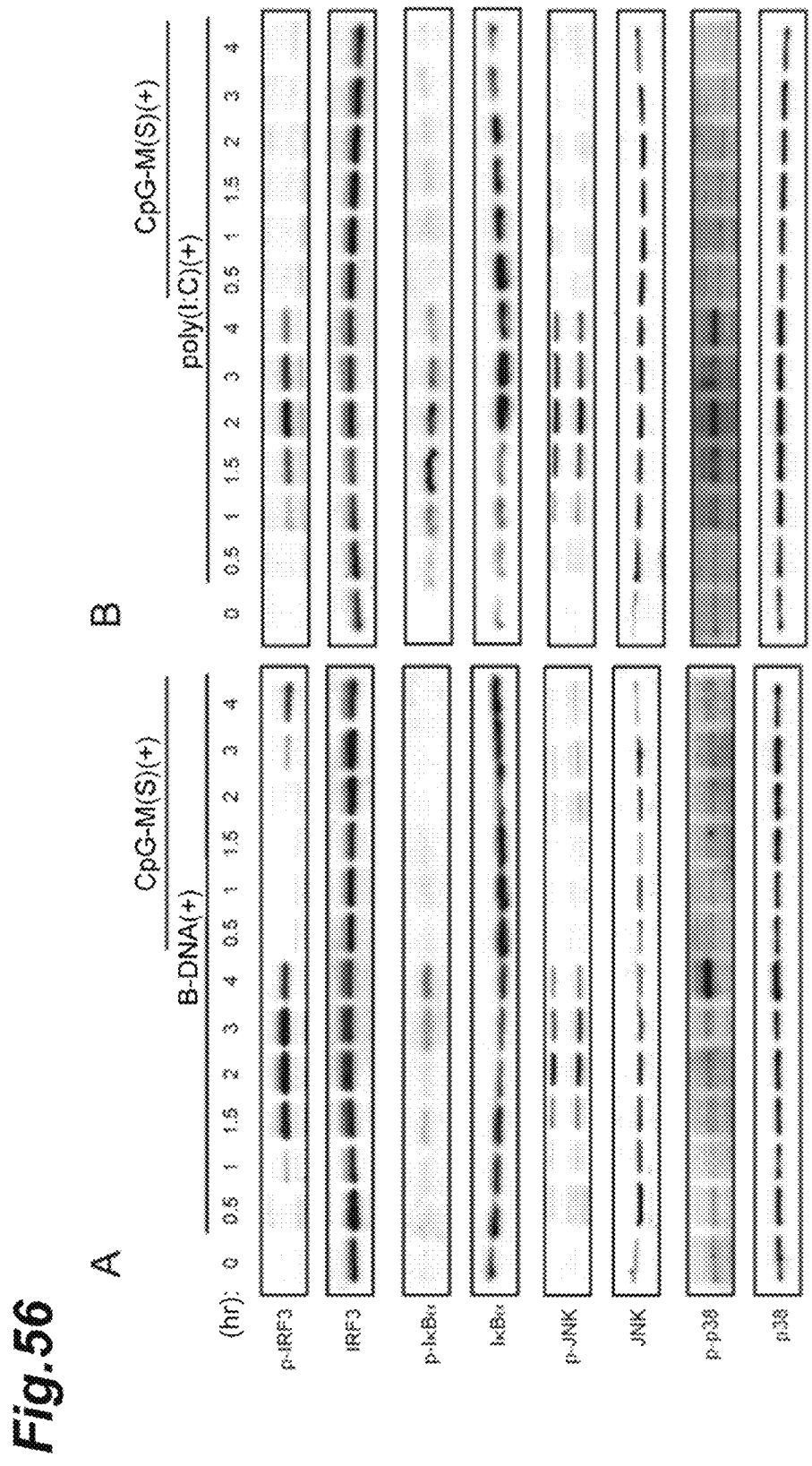
FIG. 56 is a set of photographs showing the results of Example 53.

The results are shown in FIG. 56. It was revealed that the phosphorylation of IRF3 by nucleic acid stimulation is notably inhibited by the pretreatment with CpG-M(S). Subsequently, the activation of the NF-κB pathway was investigated using the phosphorylation of IκBα as an index, and the activation of MAP kinase pathway was investigated using phosphorylation of c-Jun N-terminal kinase (JNK) and p38 as indices. As a result, it was revealed that the activation of these transcription factors and signaling molecules was also notably decreased by the pretreatment with CpG-M(S). It was suggested from the above that CpG-M(S) binds to an HMGB protein and thereby inhibits the binding of B-DNA and poly (I:C) to the HMGB protein and inhibits the signaling pathway by the natural immunoreceptor stimulation.

In more detail, 1 μg/mL of B-DNA (A) or 1 μg/mL of poly(I:C) (B) was introduced into cytoplasms of MEFs derived from C57BL/6J mice pretreated with 1 μM of CpG-M(S) for 1 hour or not pretreated for stimulation. Protein samples were collected at 0.5, 1, 1.5, 2, 3 and 4 hours after the stimulation, and phosphorylation of IRF3, IκBα, JNK and p38 (p-IRF3, p-IκBα, p-JNK and p-p38) was detected by Western blotting.

Investigation of Involvement of TLR9 in Inhibitory Action of CpG-M(S)

Example 54

Figure 57:
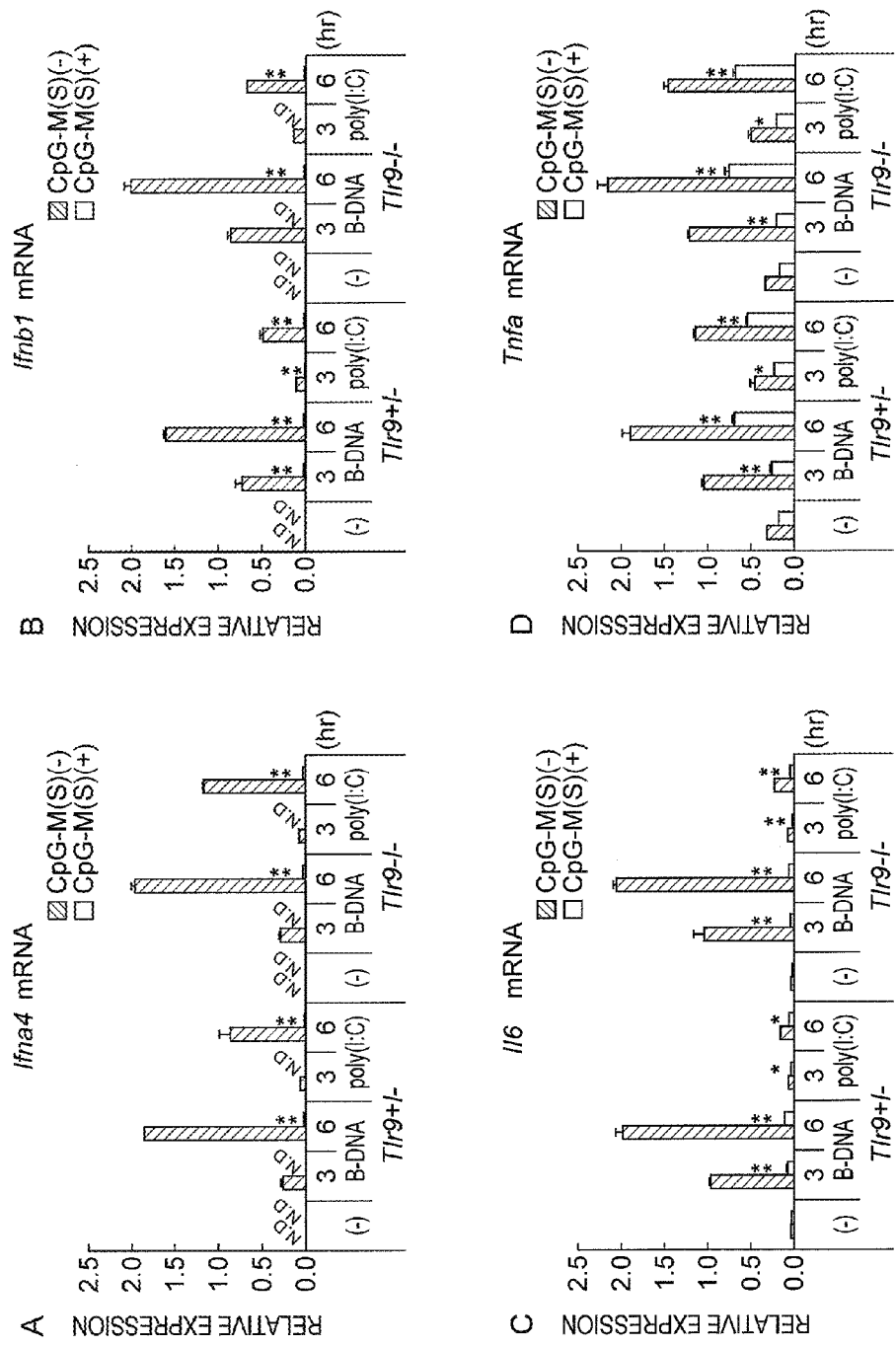
FIG. 57 is a set of graphs showing the results of Example 54.

It was revealed from the results above that CpG-M(S) does not affect the uptake of B-DNA into cells and inhibits the activation of signaling pathway downstream intracellular nucleic acid recognition receptor. It is strongly suggested that CpG-M(S) inhibits the immune response by targeting the HMGB protein. Incidentally, CpG-M(S) has a sequence different from that of CpG-B(S), a TLR9 agonist, by one nucleotide only. Accordingly, it was investigated whether CpG-M(S) can inhibit the activation of an immune system by nucleic acid stimulation also in a cell type expressing TLR9. In addition, a possibility that CpG-M(S) itself is recognized by TLR9 and thereby acts as an agonist was investigated. Whether the response to intracellular nucleic acid stimulation is inhibited by CpG-M(S) treatment was investigated using cDCs derived from a Tlr9 gene deficient (Tlr9$^{-/-}$) mouse and a control (Tlr9$^{+/-}$) mouse. As shown in FIG. 57, expression of type I IFN and inflammatory cytokine genes was induced equally in both cDCs by stimulating these mouse-derived cDCs with B-DNA or poly(I:C). On this occasion, the expression induction of type I IFN and inflammatory cytokine genes was inhibited by the pretreatment with CpG-M(S) in both of Tlr9$^{+/-}$ cDC and Tlr9$^{-/-}$ cDC. It was revealed by the above that CpG-M(S) inhibits the immune system activation by nucleic acid stimulation also in cell types other than MEF. In addition, it is surmised that this inhibitory action does not depend on the signal of TLR9 and may be probably achieved by the binding between the HMGB protein and CpG-M(S) upstream TLR9. Furthermore, since neither type I IFN nor inflammatory cytokines was induced in the case of not stimulating with B-DNA and poly(I:C) and adding CpG-M(S) only, it was revealed that CpG-M(S) does not have immunogenicity, unlike the CpG-B(S) being an agonist of TLR9.

In more detail, cDCs derived from a Tlr9 gene deficient (Tlr9$^{-/-}$) mouse and a control (Tlr9$^{+/-}$) mouse were pretreated with 1 μM of CpG-M(S) or were not pretreated as a control, and 5 μg/mL of B-DNA or 5 μg/mL of poly(I:C) was introduced into the cells 1 hour later for stimulation. Total RNA was collected at 3 and 6 hours after the stimulation, and the induction of mRNAs of (A) Ifna4, (B) Ifnb1, (C) Il6 and (D) Tnfa was measured by quantitative RT-PCR. The mean and the standard deviation of independent two samples were shown. In FIG. 54, N.D. indicates not detectable. The symbols "*" and "**" indicate that there are significant differences between the values of CpG-M(S)(+) and CpG-M(S)(-) at P<0.05 and P<0.01, respectively.

Investigation of Inhibition by CpG-M(S) of TLR Pathway

Example 55

Figure 58:
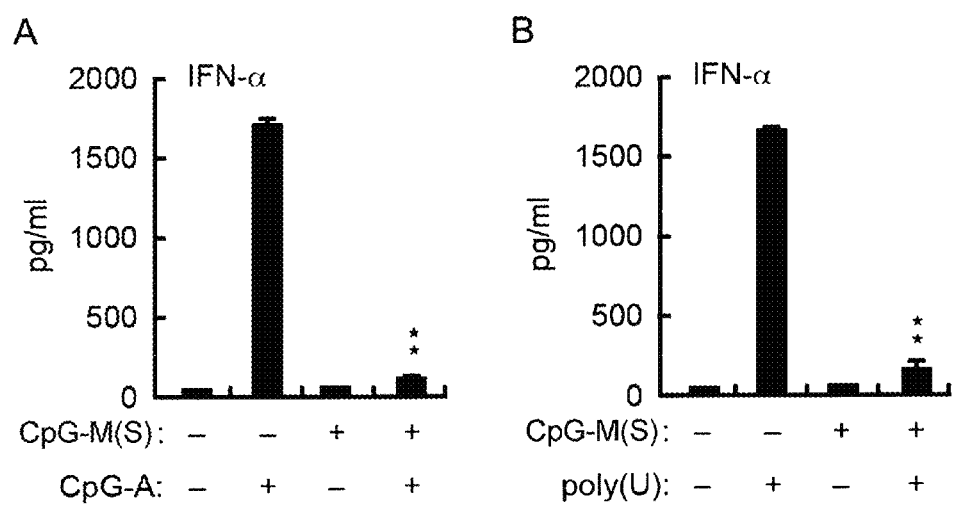
FIG. 58 is a set of graphs showing the results of Example 55.

It was believed from the results in Example 54 that CpG-M(S) inhibits the immune system activation by nucleic acid stimulation by targeting further upstream TLR9. Accordingly, it was investigated whether signaling pathways downstream TLR7, which is a membrane receptor similarly recognizing nucleic acid, can be similarly inhibited by CpG-M(S). CpG-M(S) does not have immunogenicity as an agonist of TLR9. Accordingly, whether the induction of type I IFN in nucleic acid recognition by TLR7 or TLR9 is inhibited by CpG-M(S) was investigated using pDCs, which are cells that highly express TLR7 and TLR9 and produce a large amount of type I IFN by recognition of ssRNAs, the respective ligands thereof, and DNA having CpG motif. As shown in FIG. 58, the production of IFN-α was induced by stimulating pDCs with CpG-A, which is a TLR9 ligand, or poly(U), which is a TLR7 ligand, and this production was inhibited by the pretreatment with CpG-M(S).

In more detail, pDCs derived from C57BL/6J mice pretreated with 3 μM of CpG-M(S) or not pretreated were stimulated with (A) 1 μM of CpG-A, which is a TLR9 ligand, or (B) 5 μg/mL of poly(U), which is a TLR7 ligand, and IFN-α in the culture supernatant was quantified by ELISA 24 hours later. The symbol "**" indicates that there is a significant difference between the values of CpG-M(S)(-) and (+) at P<0.01.

Example 56

Figure 59:
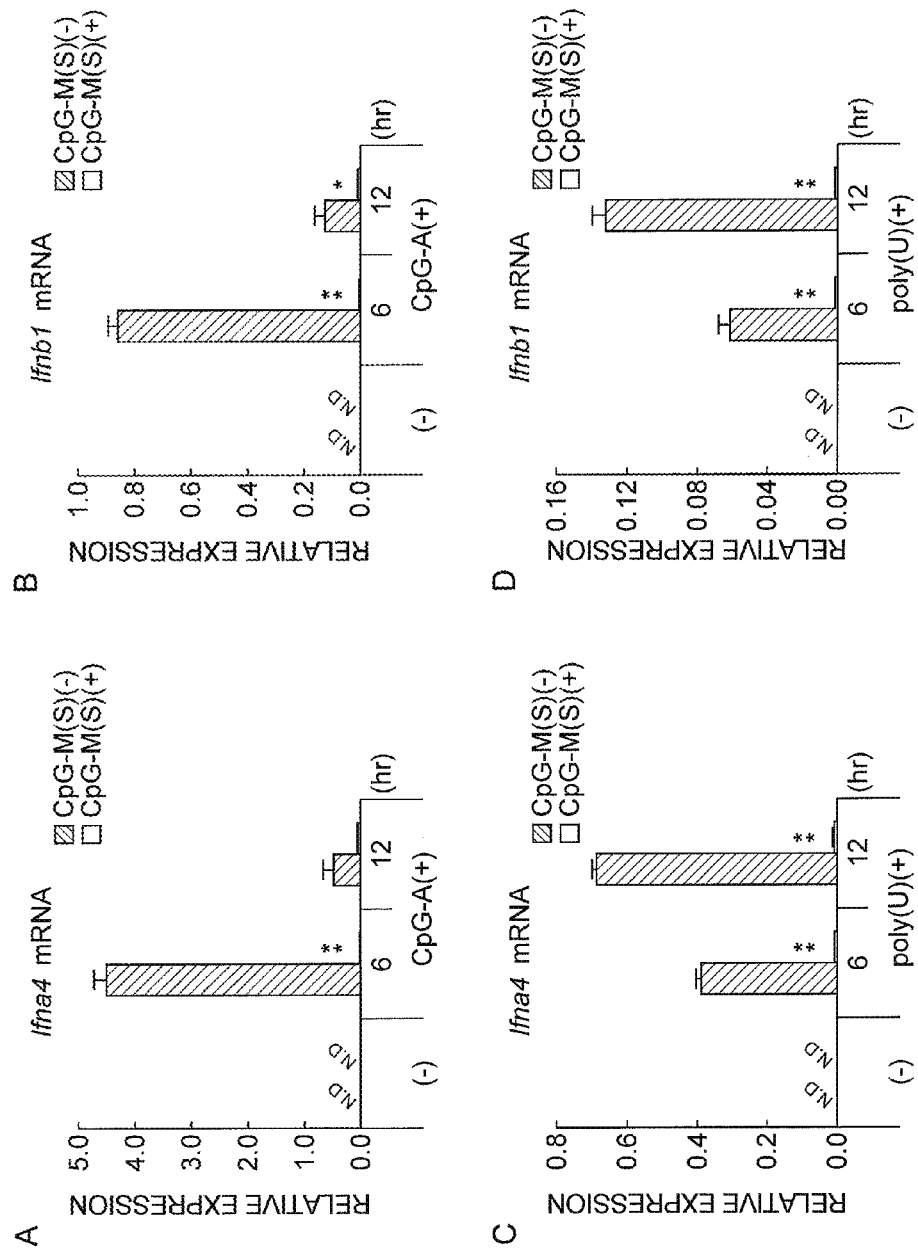
FIG. 59 is a set of graphs showing the results of Example 56.

Then, the expression induction of type I IFN gene was analyzed by quantitative RT-PCR, and as shown in FIG. 59, the expression of type I IFN gene was inhibited at the mRNA level in both cases of stimulating with any of CpG-A and poly(U). It was suggested from this that CpG-M(S) inhibits the induction of type I IFN by targeting the mechanism common to nucleic acid recognition by TLR7 and TLR9.

In more detail, in pDCs derived from C57BL/6J mice pretreated with 10 μM of CpG-M(S) or not pretreated, mRNA induction of (A) Ifna4 and (B) Ifnb1 when the pDCs were stimulated with 1 μM of CpG-A and mRNA induction of (C) Ifna4 and (D) Ifnb1 when the pDCs were stimulated with 5 μg/mL of poly(U) were quantified by quantitative RT-PCR. The mean and the standard deviation of independent two samples were shown in both cases. N.D. indicates not detectable. The symbols "*" and "**" indicate that there are significant differences between the values of CpG-M(S)(+) and CpG-M(S)(-) at P<0.05 and P<0.01, respectively.

(Inhibition of Activation of Adaptive Immune System by Nucleic Acid Stimulation of CpG-M(S) and Evaluation in Disease Model)

The results above demonstrated the ability of CpG-M(S) of inhibiting the innate immune response in vitro. The natural immunity, which promptly recognizes pathogen-associated molecular patterns (PAMPs) and self-tissue damage-associated molecular patterns (DAMPs) and responds thereto, is important in the point of promptly eliminating non-self in the living body. At the same time, however, activation of an adaptive immune system and initiation of an immune response with higher specificity are also important roles of natural immunity.

Accordingly, first, whether or not the innate immune response in vivo and the adaptive immune response activated thereby are inhibited by CpG-M(S) was investigated using the activation of CD8+ T cells as an index. Furthermore, in addition to the inhibition of the adaptive immune system by CpG-M(S), considering that CpG-M(S) does not have immunogenicity as shown in the results above, the influences of CpG-M(S) in disease models such as experimental autoimmune encephalomyelitis (EAE) and septicemia were investigated.

(Inhibition by CpG-M(S) of Activation of Antigen-Specific CD8+ T Cell)

Example 57

Figure 60:
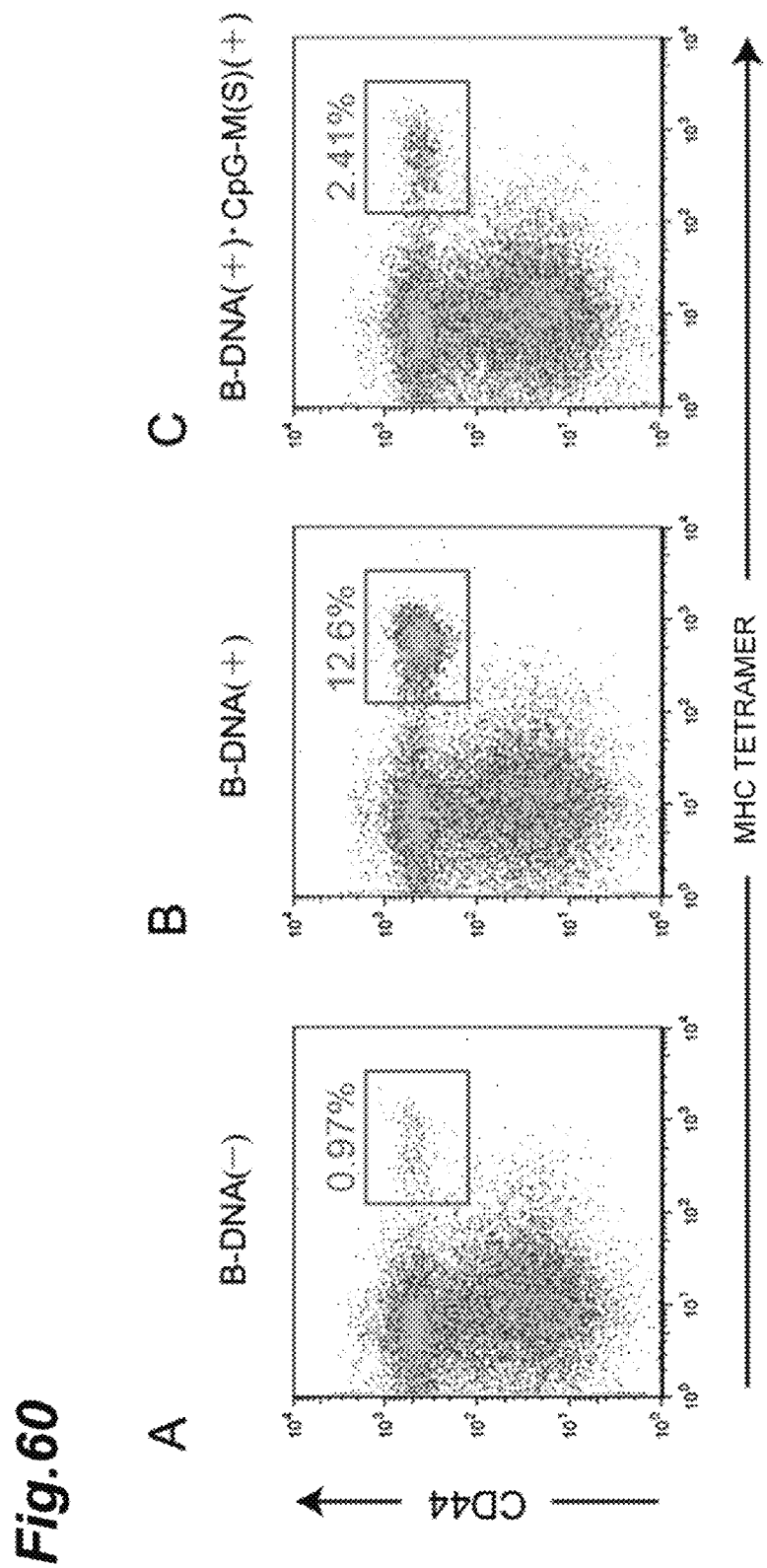
FIG. 60 is a set of graphs showing the results of Example 57.

The activation of an innate immune system is closely related in the activation of an adaptive immune system. It is well known that an adaptive immune system specific to an antigen is activated by administration of the antigen and an adjuvant, and it is believed that the adjuvant activates an innate immune system to express a costimulator in, for example, dendritic cells and enhances antigen presentation to T cells by accelerating maturation. There are many reports on that an antigen-specific adaptive immune system is initiated by nucleic acid and administration of an antigen, and here, whether or not CpG-M(S) can inhibit the activation of the adaptive immune system was investigated using B-DNA as the nucleic acid and ovalbumin (OVA)-specific CD8+ T cells, which are induced by administration of OVA as an antigen, as an index. In immunization of mice with OVA and B-DNA, a group of administering CpG-M(S) and a group of not administering CpG-M(S) were prepared. Splenocytes were prepared on the 8th day after the immunization, and CD8+ T cells that specifically react with OVA were detected by flow cytometry using an OVA-specific MHC class I tetramer. As shown in FIG. 60, the proportion of the OVA-specific CD8+ T cells (12.6%) was significantly increased in the case of immunization with OVA together with B-DNA compared to that (0.97%) in the case of sensitization with OVA only. On this occasion, this proportion was notably decreased in the mice administered with CpG-M(S) (2.41%). That is, it was shown that CpG-M(S) can inhibit the activation of the adaptive immune system by nucleic acid.

In more detail, (A) OVA only (B-DNA(−)), (B) OVA and B-DNA (B-DNA(+)), or (C) OVA, B-DNA, and also CpG-M(S) (B-DNA(+)•CpG-M(S)(+)) was intraperitoneally administered to C57BL/6J mice. The proportion of OVA-specific CD8+ T cells in the spleen on 8 days later was analyzed by flow cytometry using an MHC class I tetramer. FIG. 60 shows gated cells for the CD8+ T cells. In addition, fractions of CD44 positive and MHC tetramer positive are surrounded by red frames. The figures each indicate the proportion of the fraction of CD44 positive and MHC tetramer positive in the gated cell population for the CD8+ T cells.

Evaluation of CpG-M(S) in EAE Pathological Conditions

Example 58

EAE is one animal model of human multiple sclerosis (MS). MS is an inflammatory, autoimmune, demyelinating disease of the central nervous system, and mouse EAE can be developed by administering myelin-derived peptide (MOG peptide 35-55, Operon, hereinafter referred to as "MOG peptide") together with complete Freund's adjuvant (CFA) to a normal mouse for immunization. The pathological findings common to MS and EAE are infiltration of B cells, T cells and macrophages into the central nervous system and neurological disorders caused thereby, and it is also reported that nucleic acid is involved in exacerbation of the pathological conditions.

Figure 61:
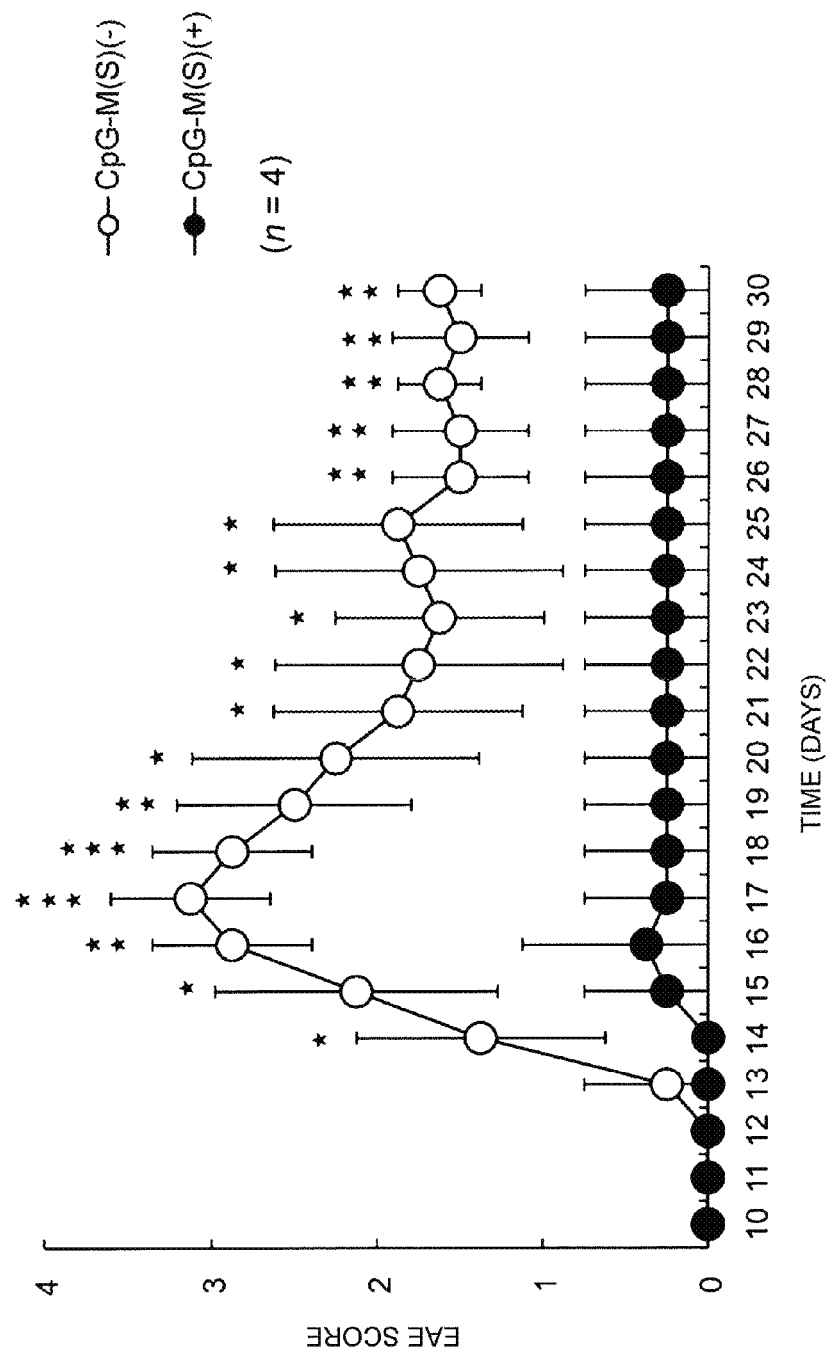
FIG. 61 is a graph showing the results of Example 58.

Accordingly, on the basis of an idea that the pathological conditions of EAE can be relieved by administering CpG-M(S), experiments were carried out. In EAE, the progress of autoimmune inflammation can be evaluated by scoring the severity of neurological disorders such as paralysis of the tail and the limbs. The pathological scores of EAE were determined on the basis of the criteria shown in Table 1. The MOG peptide and CFA were subcutaneously injected in the lower back of mice for immunization. 1 week after the injection, CpG-M(S) (n=4) or PBS as control (n=4) was administered three times every three days, and then the pathological conditions were evaluated. The results are shown in FIG. 61. In the CpG-M(S) administration group, the pathological conditions of EAE were notably relieved compared to the control group. That is, it was shown that CpG-M(S) can relieve the pathological conditions of EAE.

In more detail, 1 week after the administration of the MOG peptide and CFA to the lower back of C57BL/6J mice, CpG-M(S) (CpG-M(S)(+), n=4) or PBS (CpG-M(S)(−), n=4) as the control was administered by tail vein injection three times every three days. In FIG. 61, the progress of pathological score of each group was shown by mean and standard deviation with respect to the number of days from administration of the MOG peptide on the abscissa. The symbols "*", "" and "*" indicate that there are significant differences between the values of CpG-M(S)(+) and CpG-M(S)(−) at $P<0.05$, $P<0.01$ and $p<0.001$, respectively.

TABLE 1

| | EAE score |
|---|---|
| Grade | Clinical condition |
| 0 | Normal |
| 0.5 | Hanging down of the tip of the tail |
| 1 | Paralysis of the tail |
| 2 | Deficiency of cooperative motility; dysmotility of hindlimb |
| 2.5 | Paralysis of one hindlimb |
| 3 | Paralysis of both hindlimbs |
| 3.5 | Paralysis of both hindlimbs and weakness of forelimbs |
| 4 | Paralysis of both forelimbs |
| 5 | Moribund condition |

Effect of CpG-M(S) of Inhibiting Immune System Activation by Necrotic Cell

Example 59

Figure 62:
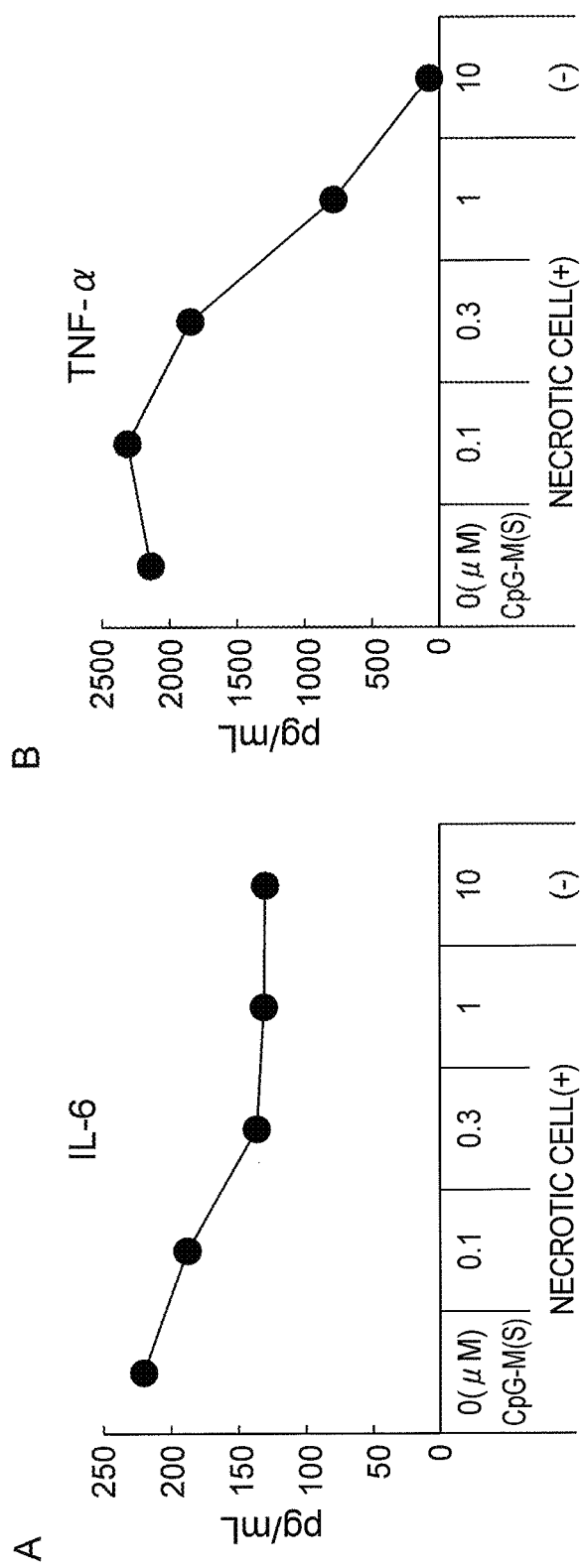
FIG. 62 is a set of graphs showing the results of Example 59.

Then, it was investigated whether the activation of the immune system initiated by necrotic cells (excessive immune response to dead cells) can be inhibited by CpG-M(S). Necrosis was induced by repeating freezing and thawing of a mouse macrophage cell line, J774.1 cells, the necrotic cells were mixed with splenocytes in the presence or absence of CpG-M(S), and the production of inflammatory cytokines, IL-6 and TNF-α, was investigated by ELISA. As shown in FIG. 62, in the splenocytes pretreated with CpG-M(S), the results demonstrated that the production amounts of IL-6 and TNF-α were decreased depending on an increase in the concentration of the CpG-M(S) in the pretreatment. Though it is unclear if these results are caused by inhibition of the response in the target splenocytes or by direct inhibition of the inflammatory mediator released by necrotic cells, it was believed that the results show that CpG-M(S) can inhibit the immune system activation initiated by necrotic cells.

FIG. 62 shows the results of quantitative measurement by ELISA of (A) IL-6 and (B) TNF-α in culture supernatant 24 hours after inducing necrosis in J774.1 cells and mixing the cells with splenocytes in the presence or absence of CpG-M(S).

(Consideration)

(Search for ODN Inhibiting Immune Response and Analysis of Site of Action of CpG-B(S))

CpG-B(S) has one CG motif, and an immune response in a cell is initiated by recognition of this CG by TLR9. Therefore, CpG-B(S) does not initiate the immune response in MEFs expressing TLR9 at a low level, but it is difficult to expect to have the effect of inhibiting the immune response only in the living body, where pDCs and macrophages expressing TLR9 are also present. Accordingly, in order to avoid recognition by TLR9, CpG-Rev(S) and CpG-M(S) having GC and GG, respectively, in place of CG in the sequence of CpG-B(S) were synthesized and were confirmed to have an effect of inhibiting the production of type I IFN in MEFs, like CpG-B(S). Similarly, ODN 1019(S) having GG or AG in place of CG in CpG ODN 1018(S) having a CG motif was synthesized and was similarly investigated, and both CpG ODN 1018(S) and ODN 1019(S) showed inhibition of production of type I IFN in MEFs.

In the subsequently performed investigation of B-DNA uptake inhibition by various ODNs, a large difference was observed between CpG-Rev(S) or CpG-M(S) and ODN 1019(S). In CpG-Rev(S) and CpG-M(S), the B-DNA uptake was not influenced, but in MEFs pretreated with ODN 1019(S), only a small amount of B-DNA was uptaken into the cells, which suggested that ODN 1019(S) inhibits the uptake of B-DNA into cells. Though the detail of the uptake inhibition mechanism is unclear, it is believed that the entire sequence of ODN and the ODN steric structure caused therefrom influence in any way. Since the immune system inhibition effect by the uptake inhibition is not the focus of this study, further investigation using ODN 1019(S) was not performed, and the analysis was carried out by focusing on CpG-M(S).

It was investigated how CpG-M(S) inhibits the response against nucleic acid stimulation and where the site of action of the inhibition is. It was supposed that CpG-M(S) strongly binds to an HMGB protein to inhibit its function and thereby inhibits the immune response against nucleic acid. First, analysis by in vitro pull-down assay showed that CpG-M(S) strongly binds to HMGB1. Furthermore, the hypothesis that response to nucleic acid stimulation is inhibited by inhibiting the function of the HMGB protein by CpG-M(S) was supported by the following four results obtained by this study.

(i) Activation of main transcription factors activated by intracellular nucleic acid stimulation and all of IRF3, NF-κB and MAP kinase, which are signaling molecules, was notably inhibited by the pretreatment with CpG-M(S). This suggests that CpG-M(S) acts upstream the activation pathways of these transcription factors and signaling molecules. In addition, since the signaling pathway activation by stimulation with each of B-DNA and poly(I:C) was inhibited by CpG-M(S), it is believed that CpG-M(S) targets a structure common to recognition mechanisms of both DNA and RNA in cells.

(ii) The inhibitory action by CpG-M(S) was also observed in Tlr9 gene deficient cDCs. That is, it is suggested that the site of action of inhibition by CpG-M(S) is further upstream the signaling system of TLR9. Considering together with the report on that HMGB1 is necessary also for activation of the signaling pathway of TLR9, it was believed that CpG-M(S) inhibits HMGB1 upstream TLR9.

(iii) In pDC, type I IFN induction by stimulation with each of TLR7 and TLR9 was inhibited by CpG-M(S). Based on this, together with the results (i) and (ii), it is believed that CpG-M(S) targets a structure common to both the intracellular nucleic acid recognition mechanism and the nucleic acid recognition by TLR. This is believed to support the hypothesis that CpG-M(S) inhibits HMGB1.

(iv) It was revealed that the binding of CpG-M(S) to HMGB1 is very strong compared to that of PS composed of only a phosphorothioate backbone and not having the base moiety. Though PS also binds to HMGB1, the binding affinity is low, and it was also revealed that the inhibitory action of immune response against nucleic acid stimulation is also very weak compared to that of CpG-M(S). This suggests that the strength of binding between ODN and HMGB1 correlates to the strength of the inhibitory action of immune response of ODN and is believed to support the hypothesis that this inhibitory action is initiated by inhibition of HMGB1 by ODN.

It is believed that the following three factors are necessary as factors of nucleic acid for strongly binding to an HMGB protein.

(i) The binding of an oligo DNA having a phosphorothioate linkage backbone to HMGB1 is stronger than that of an ordinary oligo DNA having a phosphodiester linkage backbone.

(ii) The binding of ODN having the base moiety to HMGB1 is stronger than that of ODN composed of only the backbone and not having the base. On this occasion, it is believed that the binding affinity does not depend on the nucleotide sequence. Actually, it has been found that even in the case of using ODN having base moieties composed of adenine and thymine only and having a phosphorothioate backbone in the pretreatment, the immune response by nucleic acid stimulation is inhibited. However, it is also supposed a possibility that TLR9 recognizes the CG motif in the oligo DNA, like CpG-B(S), to activate the immune response. Incidentally, in CpG-M(S) not having the CG motif, immune system activating ability was not recognized.

(iii) The inhibitory action by ODN needs a chain length of 15-mer or more. The inhibitory actions of ODNs having the phosphorothioate backbone and a base moiety composed of adenine or thymine only and having a chain length of 5-mer, 10-mer, 15-mer, or 20-mer was investigated, and an inhibition effect was observed in the ODN of 20-mer, but inhibition was hardly recognized in the ODNs having a chain length equal to or less than that. It is surmised from these findings that it is important to have a phosphorothioate backbone and also have a base moiety and a chain length of about 20-mer for binding of oligo DNA and an HMGB protein and inhibitory action to immune response. The demonstration of these characteristics is expected to be useful information for considering an inhibitor targeting an HMGB protein.

Then, considering that CpG-M(S) does not have immune system activating ability, the use of CpG-M(S) as an inhibitor of relieving the pathological conditions in which nucleic acid is involved was investigated. It was revealed that the activation of OVA-specific CD8$^+$ T cells in immunization of mice with OVA as an antigen together with B-DNA is notably inhibited by administration of CpG-M(S). That is, it was revealed that CpG-M(S) not only inhibits the activation of the innate immune system, but also can inhibit the adaptive immune system in vivo. Regarding the activation of antigen-specific CD8$^+$ T cells, it was reported that stimulation with CD40 and TLR synergistically acts, and the stimulation of TLR on this occasion is believed to be a factor for inducing type I IFN. Accordingly, the inhibition of activation of CD8$^+$ T cells observed in CpG-M(S) administration is believed to be caused by that CpG-M(S) inhibits the activation of the innate immune system in, for example, dendritic cells and thereby inhibits the adaptive immune system to be subsequently induced. However, other influences, such as a possibility that CpG-M(S) directly sensitizes CD8$^+$ T cells, cannot be strictly denied.

From the viewpoint of that CpG-M(S) can inhibit not only the innate immune system but also the adaptive immune system, CpG-M(S) in an EAE disease model, which is a model of an autoimmune disease, was evaluated. As a result, it was revealed that the pathological conditions of EAE were dramatically improved by administration of CpG-M(S). In the protocol used in this analysis, an MOG peptide was mixed with CFA and was administered to normal mice. Accordingly, activation of MOG peptide-specific MHC class II-restricted CD4$^+$ T cells is induced. However, it has been reported that in the pathological conditions of EAE, not only T cell response, but also various factors contribute to exacerbation thereof, and involvement of signaling through TLR9 is also pointed. In relieving pathological conditions of EAE, it was also suggested a possibility that CpG-M(S) inhibits such a nucleic acid recognition receptor signal.

(Role of HMGB1 as Inflammatory Cytokine and CpG-M(S))

It was investigated a possibility that administration of CpG-M(S) to an individual inhibits the inflammatory cytokine function of HMGB1 and inhibits the pathological conditions of septicemia, as an anti-HMGB1 antibody. As a result of evaluation using a septicemia model caused by LPS administration to mice, it was revealed that the survival rate is notably improved by administration of CpG-M(S) in advance. In cells such as MEFs and RAW264.7 cells, it has been found that CpG-M(S) does not inhibit the production itself of cytokines by LPS stimulation, and it is suggested that CpG-M(S) does not inhibit the LPS stimulation itself to cells.

As a possibility of the site of action of CpG-M(S), it is believed that CpG-M(S) assembles with HMGB1 released into the blood by LPS administration to inhibit the function of HMGB1 as an inflammatory mediator. Alternatively, since it is known that the LPS administration causes necrosis of hepatocytes, it is also believed that CpG-M(S) inhibits the immune response initiated by nucleic acid released by, for example, necrosis.

Accordingly, administration of CpG-M(S) to J774.1 cells to which necrosis was induced and which was mixed with splenocytes inhibited inflammatory cytokines such as IL-6 and TNF-α, which are produced in splenocytes when ODN is not administered. Since the prepared necrotic cell solution is thought to contain not only HMGB1 flew out from cells and nucleic acid derived from necrotic cells but also complexes thereof, at this stage, the results do not contradict both the two hypotheses described above. It is believed that in the future, administration of CpG-M(S) to a living body can be taken into consideration by clarifying whether CpG-M(S) inhibits HMGB1 as an inflammatory mediator by binding thereto, whether CpG-M(S) inhibits the immune system activation by necrotic cells, or whether there is a possibility of participation of the both, and also a possibility of involvement of nucleic acid.

INDUSTRIAL APPLICABILITY

According to the present invention, an inhibitor based on a novel principle of the activation of an immune response mediated by an HMGB protein, i.e., an antigen-specific adaptive immune system, multiple sclerosis, an excessive immune response to dead cells, an organ transplant rejection, an autoimmune disease, inflammatory bowel disease, an allergy, septicemia, tumor growth by inflammation and an inflammatory disease caused by a nucleic acid-containing pathogen, etc. is provided. In addition, a method of screening for an inhibitor or enhancer of activation of an immune response mediated by an HMGB protein is provided.

REFERENCE SIGNS LIST

1: HMGB protein, 2: positive control material, 3: test substance, 4: biotin-labeled B-DNA, 5: anti-biotin antibody, 6: substrate

The invention claimed is:

1. A method of inhibiting activation of an immune response mediated by a high-mobility group box (HMGB) protein, the method comprising
administering to a subject in need thereof a phosphorothioate oligonucleotide of 20 to 40 nucleotides in length in an amount effective to inhibit an immune response in the subject, wherein
the phosphorothioate oligonucleotide binds to HMGB protein,
the phosphorothioate oligonucleotide does not have an unmethylated CG sequence, and
the phosphorothioate oligonucleotide does not have a methylated guanine.

2. The method according to claim 1, wherein the phosphorothioate oligonucleotide is a phosphorothioate oligonucleotide consisting of:
a nucleotide sequence as set forth in SEQ ID NO: 40; or
a nucleotide sequence having deletion, substitution, or addition of one or more nucleotides in the nucleotide sequence as set forth in SEQ ID NO: 40 and having a binding ability to an HMGB protein.

3. The method according to claim 1, wherein the phosphorothioate oligonucleotide inhibits a binding between a nucleic acid activating the immune response and the HMGB protein in a cell.

4. The method according to claim 1, wherein the activation of an immune response mediated by an HMGB protein is selected from the group consisting of antigen-specific adaptive immune system, multiple sclerosis, excessive immune response to a dead cell, organ transplant rejection, autoimmune disease, inflammatory bowel disease, allergy, septicemia, tumor growth by inflammation and inflammatory disease caused by a nucleic acid-containing pathogen.

5. The method according to claim 1, wherein the phosphorothioate oligonucleotide is a phosphorothioate oligonucleotide consisting of:
a nucleotide sequence as set forth in SEQ ID NO: 40; or
a nucleotide sequence having deletion, substitution, or addition of one to five nucleotides in the nucleotide sequence as set forth in SEQ ID NO: 40 and having a binding ability to an HMGB protein.

6. The method according to claim 1, wherein the activation of an immune response mediated by an HMGB protein causes multiple sclerosis or septicemia.

7. The method according to claim 5, wherein the activation of an immune response mediated by an HMGB protein causes multiple sclerosis or septicemia.

8. The method according to claim 1, wherein the phosphorothioate oligonucleotide is a phosphorothioate oligonucleotide consisting of:
a nucleotide sequence as set forth in SEQ ID NO: 40; or
a nucleotide sequence having deletion, substitution, or addition of one to three nucleotides in the nucleotide sequence as set forth in SEQ ID NO: 40 and having a binding ability to an HMGB protein.

9. The method according to claim 8, wherein the activation of an immune response mediated by an HMGB protein causes multiple sclerosis or septicemia.

10. The method according to claim 1, wherein the phosphorothioate oligonucleotide is a phosphorothioate oligonucleotide consisting of a nucleotide sequence as set forth in SEQ ID NO: 40.

11. The method according to claim 10, wherein the activation of an immune response mediated by an HMGB protein causes multiple sclerosis or septicemia.

12. The method according to claim 1, wherein the phosphorothioate oligonucleotide is a phosphorothioate oligonucleotide comprising:
   a nucleotide sequence as set forth in SEQ ID NO: 40; or
   a nucleotide sequence having deletion, substitution, or addition of one or more nucleotides in the nucleotide sequence as set forth in SEQ ID NO: 40 and having a binding ability to an HMGB protein.

13. The method according to claim 1, wherein the phosphorothioate oligonucleotide is a phosphorothioate oligonucleotide comprising:
   a nucleotide sequence as set forth in SEQ ID NO: 40; or
   a nucleotide sequence having deletion, substitution, or addition of one to five nucleotides in the nucleotide sequence as set forth in SEQ ID NO: 40 and having a binding ability to an HMGB protein.

14. The method according to claim 13, wherein the activation of an immune response mediated by an HMGB protein causes multiple sclerosis or septicemia.

15. The method according to claim 1, wherein the phosphorothioate oligonucleotide is a phosphorothioate oligonucleotide comprising:
   a nucleotide sequence as set forth in SEQ ID NO: 40; or
   a nucleotide sequence having deletion, substitution, or addition of one to three nucleotides in the nucleotide sequence as set forth in SEQ ID NO: 40 and having a binding ability to an HMGB protein.

16. The method according to claim 15, wherein the activation of an immune response mediated by an HMGB protein causes multiple sclerosis or septicemia.

17. The method according to claim 1, wherein the phosphorothioate oligonucleotide is a phosphorothioate oligonucleotide comprising a nucleotide sequence as set forth in SEQ ID NO: 40.

18. The method according to claim 17, wherein the activation of an immune response mediated by an HMGB protein causes multiple sclerosis or septicemia.

19. The method according to claim 1, wherein the activation of an immune response mediated by an HMGB protein causes an inflammatory disease.

20. The method according to claim 1, wherein the phosphorothioate oligonucleotide is unmethylated.

21. The method according to claim 1, wherein the phosphorothioate oligonucleotide does not comprise a CG sequence.

* * * * *

SEQUENCE LISTING

<160> NUMBER OF SEQ ID NOS: 56

<210> SEQ ID NO 1
<211> LENGTH: 20
<212> TYPE: DNA
<213> ORGANISM: Artificial Sequence
<220> FEATURE:
<223> OTHER INFORMATION: CpG-B ODN

<400> SEQUENCE: 1
tccatgacgt tcctgatgct                                            20

<210> SEQ ID NO 2
<211> LENGTH: 20
<212> TYPE: DNA
<213> ORGANISM: Artificial Sequence
<220> FEATURE:
<223> OTHER INFORMATION: CpG-A ODN
<220> FEATURE:

```
<221> NAME/KEY: misc_feature
<222> LOCATION: (1)..(2)
<223> OTHER INFORMATION: phosphorothioate oligonucleotide
<220> FEATURE:
<221> NAME/KEY: misc_feature
<222> LOCATION: (15)..(19)
<223> OTHER INFORMATION: phosphorothioate oligonucleotide

<400> SEQUENCE: 2
ggtgcatcga tgcagggggg                                                 20

<210> SEQ ID NO 3
<211> LENGTH: 2781
<212> TYPE: DNA
<213> ORGANISM: Mus musculus
<220> FEATURE:
<221> NAME/KEY: misc_feature
<223> OTHER INFORMATION: RIG-I cDNA

<400> SEQUENCE: 3
atgacagcgg agcagcggca gaatctgcaa gcattcagag actatatcaa gaagattctg       60
gaccccacct acatcctcag ctacatgagt tcctggctcg aggatgagga ggtgcagtac      120
attcaggctg agaagaacaa caagggccca atggaagctg cctcactctt cctccagtac      180
ctgttgaagc tgcagtcaga gggctggttc caggcctttt tggatgccct gtaccatgca      240
ggttactgtg gactttgtga agccatcgaa agttgggact tcaaaaaaat tgaaaagtta      300
gaggaacaca gattactttt aagacgttta gaaccagaat ttaaggccac agttgatcca      360
aatgatatcc tttctgaact atccgaatgt ttgattaatc aggaatgtga agaaatcaga      420
cagatccgag acactaaagg gagaatggca ggtgcggaga gatggccga atgtcttatc       480 agatccgaca aggaaaactg gccaaaggtc ttgcaacttg ctttggagaa agacaacagc      540
aagtttagtg aattgtggat tgttgataaa ggtttcaaaa gggctgaaag caaggctgat      600
gaggatgatg gagcggaggc gtccagcatc cagattttca ttcaggaaga gccagagtgt      660
cagaatctca gtcagaatcc cgggcctcct tcagaagcgt cttctaataa tttacacagc      720
ccattgaaac caagaaatta ccaactggag cttgccctgc ctgccaagaa agggaaaaat      780
acaataatat gtgcccctac tggttgtgga aaaacctttg tgtcgcttct tatatgtgaa      840
caccatctta aaaaattccc atgtggacaa aagggaaag tggtcttctt cgctaaccaa       900
attcctgtct atgagcagca ggcaactgtg ttctcacgat attttgaaag acttgggtac      960
aacattgcga gcatttctgg ggcaacatct gatagcgtct cagtgcagca tcattgaa      1020 gacaatgata tcatcatcct gacccccag attcttgtga acaatctcaa caacggagcc     1080
atcccctcgt tgtctgtctt cactctgatg atatttgatg agtgtcataa cactagcaaa     1140
aaccacccat acaatcagat catgttcaga tacctagacc acaaacttgg agagtcacgg     1200
gacccactgc ctcaggtcgt tgggctgact gcctccgtcg gcgttggaga tgctaagacc     1260
gcggaggaag ccatgcaaca tatctgtaaa ctctgtgccg ccctggatgc ctccgtgatt     1320
gccacagtca gagacaacgt tgcagaactg gaacaggtcg tttataagcc ccagaaaatt    1380
tccaggaaag tggcatcccg gacttcgaac acgtttaaat gcatcatctc tcagctgatg     1440
aaggagacag agaagctagc caaggatgtc tccgaggaac ttggaaagct ttttcaaatt     1500
caaaacagag aattcggcac ccagaaatat gaacagtgga ttgtcggcgt ccacaaagcg     1560
tgctcagtgt ttcagatggc agacaaagag gaggagagcc gggtctgcaa agcgctcttc     1620
ctgtacacat cactttgcg gaaatacaac gatgcactca tcatcagtga ggatgcacag     1680
```

```
atgacagacg ctctaaatta cctcaaagcc ttcttccacg atgtccgaga agcagcattc   1740
gatgagaccg agcgagagct tactcggagg tttgaagaaa aactagagga attagaaaaa   1800
gtttccaggg atcccagcaa tgagaatcct aaactaagag acctctactt ggtcttacaa   1860
gaagagtacc acttaaagcc agagaccaag accattctct tcgtgaagac cagagcactc   1920
gtggatgctc tgaagaaatg gattgaagaa atcctgcac taagctttct aaagcctggc    1980
atactgactg ggcgtggcag aacaaaccgg gcaacaggaa tgacgctccc ggcacagaag   2040
tgtgtgctgg aggcattcag agccagcgga gataacaata ttctgattgc tacctcggtc   2100
gctgatgaag gcattgacat tgctgagtgc aatctcgtca ttctctatga gtacgtgggc   2160
aacgtcatca agatgatcca aaccagaggc cgaggaagag cacgagatag caagtgcttc   2220
ctcctgacca gcagcgctga cgtgattgaa aagaaaaagg cgaacatgat caaggaaaaa   2280
ataatgaatg aatccatctt aagactgcag acatgggatg aaatgaaatt tggaaagacg   2340
gttcaccgca tacaggtgaa tgaaaaactc ctcagagaca gtcagcacaa accacaacct   2400
gttcctgaca aagaaaacaa gaaactgctg tgtggaaagt gcaagaattt tgcgtgctac   2460
acagctgaca ttcgagtggt tgagacgtcc cactacactg tccttggaga cgcttttaag   2520
gagcgctttg tgtgtaagcc acaccctaaa ccaaagatct atgacaattt tgagaagaaa   2580
gcaaagatat tctgcgccaa acagaactgt agccacgact ggggaatttt tgtgagatac   2640
aagacgttcg agattccagt cataaaaatt gaaagtttcg tcgtggaaga tattgtgagc   2700
ggagttcaga accggcactc aaagtggaag gactttcatt ttgaaaggat acagttcgat   2760
cctgcagaaa tgtccgtatg a                                             2781
```

<210> SEQ ID NO 4
<211> LENGTH: 648
<212> TYPE: DNA
<213> ORGANISM: Mus musculus
<220> FEATURE:
<221> NAME/KEY: misc_feature
<223> OTHER INFORMATION: HMGB1 cDNA

<400> SEQUENCE: 4

```
atgggcaaag gagatcctaa aaagccgaga ggcaaaatgt cctcatatgc attctttgtg    60
caaacttgcc gggaggagca caagaagaag cacccggatg cttctgtcaa cttctcagag   120
ttctccaaga gtgctcaga gaggtggaag accatgtctg ctaaagaaaa ggggaaattt   180
gaagatatgg caaaggctga caaggctcgt tatgaaagag aaatgaaaac ctacatcccc   240
cccaaagggg agaccaaaaa gaagttcaag gaccccaatg cacccaagag gcctccttcg   300
gccttcttct tgttctgttc tgagtaccgc cccaaaatca aggcgagca tcctggctta   360 tccattggtg atgttgcaaa gaaactagga gagatgtgga acaacactgc agcagatgac   420
aagcagccct atgagaagaa agctgccaag ctgaaggaga agtatgagaa ggatattgct   480
gcctacagag ctaaaggaaa acctgatgca gcgaaaaagg gggtggtcaa ggctgaaaag   540
agcaagaaaa agaaggaaga ggaagatgat gaggaggatg aagaggatga ggaagaggag   600
gaagaagagg aagacgaaga tgaagaagaa gatgatgatg atgaataa                648
```

<210> SEQ ID NO 5
<211> LENGTH: 648
<212> TYPE: DNA
<213> ORGANISM: Mus musculus
<220> FEATURE:
<221> NAME/KEY: misc_feature
<223> OTHER INFORMATION: Rab5 cDNA

```
<400> SEQUENCE: 5
atggctaatc gaggagcaac aagacccaac gggccaaata ctggaaataa aatatgccag    60
ttcaaactgg tccttctagg agagtctgct gttggcaaat caagcctggt tcttcgcttt   120
gtgaaaggcc aatttcatga atttcaagag agtaccattg gggctgcctt tctaacccaa   180
actgtgtgtc ttgatgacac aacagtaaaa tttgaaatat gggatacagc tggtcaagaa   240
cggtatcata gcttagcacc aatgtactac cgaggagcac aagcagccat agttgtgtat   300
gatatcacaa atgaggaatc ctttgcgaga gcaaaaaact gggttaaaga acttcaaagg   360
caagcaagtc ctaatattgt gatagctttg tcaggaaaca aagctgactt agcaaataaa   420
agagctgttg acttccagga agcacagtcc tatgcagatg acaacagctt attatttatg   480
gagacatcag ctaagacatc aatgaatgta aatgaaatat ttatggcaat agctaaaaag   540
ctgccaaaga atgaaccaca gaatcctggt gcaaactcag ccagaggacg aggagtagac   600
cttactgagc ctgcacagcc agccagaagc cagtgttgta gtaactga                648

<210> SEQ ID NO 6
<211> LENGTH: 20
<212> TYPE: DNA
<213> ORGANISM: Artificial Sequence
<220> FEATURE:
<223> OTHER INFORMATION: primer HMGB1 sense

<400> SEQUENCE: 6
ccaaagggga gaccaaaaag                                                20

<210> SEQ ID NO 7
<211> LENGTH: 21
<212> TYPE: DNA
<213> ORGANISM: Artificial Sequence
<220> FEATURE:
<223> OTHER INFORMATION: primer HMGB1 antisense

<400> SEQUENCE: 7
tcatagggct gcttgtcatc t                                              21

<210> SEQ ID NO 8
<211> LENGTH: 20
<212> TYPE: DNA
<213> ORGANISM: Artificial Sequence
<220> FEATURE:
<223> OTHER INFORMATION: primer HMGB2 sense

<400> SEQUENCE: 8
tgccttcttc ctgttttgct                                                20

<210> SEQ ID NO 9
<211> LENGTH: 20
<212> TYPE: DNA
<213> ORGANISM: Artificial Sequence
<220> FEATURE:
<223> OTHER INFORMATION: primer HMGB2 antisense

<400> SEQUENCE: 9
ggacccttct ttcctgcttc                                                20

<210> SEQ ID NO 10
<211> LENGTH: 23
<212> TYPE: DNA
<213> ORGANISM: Artificial Sequence
<220> FEATURE:
```

<223> OTHER INFORMATION: primer HMGB3 sense

<400> SEQUENCE: 10
ggagatgaaa gattatggac cag                                              23

<210> SEQ ID NO 11
<211> LENGTH: 16
<212> TYPE: DNA
<213> ORGANISM: Artificial Sequence
<220> FEATURE:
<223> OTHER INFORMATION: primer HMGB3 antisense

<400> SEQUENCE: 11
ctttgctgcc ttggtg                                                      16

<210> SEQ ID NO 12
<211> LENGTH: 20
<212> TYPE: DNA
<213> ORGANISM: Artificial Sequence
<220> FEATURE:
<223> OTHER INFORMATION: primer GBP1 sense

<400> SEQUENCE: 12
ctcagcagca gtgcaaaagg                                                  20

<210> SEQ ID NO 13
<211> LENGTH: 20
<212> TYPE: DNA
<213> ORGANISM: Artificial Sequence
<220> FEATURE:
<223> OTHER INFORMATION: primer GBP1 antisense

<400> SEQUENCE: 13
gctcctggag ggtttctgtg                                                  20

<210> SEQ ID NO 14
<211> LENGTH: 18
<212> TYPE: DNA
<213> ORGANISM: Artificial Sequence
<220> FEATURE:
<223> OTHER INFORMATION: primer IRF7 sense

<400> SEQUENCE: 14
gcaagggtca ccacacta                                                    18

<210> SEQ ID NO 15
<211> LENGTH: 18
<212> TYPE: DNA
<213> ORGANISM: Artificial Sequence
<220> FEATURE:
<223> OTHER INFORMATION: primer IRF7 antisense

<400> SEQUENCE: 15
caagcacaag ccgagact                                                    18

<210> SEQ ID NO 16
<211> LENGTH: 21
<212> TYPE: DNA
<213> ORGANISM: Artificial Sequence
<220> FEATURE:
<223> OTHER INFORMATION: primer IL-12p40 sense

<400> SEQUENCE: 16
gacacgcctg aagaagatga c                                                21

```
<210> SEQ ID NO 17
<211> LENGTH: 21
<212> TYPE: DNA
<213> ORGANISM: Artificial Sequence
<220> FEATURE:
<223> OTHER INFORMATION: primer IL-12p40 antisense

<400> SEQUENCE: 17
tagtcccttt ggtccagtgt g                                          21

<210> SEQ ID NO 18
<211> LENGTH: 20
<212> TYPE: DNA
<213> ORGANISM: Artificial Sequence
<220> FEATURE:
<223> OTHER INFORMATION: primer GAPDH sense

<400> SEQUENCE: 18
ctcatgacca cagtccatgc                                            20

<210> SEQ ID NO 19
<211> LENGTH: 20
<212> TYPE: DNA
<213> ORGANISM: Artificial Sequence
<220> FEATURE:
<223> OTHER INFORMATION: primer GAPDH antisense

<400> SEQUENCE: 19
cacattgggg gtaggaacac                                            20

<210> SEQ ID NO 20
<211> LENGTH: 25
<212> TYPE: DNA
<213> ORGANISM: Artificial Sequence
<220> FEATURE:
<223> OTHER INFORMATION: primer IL-6 sense

<400> SEQUENCE: 20
atgaagttcc tctctgcaag agact                                      25

<210> SEQ ID NO 21
<211> LENGTH: 24
<212> TYPE: DNA
<213> ORGANISM: Artificial Sequence
<220> FEATURE:
<223> OTHER INFORMATION: primer IL-6 antisense

<400> SEQUENCE: 21
cactaggttt gccgagtaga tctc                                       24

<210> SEQ ID NO 22
<211> LENGTH: 22
<212> TYPE: DNA
<213> ORGANISM: Artificial Sequence
<220> FEATURE:
<223> OTHER INFORMATION: primer RANTES sense

<400> SEQUENCE: 22
acgtcaagga gtatttctac ac                                         22

<210> SEQ ID NO 23
<211> LENGTH: 20
<212> TYPE: DNA
<213> ORGANISM: Artificial Sequence
<220> FEATURE:
<223> OTHER INFORMATION: primer RANTES antisense
```

<400> SEQUENCE: 23
gatgtattct tgaacccact                                          20

<210> SEQ ID NO 24
<211> LENGTH: 18
<212> TYPE: DNA
<213> ORGANISM: Artificial Sequence
<220> FEATURE:
<223> OTHER INFORMATION: primer I Kappa B-alpha sense

<400> SEQUENCE: 24
ttggtgactt tgggtgct                                            18

<210> SEQ ID NO 25
<211> LENGTH: 19
<212> TYPE: DNA
<213> ORGANISM: Artificial Sequence
<220> FEATURE:
<223> OTHER INFORMATION: primer I Kappa B-alpha antisense

<400> SEQUENCE: 25
tgacatcagc cccacattt                                           19

<210> SEQ ID NO 26
<211> LENGTH: 26
<212> TYPE: DNA
<213> ORGANISM: Artificial Sequence
<220> FEATURE:
<223> OTHER INFORMATION: primer IFN-alpha1 sense

<400> SEQUENCE: 26
gccttgacac tcctggtaca aatgag                                   26

<210> SEQ ID NO 27
<211> LENGTH: 24
<212> TYPE: DNA
<213> ORGANISM: Artificial Sequence
<220> FEATURE:
<223> OTHER INFORMATION: primer IFN-alpha1 antisense

<400> SEQUENCE: 27
cagcacattg gcagaggaag acag                                     24

<210> SEQ ID NO 28
<211> LENGTH: 20
<212> TYPE: DNA
<213> ORGANISM: Artificial Sequence
<220> FEATURE:
<223> OTHER INFORMATION: primer IFN-alpha4 sense

<400> SEQUENCE: 28
gacgacagcc aaagaagtga                                          20

<210> SEQ ID NO 29
<211> LENGTH: 20
<212> TYPE: DNA
<213> ORGANISM: Artificial Sequence
<220> FEATURE:
<223> OTHER INFORMATION: primer IFN-alpha4 antisense

<400> SEQUENCE: 29
gagctatgtc ttggccttcc                                          20

<210> SEQ ID NO 30
<211> LENGTH: 26

```
<212> TYPE: DNA
<213> ORGANISM: Artificial Sequence
<220> FEATURE:
<223> OTHER INFORMATION: primer IFN-beta sense

<400> SEQUENCE: 30
ccaccacagc cctctccatc aactat                                              26

<210> SEQ ID NO 31
<211> LENGTH: 25
<212> TYPE: DNA
<213> ORGANISM: Artificial Sequence
<220> FEATURE:
<223> OTHER INFORMATION: primer IFN-beta antisense

<400> SEQUENCE: 31
caagtggaga gcagttgagg acatc                                               25

<210> SEQ ID NO 32
<211> LENGTH: 19
<212> TYPE: DNA
<213> ORGANISM: Artificial Sequence
<220> FEATURE:
<223> OTHER INFORMATION: HMGB1,2 and 3 siRNA target sequence

<400> SEQUENCE: 32
gtatgagaag gatattgct                                                      19

<210> SEQ ID NO 33
<211> LENGTH: 19
<212> TYPE: DNA
<213> ORGANISM: Artificial Sequence
<220> FEATURE:
<223> OTHER INFORMATION: HMGB2 siRNA target sequence

<400> SEQUENCE: 33
gcgttacgag aaaccagtt                                                      19

<210> SEQ ID NO 34
<211> LENGTH: 20
<212> TYPE: DNA
<213> ORGANISM: Artificial Sequence
<220> FEATURE:
<223> OTHER INFORMATION: Renilla luciferase siRNA target sequence

<400> SEQUENCE: 34
gtagcgcggt gtattataca                                                     20

<210> SEQ ID NO 35
<211> LENGTH: 45
<212> TYPE: DNA
<213> ORGANISM: Artificial Sequence
<220> FEATURE:
<223> OTHER INFORMATION: NF Kappa B consensus sequence

<400> SEQUENCE: 35
tcgacccggg actttccgcc gggactttcc gccgggactt tccgg                         45

<210> SEQ ID NO 36
<211> LENGTH: 45
<212> TYPE: DNA
<213> ORGANISM: Artificial Sequence
<220> FEATURE:
<223> OTHER INFORMATION: IFN stimulatory DNA (ISD)

<400> SEQUENCE: 36
```

```
tacagatcta ctagtgatct atgactgatc tgtacatgat ctaca                      45
```

<210> SEQ ID NO 37
<211> LENGTH: 20
<212> TYPE: DNA
<213> ORGANISM: Artificial Sequence
<220> FEATURE:
<223> OTHER INFORMATION: CpG-B(S)
<220> FEATURE:
<221> NAME/KEY: misc_feature
<223> OTHER INFORMATION: phosphorothioate oligonucleotide
<400> SEQUENCE: 37

```
tccatgacgt tcctgatgct                                                  20
```

<210> SEQ ID NO 38
<211> LENGTH: 20
<212> TYPE: DNA
<213> ORGANISM: Artificial Sequence
<220> FEATURE:
<223> OTHER INFORMATION: CpG-Rev(S)
<220> FEATURE:
<221> NAME/KEY: misc_feature
<223> OTHER INFORMATION: phosphorothioate oligonucleotide
<400> SEQUENCE: 38

```
tccatgagct tcctgatgct                                                  20
```

<210> SEQ ID NO 39
<211> LENGTH: 20
<212> TYPE: DNA
<213> ORGANISM: Artificial Sequence
<220> FEATURE:
<223> OTHER INFORMATION: CpG-M(S)
<220> FEATURE:
<221> NAME/KEY: misc_feature
<223> OTHER INFORMATION: phosphorothioate oligonucleotide
<400> SEQUENCE: 39

```
tccatgaggt tcctgatgct                                                  20
```

<210> SEQ ID NO 40
<211> LENGTH: 20
<212> TYPE: DNA
<213> ORGANISM: Artificial Sequence
<220> FEATURE:
<223> OTHER INFORMATION: CpG-Rev(S)/CpG-M(S)
<220> FEATURE:
<221> NAME/KEY: misc_feature
<223> OTHER INFORMATION: phosphorothioate oligonucleotide
<220> FEATURE:
<221> NAME/KEY: misc_feature
<222> LOCATION: (9)..(9)
<223> OTHER INFORMATION: s = g or c
<400> SEQUENCE: 40

```
tccatgagst tcctgatgct                                                  20
```

<210> SEQ ID NO 41
<211> LENGTH: 10
<212> TYPE: DNA
<213> ORGANISM: Artificial Sequence
<220> FEATURE:
<223> OTHER INFORMATION: poly(dA)(S), 10 mer
<220> FEATURE:
<221> NAME/KEY: misc_feature
<223> OTHER INFORMATION: phosphorothioate oligonucleotide
<400> SEQUENCE: 41
aaaaaaaaaa                                                                      10

<210> SEQ ID NO 42
<211> LENGTH: 15
<212> TYPE: DNA
<213> ORGANISM: Artificial Sequence
<220> FEATURE:
<223> OTHER INFORMATION: poly(dA)(S), 15 mer
<220> FEATURE:
<221> NAME/KEY: misc_feature
<223> OTHER INFORMATION: phosphorothioate oligonucleotide

<400> SEQUENCE: 42
aaaaaaaaaa aaaaa                                                                15

<210> SEQ ID NO 43
<211> LENGTH: 20
<212> TYPE: DNA
<213> ORGANISM: Artificial Sequence
<220> FEATURE:
<223> OTHER INFORMATION: poly(dA)(S), 20 mer
<220> FEATURE:
<221> NAME/KEY: misc_feature
<223> OTHER INFORMATION: phosphorothioate oligonucleotide

<400> SEQUENCE: 43
aaaaaaaaaa aaaaaaaaaa                                                           20

<210> SEQ ID NO 44
<211> LENGTH: 10
<212> TYPE: DNA
<213> ORGANISM: Artificial Sequence
<220> FEATURE:
<223> OTHER INFORMATION: poly(dC)(S), 10 mer
<220> FEATURE:
<221> NAME/KEY: misc_feature
<223> OTHER INFORMATION: phosphorothioate oligonucleotide

<400> SEQUENCE: 44
cccccccccc                                                                      10

<210> SEQ ID NO 45
<211> LENGTH: 15
<212> TYPE: DNA
<213> ORGANISM: Artificial Sequence
<220> FEATURE:
<223> OTHER INFORMATION: poly(dC)(S), 15 mer
<220> FEATURE:
<221> NAME/KEY: misc_feature
<223> OTHER INFORMATION: phosphorothioate oligonucleotide

<400> SEQUENCE: 45
cccccccccc ccccc                                                                15

<210> SEQ ID NO 46
<211> LENGTH: 20
<212> TYPE: DNA
<213> ORGANISM: Artificial Sequence
<220> FEATURE:
<223> OTHER INFORMATION: poly(dC)(S), 20 mer
<220> FEATURE:
<221> NAME/KEY: misc_feature
<223> OTHER INFORMATION: phosphorothioate oligonucleotide

<400> SEQUENCE: 46
cccccccccc cccccccccc                                                           20

<210> SEQ ID NO 47

<211> LENGTH: 22
<212> TYPE: DNA
<213> ORGANISM: Artificial Sequence
<220> FEATURE:
<223> OTHER INFORMATION: primer Ifna4 Fw

<400> SEQUENCE: 47
caatgacctc aaagcctgtg tg                                    22

<210> SEQ ID NO 48
<211> LENGTH: 20
<212> TYPE: DNA
<213> ORGANISM: Artificial Sequence
<220> FEATURE:
<223> OTHER INFORMATION: primer Ifna4 Rv

<400> SEQUENCE: 48
cacagtgatc ctgtggaagt                                       20

<210> SEQ ID NO 49
<211> LENGTH: 26
<212> TYPE: DNA
<213> ORGANISM: Artificial Sequence
<220> FEATURE:
<223> OTHER INFORMATION: primer Ifnb1 Fw

<400> SEQUENCE: 49
ccaccacagc cctctccatc aactat                                26

<210> SEQ ID NO 50
<211> LENGTH: 25
<212> TYPE: DNA
<213> ORGANISM: Artificial Sequence
<220> FEATURE:
<223> OTHER INFORMATION: primer Ifnb1 Rv

<400> SEQUENCE: 50
caagtggaga gcagttgagg acatc                                 25

<210> SEQ ID NO 51
<211> LENGTH: 20
<212> TYPE: DNA
<213> ORGANISM: Artificial Sequence
<220> FEATURE:
<223> OTHER INFORMATION: primer Il6 Fw

<400> SEQUENCE: 51
acgatgatgc acttgcagaa                                       20

<210> SEQ ID NO 52
<211> LENGTH: 23
<212> TYPE: DNA
<213> ORGANISM: Artificial Sequence
<220> FEATURE:
<223> OTHER INFORMATION: primer Il6 Rv

<400> SEQUENCE: 52
gtagctatgg tactccagaa gac                                   23

<210> SEQ ID NO 53
<211> LENGTH: 24
<212> TYPE: DNA
<213> ORGANISM: Artificial Sequence
<220> FEATURE:
<223> OTHER INFORMATION: primer Tnfa Fw

<400> SEQUENCE: 53

```
tcataccagg agaaagtcaa cctc                                              24

<210> SEQ ID NO 54
<211> LENGTH: 24
<212> TYPE: DNA
<213> ORGANISM: Artificial Sequence
<220> FEATURE:
<223> OTHER INFORMATION: primer Tnfa Rv

<400> SEQUENCE: 54
gtatatgggc tcataccagg gttt                                              24

<210> SEQ ID NO 55
<211> LENGTH: 22
<212> TYPE: DNA
<213> ORGANISM: Artificial Sequence
<220> FEATURE:
<223> OTHER INFORMATION: CpG ODN 1018(S)
<220> FEATURE:
<221> NAME/KEY: misc_feature
<223> OTHER INFORMATION: phosphorothioate oligonucleotide

<400> SEQUENCE: 55
tgactgtgaa cgttcgagat ga                                                22

<210> SEQ ID NO 56
<211> LENGTH: 22
<212> TYPE: DNA
<213> ORGANISM: Artificial Sequence
<220> FEATURE:
<223> OTHER INFORMATION: ODN 1019(S)
<220> FEATURE:
<221> NAME/KEY: misc_feature
<223> OTHER INFORMATION: phosphorothioate oligonucleotide

<400> SEQUENCE: 56
tgactgtgaa ggttagagat ga                                                22
```